(12) United States Patent
Camphausen et al.

(10) Patent No.: US 10,273,286 B2
(45) Date of Patent: *Apr. 30, 2019

(54) FIBRONECTIN BASED SCAFFOLD PROTEINS HAVING IMPROVED STABILITY

(71) Applicant: BRISTOL-MYERS SQUIBB COMPANY, Princeton, NJ (US)

(72) Inventors: Ray Camphausen, Wayland, MA (US); John O'Loughlin, Stow, MA (US); Bernice Yeung, Lexington, MA (US); Yihong Zhang, Acton, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,222

(22) Filed: Dec. 20, 2016

(65) Prior Publication Data
US 2017/0166627 A1 Jun. 15, 2017

Related U.S. Application Data

(63) Continuation of application No. 13/699,458, filed as application No. PCT/US2011/038013 on May 26, 2011, now Pat. No. 9,562,089.

(60) Provisional application No. 61/348,663, filed on May 26, 2010, provisional application No. 61/348,647, filed on May 26, 2010.

(51) Int. Cl.
| | |
|---|---|
| C07K 16/18 | (2006.01) |
| C07K 16/28 | (2006.01) |
| C07K 14/78 | (2006.01) |
| A61K 39/395 | (2006.01) |
| C07K 14/435 | (2006.01) |
| C07K 14/525 | (2006.01) |
| C07K 14/715 | (2006.01) |
| C07K 14/71 | (2006.01) |
| A61K 38/00 | (2006.01) |

(52) U.S. Cl.
CPC .............. *C07K 14/78* (2013.01); *C07K 16/18* (2013.01); *A61K 38/00* (2013.01); *C07K 14/71* (2013.01); *C07K 14/7155* (2013.01); *C07K 16/2863* (2013.01); *C07K 2317/31* (2013.01); *C07K 2317/34* (2013.01); *C07K 2317/56* (2013.01); *C07K 2317/565* (2013.01); *C07K 2317/92* (2013.01); *C07K 2317/94* (2013.01); *C07K 2318/20* (2013.01); *C07K 2319/00* (2013.01); *C07K 2319/30* (2013.01)

(58) Field of Classification Search
CPC .... A61K 38/17; A61K 38/39; C07K 2317/31; C07K 2317/92; C07K 16/2863; C07K 2317/622; C07K 14/78; C07K 14/47
See application file for complete search history.

(56) References Cited

U.S. PATENT DOCUMENTS

| | | |
|---|---|---|
| 3,773,919 A | 11/1973 | Boswell et al. |
| 4,863,457 A | 9/1989 | Lee |
| 4,997,652 A | 3/1991 | Wong |
| 5,164,188 A | 11/1992 | Wong |
| 5,235,041 A | 8/1993 | Cappello et al. |
| 5,443,505 A | 8/1995 | Wong et al. |
| 5,501,856 A | 3/1996 | Ohtori et al. |
| 5,514,581 A | 5/1996 | Ferrari et al. |
| 5,516,522 A | 5/1996 | Peyman et al. |
| 5,545,620 A | 8/1996 | Wahl et al. |
| 5,641,648 A | 6/1997 | Ferrari et al. |
| 5,766,242 A | 6/1998 | Wong et al. |
| 5,770,697 A | 6/1998 | Ferrari et al. |
| 5,792,742 A | 8/1998 | Gold et al. |
| 5,824,072 A | 10/1998 | Wong |
| 5,869,079 A | 2/1999 | Wong et al. |
| 5,922,676 A | 7/1999 | Pasqualini et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,316,412 B1 | 11/2001 | Ginsberg et al. |
| 6,342,219 B1 | 1/2002 | Thorpe et al. |
| 6,348,333 B1 | 2/2002 | Niwa et al. |
| 6,369,116 B1 | 4/2002 | Wong et al. |

(Continued)

FOREIGN PATENT DOCUMENTS

| | | |
|---|---|---|
| CA | 2293632 A1 | 12/1998 |
| DE | 19646372 C1 | 6/1997 |

(Continued)

OTHER PUBLICATIONS

Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).

(Continued)

*Primary Examiner* — Bridget E Bunner

(74) *Attorney, Agent, or Firm* — Nelson Mullins Riley & Scarborough LLP; Jane E. Remillard, Esq.; Christopher L. Frank

(57) ABSTRACT

The present application provides fibronectin based scaffold proteins associated with improved stability. The application also relates to stable formulations of fibronectin based scaffold proteins and the use thereof in diagnostic, research and therapeutic applications. The application further relates to cells comprising such proteins, polynucleotides encoding such proteins or fragments thereof, and to vectors comprising such polynucleotides.

8 Claims, 15 Drawing Sheets

Specification includes a Sequence Listing.

(56) References Cited

U.S. PATENT DOCUMENTS

| | | |
|---|---|---|
| 6,383,775 B1 | 5/2002 | Duff et al. |
| 6,462,189 B1 | 10/2002 | Koide |
| 6,518,018 B1 | 2/2003 | Szostak et al. |
| 6,524,583 B1 | 2/2003 | Thorpe et al. |
| 6,559,126 B2 | 5/2003 | Tournaire et al. |
| 6,660,492 B1 | 12/2003 | Bode et al. |
| 6,699,493 B2 | 3/2004 | Wong |
| 6,818,418 B1 | 11/2004 | Lipovsek et al. |
| 7,053,701 B2 | 5/2006 | Vice |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 7,858,759 B2 | 12/2010 | Brandt et al. |
| 7,882,645 B2 | 2/2011 | Boring |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,420,098 B2 | 4/2013 | Camphausen et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 8,853,154 B2 | 10/2014 | Cload et al. |
| 8,933,199 B2 | 1/2015 | Cload et al. |
| 8,969,289 B2 | 3/2015 | Gosselin et al. |
| 9,017,655 B2 | 4/2015 | Emanuel et al. |
| 9,234,028 B2 | 1/2016 | Camphausen et al. |
| 9,328,157 B2 | 5/2016 | Chen et al. |
| 9,562,089 B2 | 2/2017 | Camphausen et al. |
| 9,605,039 B2 | 3/2017 | Lipovsek et al. |
| 9,771,411 B2 | 9/2017 | Emanuel et al. |
| 9,862,758 B2 | 1/2018 | Chen et al. |
| 9,902,762 B2 | 2/2018 | Camphausen |
| 9,920,108 B2 | 3/2018 | Camphausen et al. |
| 2002/0019517 A1 | 2/2002 | Koide |
| 2002/0061307 A1 | 5/2002 | Whitlow et al. |
| 2002/0142048 A1 | 10/2002 | Sands et al. |
| 2003/0045681 A1 | 3/2003 | Neri et al. |
| 2003/0104520 A1 | 6/2003 | Ellington et al. |
| 2003/0170753 A1 | 9/2003 | Koide |
| 2003/0186385 A1 | 10/2003 | Koide |
| 2005/0244469 A1 | 11/2005 | Whitcup et al. |
| 2005/0255548 A1 | 11/2005 | Lipovsek et al. |
| 2005/0281861 A1 | 12/2005 | Hughes et al. |
| 2006/0122162 A1 | 6/2006 | Cutler |
| 2006/0182783 A1 | 8/2006 | Hughes et al. |
| 2006/0210604 A1 | 9/2006 | Dadey et al. |
| 2006/0246059 A1 | 11/2006 | Lipovsek et al. |
| 2006/0246549 A1 | 11/2006 | Kurz et al. |
| 2007/0059336 A1 | 3/2007 | Hughes et al. |
| 2007/0071575 A1 | 3/2007 | Rudduck et al. |
| 2007/0071675 A1 | 3/2007 | Wu et al. |
| 2007/0072933 A1 | 3/2007 | Peyman |
| 2007/0082365 A1 | 4/2007 | Lipovsek et al. |
| 2007/0088014 A1 | 4/2007 | Edelman et al. |
| 2007/0099879 A1 | 5/2007 | Sheibani et al. |
| 2007/0160533 A1 | 7/2007 | Chen et al. |
| 2007/0203089 A1 | 8/2007 | Rodrigues et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0193445 A1 | 8/2008 | Goetsch et al. |
| 2008/0220049 A1 | 9/2008 | Chen et al. |
| 2008/0268051 A1 | 10/2008 | Hughes et al. |
| 2009/0118181 A1 | 5/2009 | Walker et al. |
| 2009/0176654 A1 | 7/2009 | Cappuccilli et al. |
| 2009/0299040 A1 | 12/2009 | Camphausen et al. |
| 2010/0121033 A1 | 5/2010 | Camphausen et al. |
| 2010/0144599 A1 | 6/2010 | Mendlein et al. |
| 2010/0144601 A1 | 6/2010 | Jacobs et al. |
| 2010/0152063 A1 | 6/2010 | Cappuccilli et al. |
| 2010/0179094 A1 | 7/2010 | Emanuel et al. |
| 2010/0210511 A1 | 8/2010 | Carvajal |
| 2010/0273216 A1 | 10/2010 | Morin et al. |
| 2010/0285000 A1 | 11/2010 | Mamluk |
| 2010/0298541 A1 | 11/2010 | Wu et al. |
| 2010/0310549 A1 | 12/2010 | Chen et al. |
| 2010/0322930 A1 | 12/2010 | Kolbinger et al. |
| 2011/0021746 A1 | 1/2011 | Cappuccilli et al. |
| 2011/0034384 A1 | 2/2011 | Carvajal |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0184212 A1 | 7/2013 | Camphausen et al. |
| 2013/0237684 A1 | 9/2013 | Koide |
| 2013/0267676 A1 | 10/2013 | Koide |
| 2013/0310317 A1 | 11/2013 | Camphausen et al. |
| 2014/0094595 A1 | 4/2014 | Lipovsek et al. |
| 2014/0349929 A1 | 11/2014 | Camphausen et al. |
| 2015/0152147 A1 | 6/2015 | Gosselin et al. |
| 2015/0252097 A1 | 9/2015 | Camphausen et al. |
| 2015/0259398 A1 | 9/2015 | Emanuel et al. |
| 2016/0152688 A1 | 6/2016 | Camphausen et al. |
| 2016/0297869 A1 | 10/2016 | Chen et al. |
| 2017/0190761 A1 | 7/2017 | Camphausen et al. |
| 2017/0275342 A1 | 9/2017 | Lipovsek et al. |
| 2017/0334958 A1 | 11/2017 | Lipovsek et al. |
| 2018/0037631 A1 | 2/2018 | Emanuel et al. |

FOREIGN PATENT DOCUMENTS

| | | |
|---|---|---|
| EP | 0430539 A2 | 6/1991 |
| EP | 0488401 A1 | 6/1992 |
| EP | 0654256 A1 | 5/1995 |
| EP | 0962527 A1 | 12/1999 |
| EP | 0985039 B1 | 3/2000 |
| EP | 1477561 B1 | 11/2004 |
| EP | 1266025 B1 | 11/2006 |
| EP | 1137941 B1 | 8/2009 |
| EP | 2141243 A2 | 1/2010 |
| EP | 2385067 A1 | 11/2011 |
| EP | 2439212 A1 | 4/2012 |
| EP | 2379718 B1 | 3/2013 |
| JP | 4-108827 B2 | 4/1992 |
| JP | 2001-500531 A | 1/2001 |
| JP | 2007-516707 A | 6/2007 |
| WO | 92/02536 A1 | 2/1992 |
| WO | 93/03172 A1 | 2/1993 |
| WO | 95/11922 A1 | 5/1995 |
| WO | 95/13765 A1 | 5/1995 |
| WO | 96/22391 A1 | 7/1996 |
| WO | 98/12226 A1 | 3/1998 |
| WO | 98/31700 A1 | 7/1998 |
| WO | 98/56915 A2 | 12/1998 |
| WO | 99/51773 A1 | 10/1999 |
| WO | 2000/34784 A1 | 6/2000 |
| WO | 2000/34787 A1 | 6/2000 |
| WO | 2001/07657 A1 | 2/2001 |
| WO | 2001/64942 A1 | 9/2001 |
| WO | 2002/04523 A2 | 1/2002 |
| WO | 2002/32925 A2 | 4/2002 |
| WO | 2002/081497 A2 | 10/2002 |
| WO | 2002/088171 A2 | 11/2002 |
| WO | 2003/022858 A2 | 3/2003 |
| WO | 2003/072082 A1 | 9/2003 |
| WO | 2003/075840 A2 | 9/2003 |
| WO | 2003/104418 A2 | 12/2003 |
| WO | 2005/016970 A2 | 2/2005 |

(56) References Cited

FOREIGN PATENT DOCUMENTS

| WO | 2005/056764 A2 | 6/2005 |
|---|---|---|
| WO | 2006/020258 A2 | 2/2006 |
| WO | 2006/091209 A2 | 8/2006 |
| WO | 2007/012614 A2 | 2/2007 |
| WO | 2007/044688 A1 | 4/2007 |
| WO | 07/054120 A1 | 5/2007 |
| WO | 2007/062188 A2 | 5/2007 |
| WO | 2007/092537 A2 | 8/2007 |
| WO | 2007/096076 A2 | 8/2007 |
| WO | 2007/121894 A2 | 11/2007 |
| WO | 2008/019290 A2 | 2/2008 |
| WO | 2008/031098 A1 | 3/2008 |
| WO | 2008/048970 A2 | 4/2008 |
| WO | 2008/066752 A2 | 6/2008 |
| WO | 2008/097497 A2 | 8/2008 |
| WO | 2008/108986 A2 | 9/2008 |
| WO | 2008/153745 A2 | 12/2008 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |
| WO | 2009/083804 A2 | 7/2009 |
| WO | 2009/086116 A2 | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |

OTHER PUBLICATIONS

Li, Ning et al., "Factors affecting cleavage at aspartic residues in model decapeptides," Journal of Pharmaceutical and Biomedical Analysis, vol. 50:73-78 (2009).

Lipovsek, D., "Adnectins: engineered target-binding protein therapeutics," Protein Engineering, Design & Selection, vol. 24(1-2):3-9 (2011).

Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).

Lipovsek, Dasa et al., "In-vitro protein evolution by ribosome display and mRNA display," Journal of Immunological Methods, vol. 290:51-67 (2004).

Litvinovich, Sergei V. et al., "Interactions Between Type III Domains in the 110 kDa Cell-binding Fragments of Fibronectin," J. Mol. Biol., vol. 248:611-626 (1995).

Liu, Zhihong et al., "Fine mapping of the antigen-antibody interaction of scFv215, a recombinant antibody inhibiting RNA polymerase II from *Drosophila melanogaster*," Journal of Molecular Recognition, vol. 12:103-111 (1999).

Lombardo, A. et al., "Conformational flexibility and crystallization of tandemly linked type III modules of human fibronectin," Protein Science, vol. 5:1934-1938 (1996).

Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).

Lu, Dan et al., "Tailoring in Vitro Selection for a Picomolar Affinity Human Antibody Directed against Vascular Endothelial Growth Factor Receptor 2 for Enhanced Neutralizing Activity," The Journal of Biological Chemistry, vol. 278(44):43496-43507 (2003).

Lyden, David et al., "Impaired recruitment of bone-marrow-derived endothelial and hematopoietic precursor cells blocks tumor angiogenesis and growth," Nature Medicine, vol. 7(11):1194-1201 (2001).

Maeda, Hiroshi et al., "SMANCS and polymer-conjugated macromolecular drugs: advantages in cancer chemotherapy," Advanced Drug Delivery Reviews, vol. 46:169-185 (2001).

Main, Alison L. et al., "The Three-Dimensional Structure of the Tenth Type III Module of Fibronectin: An Insight into RGD-Mediated Interactions," Cell, vol. 71:671-678 (1992).

Mamluk, Roni et al., "Anti-tumor effect of CT-322 as an adnectin inhibitor of vascular endothelial growth factor receptor-2," mAbs, vol. 2(2):199-208 (2010).

Mao, Yong et al., "Fibronectin fibrillogenesis, a cell-mediated matrix assembly process," Matrix Biology, vol. 24:389-399 (2005).

Markland, William et al., "Iterative Optimization of High-Affinity Protease Inhibitors Using Phage Display. 1. Plasmin," Biochemistry, vol. 35:8045-8057 (1996).

Markland, William et al., "Iterative Optimization of High-Affinity Protease Inhibitors Using Phage Display. 2. Plasma Kallikrein and Thrombin," Biochemistry, vol. 35:8058-8067 (1996).

Maruyama, Kazuo et al., "Oligo-capping: a simple method to replace the cap structure of eukaryotic mRNAs with oligonbonucleotides," Gene, vol. 138:171-174 (1994).

Matsushima, Ayako et al., "Modification of *E. coli* Asparaginase with 2.4-Bis(O-Methoxypolyethylene Glycol)-6-Chloro-S-Triazine(Activated PEG2); Disapperance of Binding Ability Towards Anti-serum and Retention of Enzymic Activity," Chemistry Letters, pp. 773-776 (1980).

Mattheakis, Larry C. et al., "An in vitro polysome display system for identifying ligands from very large peptide libraries," Proc. Natl. Acad. Sci. USA, vol. 91:9022-9026 (1994).

McCleod, D. Scott et al., "Localization of VEGF Receptor-2 (KDR/Flk-1) and Effects of Blocking It in Oxygen-Induced Retinopathy," Investigative Ophthalmology & Visual Science, vol. 43(2):474-482 (2002).

Mcconnell, Stephen J. et al., "Tendamistat as a Scaffold for Conformationally Constrained Phage Peptide Libraries," J. Mol. Biol., vol. 250:460-470 (1995).

Mcpherson, Michael et al., "Drug Receptor Identification from Multiple Tissues Using Cellular-Derived mRNA Display Libraries," Chemistry & Biology, vol. 9:691-698 (2002).

Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).

Meissner, Markus et al., "Suppression of VEGFR2 Expression in Human Endothelial Cells by Dimethylfumarate Treatment: Evidence for Anti-Angiogenic Action," Journal of Investigative Dermatology, vol. 131:1356-1364 (2011).

Meyer, Rosana D. et al., "Comparative Structure-Function Analysis of VEGFR-1 and VEGFR-2, What Have We Learned from Chimeric Systems,?" Ann. N.Y. Acad. Sci., vol. 995:200-207 (2003).

Muller, Christoph W. et al., "Structure of the NF-kappaB p50 homodimer bound to DNA," Nature, vol. 373:311-317 (1995).

Muyldermans, Serge, "Single domain camel antibodies: current status," Reviews in Molecular Biotechnology, vol. 74:277-302 (2001).

(56) References Cited

OTHER PUBLICATIONS

Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).
Ng, Eugene W.M. et al., "Targeting angiogenesis, the underlying disorder in neovascular age-related macular degeneration," Can. J. Ophthalmol., vol. 40:352-368 (2005).
Ngo, J. Thomas et al., "Computational Complexity, Protein Structure Prediction, and The Levinthal Paradox," The Protein Folding Problem and TErtiary Structure Prediction, Merz, K. (Ed.), Birkhauser, Boston, Chapter 14, pp. 491-495 (1994).
Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Research, vol. 22(25):5530-5539 (1994).
Nilsen, Timothy W., "Trans-Splicing in Protozoa and Helminths," Infections Agents and Disease, vol. 1:212-218 (1992).
Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).
Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).
Bae, Dong-Goo et al., "Arginine-rich Anti-vascular Endothelial Growth Factor Peptides Inhibit Tumor Growth and Metastasis by Blocking Angiogenesis," The Journal of Biological Chemistry, vol. 275(18):13588-13596 (2000).
Baggio, Rick et al., "Identification of epitope-like consensus motifs using mRNA display," Journal of Molecular Recognition, vol. 15:126-134 (2002).
Baron, Martin et al., "H NMR Assignment and Secondary Structure of the Cell Adhesion Type III Module of Fibronectin," Biochemistry, vol. 31:2068-2073 (1992).
Baron, Martin et al., "Protein modules," TIBS, vol. 16:13-17 (1991).
Batori, Vincent et al., "Exploring the potential of the monobody scaffold: effects of loop elongation on the stability of a fibronectin type III domain," Protein Engineering, vol. 15(12):1015-1020 (2002).
Bianchi, Elisabetta et al., "High Level Expression and Rational Mutagenesis of a Designed Protein, the Minibody," J. Mol. Biol., vol. 236:649-659 (1994).
Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).
Boldicke, Thomas et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells from Cord Blood," Stem Cells, vol. 19:24-36 (2001).
Bork, P. et al. "The Immunoglobulin Fold, Structural Classification, Sequence Patterns and Common Core," J. Mol. Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 89:8990-8994 (1992).
Bork, Peer, "Powers and Pitfalls in Sequence Analysis: The 70% Hurdle," Genome Research, vol. 10:398-400 (2000).
Brenchley, P.E.C. et al., "Angiogenesis in inflammatory joint disease: a target for therapeutic intervention," Clin. Exp. Immunol., vol. 121:426-429 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Brown, McKay et al., "Tolerance to Single, but Not Multiple, Amino Acid Replacements in Antibody VH CDR2," The Journal of Immunology, vol. 156:3285-3291 (1996).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Carvalho, Jozelio Freire et al., "Vascular Endothelial Growth Factor (VEGF) in Autoimmune Diseases," Journal of Clinical Immunology, vol. 27(3):246-256 (2007).
Choy, E.H.S. Efficacy of a novel PEGylated humanized anti-TNF fragment (CDP870) in patients with rheumatoid arthritis: a phase II double-blinded, randomized, dose-escalating trial, Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Claffey, Kevin P. et al., "Vascular Endothelial Growth Factor, Regulation by Cell Differentiation and Activated Second Messenger Pathways," The Journal of Biological Chemistry, vol. 267(23):16317-16323 (1992).
Clarke, Jane et al., "Folding and Stability of a Fibronectin Type III Domain of Human Tenascin," J. Mol. Biol., vol. 270:771-778 (1997).
Connelly, Roberta J. et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu, et al., "Fibronectin Type III Domain Based Monobody with High Affinity," Biochemistry, vol. 46:12656-12664 (2007).
Ely, Kathryn R. et al., "Common molecular scaffold for two unrelated RGD molecules," Protein Engineering, vol. 8(8):823-827 (1995).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Abstract 2586: Adnectins as a platform for multi-specific targeted biologics: A novel bispecific inhibitor of EGFR and IGF-IR growth factor receptors," Cancer Research, vol. 70(8): Suppl. 1 (2010).

(56) References Cited

OTHER PUBLICATIONS

Emanuel, Stuart L. et al., "Functional activity of a bispecific Adnectin inhibitor to EGFR and IGFR," 2009 AACR Annual Meeting, Session Title: IGF-IR and PI3K Pathways, Abstract No. 2813, 2 pages (2009).

European Office Action for Application No. 06013825.2, 9 pages, dated Sep. 17, 2008.

European Office Action for Application No. 09167669.2, 7 pages, dated Dec. 28, 2009.

European Office Action for Application No. 11731571.3, 5 pages, dated Feb. 27, 2014.

European Search Report for Application No. 14168988.5, 7 pages, dated Oct. 7, 2014.

Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).

Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).

GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages (1996).

GenBank Accession No. CAA26536, Kornblihtt, A.R. et al., "Primary structure of human fibronectin: differential splicing nay generate at least 10 polypeptides from a single gene," EMBO J., vol. 4(7):1755-1759 (1985), 7 pages (1996).

Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).

Zhou, Tianhong et al., "Development of a multi-drug delivery implant for intraocular management of proliferative vitreoretinopathy," Journal of Controlled Release, vol. 55:281-295 (1998).

Zhu, Z. et al., "Inhibition of human leukemia in an animal model with human antibodies directed against vascular endothelial growth factor receptor 2. Correlation between antibody affinity and biological activity," Leukemia, vol. 17:604-611 (2003).

Rottgen, Peter et al., "A human pancreatic secretory trypsin inhibitor presenting a hyperveriable highly constrained epitope via monovalent phagemid display," Gene, vol. 164:243-250 (1995).

Rudikoff, Stuart et al., "Single amino acid substitution altering antigen-binding specificity," Proc. Natl. Acad. Sci. USA, vol. 79:1979-1983 (1982).

Schildbach, Joel F. et al., "Contribution of a single heavy chain residue to specificity of an anti-digoxin monoclonal antibody," Protein Science, vol. 3:737-749 (1994).

Schildbach, Joel F. et al., "Heavy Chain Position 50 Is a Determination of Affinity and Specificity for the Anti-digoxin Antibody 26-10," The Journal of Biological Chemistry, vol. 268(29):21739-21747 (1993).

Scott, Jamie K. et al., "Searching for Peptide Ligands with an Epitope Library," Science, vol. 249:386-390 (1990).

Shibata, K. et al., "An attempt to substitute the cell binding domain of human fibronectin in lambda phage J protein: Computer design and expression," Biochimie, vol. 75:459-465 (1993).

Shibuya, Masabumi, "Vascular endothelial growth factor receptor-2: Its unique signaling and specific ligand, VEGF-E," Cancer Sci., vol. 94(9):751-756 (2003).

Shima, David T. et al., "The Mouse Gene for Vascular Endothelial Growth Factor," The Journal of Biological Chemistry, vol. 271(7):3877-3883 (1996).

Skolnick, Jeffrey et al., "From genes to protein structure and function: novel application of computational approaches in the genomic era," Tibtech, vol. 18:34-39 (2000).

Smith, George P. et al., "Phage Display," Chem. Rev., vol. 97:391-410 (1997).

Smith, Temple et al., "The challenges of genome sequence annotation or 'The devil is in the details,'" Nature Biotechnology, vol. 15:1222-1223 (1997).

Supplementary European Search Report for Application No. 01913159.8, 3 pages, dated Dec. 21, 2004.

Supplementary European Search Report for Application No. 99967261.1, 3 pages, dated Mar. 6, 2002.

Takahashi, Satoru, "Vascular Endothelial Growth Factor (VEGF), VEGF Receptors and Their Inhibitors for Antiangiogenic Tumor Therapy," Biol. Pharm. Bull. vol. 34(12):1785-1788 (2011).

Tang, Lisa et al., "Pharmacokinetic Aspects of Biotechnology Products," Journal of Pharmaceutical Sciences, vol. 93(9):2184-2204 (2004).

Tischer, Edmund et al., "The Human Gene for Vascular Endothelial Growth Factor," The Journal of Biological Chemistry, vol. 266(18):11947-11954 (1991).

Tokuriki, Nobuhiko et al., "Stability effects of mutations and protein evolvability," Current Opinion in Structural Biology, vol. 19:596-604 (2009).

Tramontano, Anna et al., "The Making of the Minibody: an Engineered beta-Protein for the Display of Conformationally Constrained Peptides," Journal of Molecular Recognition, vol. 7:9-24 (1994).

Trinh, Ryan et al., "Optimization of codon pair use within the (GGGGS)3 linker sequence results in enhanced protein expression," Molecular Immunology, vol. 40:717-722 (2004).

Verheul, H.M.W. et al., "Targeting Vascular Endothelial Growth Factor Blockade: Ascites and Pleural Effusion Formation," The Oncologist, vol. 5(Suppl. 1):45-50 (2000).

Vuento, Matti et al., "Purification of Fibronectin from Human Plasma by Affinity Chromatography under Non-Denaturing Conditions," Biochem. J., vol. 183:331-337 (1979).

Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).

Watanabe, H. et al., "Anti-vascular endothelial growth factor receptor-2 (Flk-1/KDR) antibody suppresses contact hypersensitivity," Experimental Dermatology, vol. 13:671-681 (2004).

Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).

Wells, James A., "Additivity of Mutational Effects in Proteins," Biochemistry, vol. 29(37):8509-8517 (1990).

Williams, Alan F. et al., "The Immunoglobulin Superfamily—Domains for Cell Surface Recognition," Ann. Rev. Immunol., vol. 6:381-405 (1988).

Williams, Michael J. et al., "Solution Structures of Modular Proteins by Nuclear Magnetic Resonance," Methods in Enzymology, vol. 245:451-469 (1994).

Wilson, David S. et al., "The use of mRNA display to select high-affinity protein-binding peptides," PNAS, vol. 98 (7):3750-3755 (2001).

Written Opinion for Application No. PCT/US01/06414, 5 pages, dated Feb. 7, 2002.

Xiang, Jim et al., "Study of B72.3 combining sites by molecular modeling and site-directed mutagenesis," Protein Engineering, vol. 13(5):339-344 (2000).

Xu, Lihui et al., "Directed Evolution of High-Affinity Antibody Mimics Using mRNA Display," Chemistry & Biology, vol. 9:933-942 (2002).

Yang, Karen et al., "Tailoring structure-function and pharmacokinetic properties of single-chain Fv proteins by site-specific PEGylation," Protein Engineering, vol. 16(10):761-770 (2003).

Yoshiji, H. et al., "Vascular endothelial growth factor and receptor interaction is a prerequisite for murine hepatic fibrogenesis," Gut, vol. 52:1347-1354 (2003).

GenBank Accession No. P07589, Skorstengaard, K. et al., "Complete primary structure of bovine plasma fibronectin," Eur. J. Biochem., vol. 161(2):441-453 (1986), 9 pages (1997).

(56) References Cited

OTHER PUBLICATIONS

GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages (1996).
Ghosh, Gourisankar et al., "Structure of NF-kappaB p50 homodimer bound to a kappaB site," Nature, vol. 373:303-310 (1995).
Gill, Davinder S. et al., "Biopharmaceutical drug discovery using novel protein scaffolds," Current Opinion in Biotechnology, vol. 17:653-658 (2006).
Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth FIII Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hey, Thomas et al., "Artificial, non-antibody binding proteins for pharmaceutical and industrial applications," Trends in Biotechnology, vol. 23(10):514-522 (2005).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Huang, Fei et al., "The Mechanisms of Differential Sensitivity to an Insulin-like Growth Factor-1 Receptor Inhibitor (BMS-536924) and Rationale for Combining with EGFR/HER2 Inhibitors," Cancer Res., vol. 69(1):161-170 (2009).
Huang, Hu et al., "Blockade of VEGFR1 and 2 Suppresses Pathological Angiogenesis and Vascular Leakage in the eye," PLoS One, vol. 6(6):e21411, 14 pages, doi:10.1371/journal.pone.0021411 (2011).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2009/065765, 12 pages, dated May 24, 2011.
International Preliminary Report on Patentability and Written Opinion for Application No. PCT/US2011/034998, 10 pages, dated Nov. 6, 2012.
International Preliminary Report on Patentability and Written Opinion for Application No. PCT/US2011/038013, 9 pages, dated Nov. 27, 2012.
International Preliminary Report on Patentability for Applicaiton No. PCT/US2004/040885, 6 pages, dated Jun. 7, 2006.
International Preliminary Report on Patentability for Application No. PCT/US2011/038013, 9 pages, dated Nov. 27, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US04/40885, 3 pages, dated Feb. 21, 2006.
International Search Report for Application No. PCT/US2009/003192, 8 pages, dated Jun. 1, 2010.
International Search Report for Application No. PCT/US2009/065765, 7 pages, dated Apr. 23, 2010.
International Search Report for Application No. PCT/US2011/034998, 5 pages, dated Jul. 17, 2012.
International Search Report for Application No. PCT/US2011/038013, 7 pages, dated Jan. 25, 2012.
International Search Report for Application No. PCT/US99/29317, 2 pages, dated Apr. 6, 2000.
Jain, Rakesh K. et al., "Dissecting Tumour Pathophysiology Using Intravital Microscopy," Nature, vol. 2:266-276 (2002).
Jakob, W. et al., "The chick embryo chorioallantoic membrane as a bioassay for angiogenesis factors: Reactions induced by carrier materials," Exp. Path. Bd., vol. 15:241-249 (1978).
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. ARndt (Ed.), Humana Press, Totowa, NJ, Chapter 6, pp. 95-109 (2007).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).
Kussie, Paul H. et al., "A Single Engineered Amino Acid Substitution Changes Antibody Fine Specificity," Journal of Immunology, vol. 152:146-152 (1994).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Nord, Karin et al., "A combinatorial library of an alpha-helical bacterial receptor domain," Prot. Eng., vol. 8:601-608 (1995).

(56) References Cited

OTHER PUBLICATIONS

Nord, Karin et al., "Binding proteins selected from combinatorial libraries of an alpha-helical bacterial receptor domain," Nature Biotechnology, vol. 15:772-777 (1997).
Notice of Opposition to European Pat. No. 1137941 (Application No. 99 967 261.1), 29 pages, dated May 11, 2010.
Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Partial European Search Report for Application No. 01981621.4, 5 pages, dated Feb. 25, 2005.
Patel, Neela et al., "A Selective and Oral Small Molecule Inhibitor of Vascular Epithelial Growth Factor (VEGFR)-2 and VEGFR-1 Inhibits Neovascularization and Vascular Permeability," The Journal of Pharmacology and Experimental Therapeutics, vol. 306(3):838-845 (2003).
Phillips, Anthony J., "The challenge of gene therapy and DNA delivery," Journal of Pharmacy and Pharmacology, vol. 53:1169-1174 (2001).
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Posey, J. et al., "A Phase I Trial of an Anti-KDR (VEGFR2) Chimeric Antibody in Patients with Liver Metastases in Colorectal Cancer (CRC)," Slides from presentation at 2002 American Society of Clinical Oncology (ASCO) Annual Meeting, 20 pages, (2002).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Proescholdt, Martin A. et al., "Vascular Endothelial Growth Factor Is Expressed in Multiple Sclerosis Plaques and Can Induce Inflammatory Lesions in Experimental Allergic Encephalomyelitis Rats," Journal of Neuropathology and Experimental Neurology, vol. 61(10):914-925 (2002).
Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).

FIBRONECTIN BASED SCAFFOLD PROTEINS HAVING IMPROVED STABILITY

RELATED APPLICATIONS

This application is a continuation of U.S. patent application Ser. No. 13/699,458, filed Mar. 28, 2013 (now U.S. Pat. No. 9,562,089), which is a 35 U.S.C. 371 national stage filing of International Application No. PCT/US2011/038013, filed May 26, 2011, which claims the benefit of U.S. Provisional Application Nos. 61/348,647, filed May 26, 2010, and 61/348,663, filed May 26, 2010. The aforementioned applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Dec. 20, 2016, is named MXI_525USCN_Sequence_Listing.txt and is 43,886 bytes in size.

INTRODUCTION

Fibronectin based scaffolds are a family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins™ (Adnexus, a wholly owned subsidiary of Bristol-Myers Squibb).

Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperones, and carbohydrate-binding domains. For reviews see Bork & Doolittle, Proc Natl Acad Sci USA. 1992 Oct. 1; 89(19):8990-4; Bork et al., J Mol Biol. 1994 Sep. 30; 242(4):309-20; Campbell & Spitzfaden, Structure. 1994 May 15; 2(5):333-7; Harpez & Chothia, J Mol Biol. 1994 May 13; 238(4):528-39).

Fibronectin type III (Fn3) domains comprise, in order from N-terminus to C-terminus, beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. Any or all of loops AB, BC, CD, DE, EF and FG may participate in target binding. The BC, DE, and FG loops are both structurally and functionally analogous to the complementarity determining regions (CDRs) from immunoglobulins. U.S. Pat. No. 7,115,396 describes Fn3 domain proteins wherein alterations to the BC, DE, and FG loops result in high affinity TNFα binders, U.S. Publication No. 2007/0148126 describes Fn3 domain proteins wherein alterations to the BC, DE, and FG loops result in high affinity VEGFR2 binders.

Protein pharmaceuticals may be associated with physical and chemical instability during their production, purification, storage and delivery. These instability issues can adversely impact the biological properties associated with the protein therapeutic, thereby reducing the efficacy of that protein therapeutic. Sola, 2009, J. Pharm Sci, 98(4): 1223-1245. Accordingly, it would be advantageous to obtain improved fibronectin domain scaffold proteins that are associated with improved stability, e.g. reduced fragmentation and/or aggregation, that can be used for both therapeutic and diagnostic purposes.

SUMMARY

One aspect of the application provides for novel fibronectin based scaffold proteins that are associated with increased stability, including reduced fragmentation and/or reduced aggregation.

In some embodiments, the fibronectin based scaffold proteins provided herein comprise a fibronectin type III tenth ($^{10}$Fn3) domain, wherein the $^{10}$Fn3 domain comprises an amino acid sequence having at least 60% identity to SEQ ID NO: 1 and binds to a target molecule with a $K_D$ of less than. 100 nM, and wherein the $^{10}$Fn3 domain further comprises a C-terminal tail that does not contain a DK sequence. In exemplary embodiments, the C-terminal tail comprises the amino acid sequence of SEQ ID NO: 4. In some embodiments, the C-terminal tail further comprises a cysteine residue. In other embodiments, the C-terminal tail comprises the sequence of SEQ ID NO: 5.

In certain embodiments, the fibronectin based scaffold proteins bind to a target that is not bound by a wild-type $^{10}$Fn3 domain. In certain embodiments, fibronectin based scaffold proteins do not bind one or more of EGFR, human serum albumin or PCSK9. In certain embodiments, fibronectin based scaffold proteins that comprise a single $^{10}$Fn3 domain do not bind one or more of EGFR, human serum albumin or PCSK9. In certain embodiments, multivalent fibronectin based scaffold proteins do not bind to one or more of the following combinations of target molecules: i) EGFR and IGF-IR; ii) EGFR and any other target protein; or iii) human serum albumin and any other target protein.

In some embodiments, the $^{10}$Fn3 domains of the fibronectin based scaffold protein further comprises an N-terminal extension comprising from 1-10 amino acids. In other embodiments, the $^{10}$Fn3 domain of the fibronectin based scaffold protein comprises a sequence selected from the group consisting of: M, MG, G, and any of SEQ ID NOs: 19-21 and 26-31.

In some embodiments, the fibronectin based scaffold proteins further comprise a second $^{10}$Fn3 domain, wherein the second $^{10}$Fn3 domain comprises an amino acid sequence having at least 60% identity to SEQ ID NO: 1 and binds to a target molecule with a $K_D$ of less than 100 nM, and wherein the second $^{10}$Fn3 domain further comprises a C-terminal tail that does not contain a DK sequence. In exemplary embodiments, the second $^{10}$Fn3 domain comprises a C-terminal tail comprising the amino acid sequence of SEQ ID NO: 4. In some embodiments, the first and second $^{10}$Fn3 domains bind to different targets. In some embodiments, the second $^{10}$Fn3 domain further comprises an N-terminal extension comprising from 1-10 amino acids. In some embodiments, the N-terminal extension comprises a sequence selected from the group consisting of: M, MG, G, and any of SEQ ID NOs: 19-21 and 25-31. In some embodiments, the first and second $^{10}$Fn3 domains are connected by a polypeptide linker comprising from 1-30 amino acids. In some embodiments, the polypeptide linker is selected from the group consisting of: a glycine-serine based linker, a glycine-proline based linker, a proline-alanine linker and a Fn-based linker.

In certain embodiments, the fibronectin based scaffold protein comprises one or more $^{10}$Fn3 domains comprising a loop, AB; a loop, BC; a loop, CD; a loop, DE; loop, EF; and a loop, FG and each, independently, have at least one loop selected from loop BC, DE, and FG with an altered amino acid sequence relative to the sequence of the corresponding loop of the human $^{10}$Fn3 domain. In certain embodiments, the $^{10}$Fn3 domains comprise an amino acid sequence that is at least 50, 60, 70, or 80% identical to the naturally occurring human $^{10}$Fn3 domain represented by SEQ ID NO: 1. In an exemplary embodiment, the fibronectin based scaffold protein is a dimer comprising two $^{10}$Fn3 domains.

In another aspect, the application provides for novel fibronectin based scaffold protein dimers that are associated with reduced protein fragmentation as compared to the fibronectin based scaffold protein dimers described in PCT application WO2009/142773. In some embodiments, the fibronectin based scaffold protein dirtier comprises the amino acid sequence of SEQ ID NO: 48.

In another aspect, the application provides fibronectin based scaffold protein dimers having the structure N1-D1-C1-L-N2-D2-C2. In certain embodiment, N1 and N2 are optional N-terminal extensions independently comprising from 0-10 amino acids; D1 and D2 are independently selected from the group consisting of: (i) a tenth fibronectin type III domain ($^{10}$Fn3) domain having at least 95% identity with the amino acid sequence set forth in SEQ ID NO: 2, wherein said $^{10}$Fn3 domain binds to IGF-IR with a $K_D$ of less than 500 nM, and (ii) a $^{10}$Fn3 domain having at least 95% identity with the amino acid sequence set forth in SEQ ID NO: 3, wherein said $^{10}$Fn3 domain binds to VEGFR2 with a $K_D$ of less than 500 nM; L is a polypeptide linker comprising from 0-30 amino acid residues; C1 comprises the amino acid sequence set forth in SEQ ID NO: 4; and C2 comprises the amino acid sequence set forth in SEQ ID NO: 4, 5 or 6.

In some embodiments the fibronectin based scaffold protein dimers have the structure N1-D1-C1-L-N2-D2-C2, wherein D1 comprises a $^{10}$Fn3 domain having at least 95% identity with the amino acid sequence set forth in SEQ ID NO: 2, and D2 comprises a $^{10}$Fn3 domain having at least 95% identity with the amino acid sequence set forth in SEQ ID NO: 3. In other embodiments the fibronectin based scaffold protein dimers have the structure N1-D1-C1-L-N2-D2-C2, wherein D1 comprises a $^{10}$Fn3 domain having at least 95% identity with the amino acid sequence set forth in SEQ ID NO: 3, and D2 comprises a $^{10}$Fn3 domain having at least 95% identity with the amino acid sequence set forth in SEQ ID NO: 2.

In some embodiments, the fibronectin based scaffold protein dimers have the structure N1-D1-C1-L-N2-D2-C2, wherein C2 comprises the amino acid sequence of SEQ ID NO: 6.

In some embodiments, the fibronectin based scaffold protein dimers have the structure N1-D1-C1-L-N2-D2-C2, wherein N1 comprises an amino acid sequence selected from the group consisting of: M, MG, G, and any one of SEQ NOs: 19-21 and 26-31. In exemplary embodiments, N1 comprises the amino acid sequence of SEQ ID NO: 19. In some embodiments, the fibronectin based scaffold protein dimers have the structure N1-D1-C1-L-N2-D2-C2, wherein N2 comprises an amino acid sequence selected from the group consisting of: M, MG, G, and any one of SEQ ID NOs: 19-21 and 26-31. In exemplary embodiments, N2 comprises the amino acid sequence of SEQ ID NO: 20.

In some embodiments, the fibronectin based scaffold protein dimers have the structure N1-D1-C1-L-N2-D2-C2, wherein L is a polypeptide linker selected from the group consisting of: a glycine-serine based linker, a glycine-proline based linker, a proline-alanine linker and a Fn-based linker. In other embodiments, L comprises the amino acid sequence of SEQ ID NO: 7.

In some embodiments, the fibronectin based scaffold proteins further comprise one or more pharmacokinetic (PK) moieties selected from: a polyoxyalkylene moiety, a human serum albumin binding protein, sialic acid, human serum albumin, transferrin, IgG, an IgG binding protein, and an Fe fragment. In some embodiments, the PK moiety is a polyoxyalkylene moiety and said polyoxyalkylene moiety is polyethylene glycol (PEG). In some embodiments, the PEG moiety is covalently linked to the fibronectin based scaffold protein via a Cys or Lys amino acid. In some embodiments, the PEG is between about 0.5 kDa and about 100 kDa.

In one aspect, the application provides pharmaceutically acceptable compositions comprising a fibronectin based scaffold protein. In some embodiments, the composition is essentially pyrogen free. In some embodiments, the composition is substantially free of microbial contamination making it suitable for in vivo administration. The composition may be formulated, for example, for IV, IP or subcutaneous administration. In some embodiments, the composition comprises a physiologically acceptable carrier. In some embodiments, the pH of the composition is between 4.0-6.5. In some embodiments, the pH of the composition is between 4.0-5.5. In other embodiments, the pH of the composition is 5.5. In other embodiments, the pH of the composition is 4.0. In some embodiments, the concentration of the fibronectin based scaffold protein is 5 mg/ml in the composition.

In another aspect, the application provides a pharmaceutical formulation comprising a fibronectin based scaffold protein, wherein the formulation comprises at least 5 mg/ml of the fibronectin based scaffold protein, has a pH of 4.0, and is suitable for intravenous administration. In some embodiments, the pharmaceutical formulation is stable for at least 4 weeks at 25° C. In some embodiments, the pharmaceutical formulation has less than 4% fragmentation. In some embodiments, the formulation has less than 4% aggregates.

In another aspect, the application provides a method for treating a hyperproliferative disorder in a subject comprising administering to a subject in need thereof a therapeutically effective amount of any of the compositions as described herein.

In another aspect, the application provides a nucleic acid encoding a fibronectin based scaffold protein as described herein. Vectors containing polynucleotides for such proteins are included as well. Suitable vectors include, for example, expression vectors. A further aspect of the application provides for a cell, comprising a polynucleotide, vector, or expression vector, encoding a fibronectin based scaffold protein. Sequences are preferably optimized to maximize expression in the cell type used. In some embodiments, expression is in a bacterial cell. In other embodiments, expression is in a mammalian cell. Preferably, expression is in *E. coli*. In one aspect, the cell expresses a fibronectin based scaffold protein. In one aspect, the polynucleotides encoding fibronectin based scaffold proteins are codon optimized for expression in the selected cell type. Also provided are methods for producing a fibronectin based scaffold protein as described herein, comprising culturing a host cell comprising a nucleic, vector, or expression vector, comprising a nucleic acid encoding the fibronectin based scaffold protein and recovering the expressed fibronectin based scaffold protein from the culture.

DETAILED DESCRIPTION

Definitions

Figure 1:
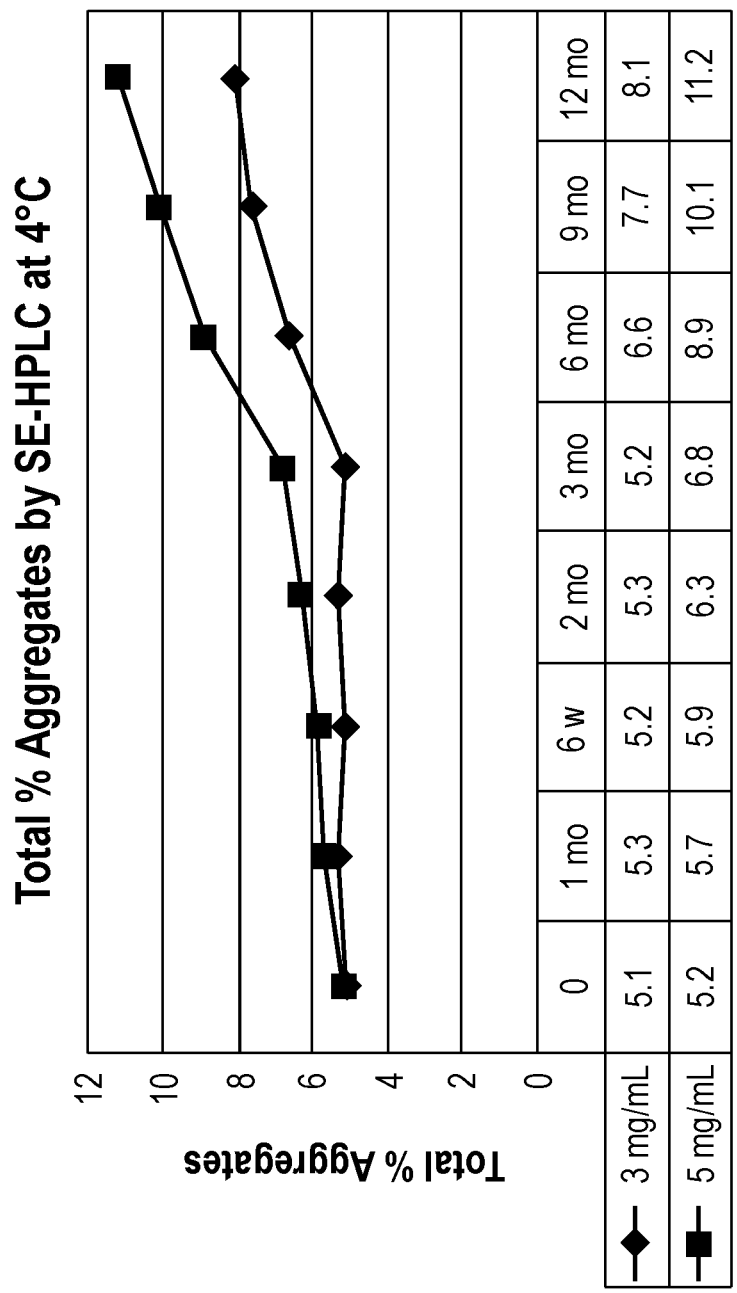
FIG. 1. Size exclusion-high pressure liquid chromatography (SE-HPLC) data showing the amount of protein aggregation over time for two concentrations of pegylated V/I (DK+) (SEQ ID NO: 22). The pegylated protein was stored at 4° C. for 12 months in 10 mM succinic acid, 5% sorbitol, pH 5.5 at 3 mg/mL protein concentration.
Figure 2:
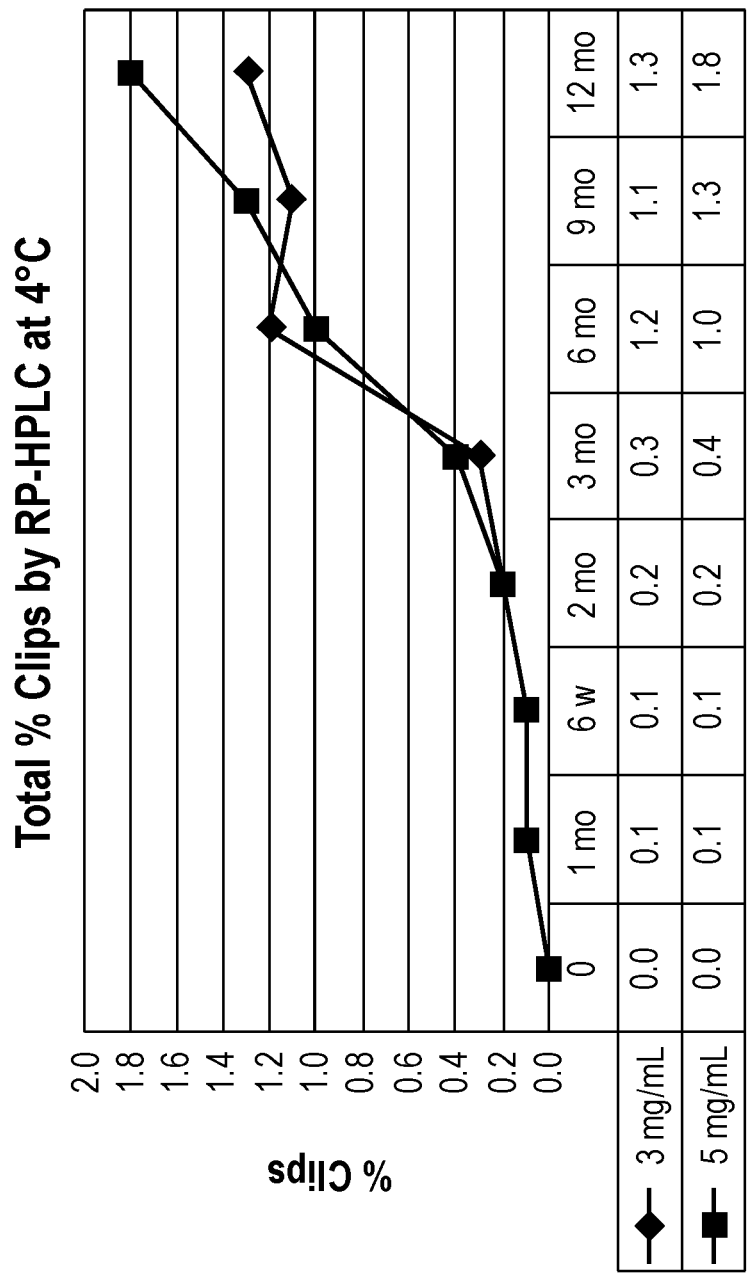
FIG. 2. SE-HPLC data showing the amount of protein fragmentation over time for two concentrations of pegylated V/I(DK+) (SEQ ID NO: 22). The pegylated protein was stored at 4° C. for 12 months in 10 mM succinic acid, 5% sorbitol, pH 5.5 at 3 mg/mL protein concentration.
Figure 3:
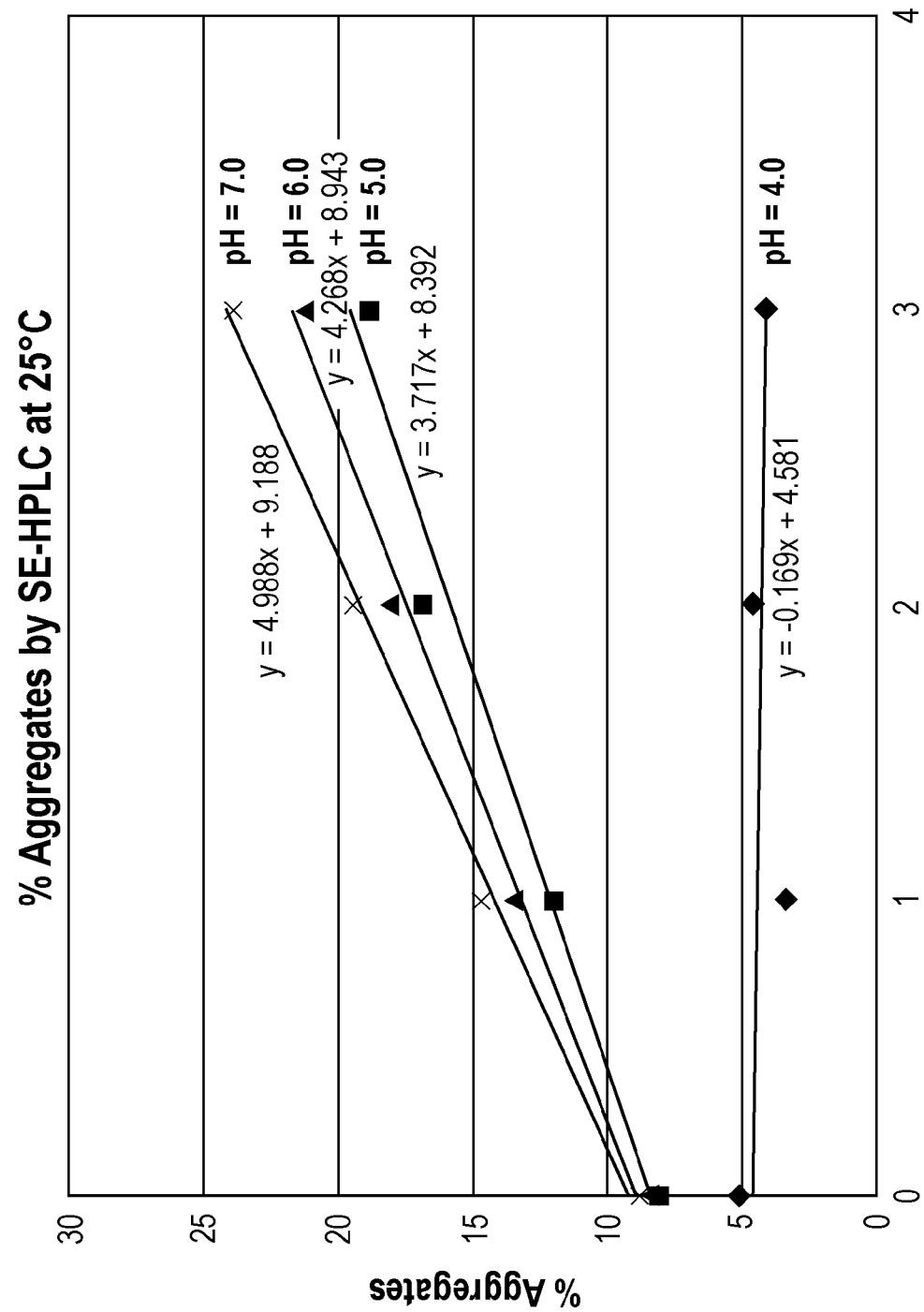
FIG. 3. SE-HPLC data showing the effect of pH on protein aggregation over time for pegylated V/I(DK+) (SEQ ID NO: 22). The pegylated protein was stored at 25° C. for 3 weeks in a formulation containing 50 mM NaCl, with 20 mM sodium acetate (for pH 4 and 5) or 20 mM sodium phosphate (for pH 6 and 7).
Figure 4:
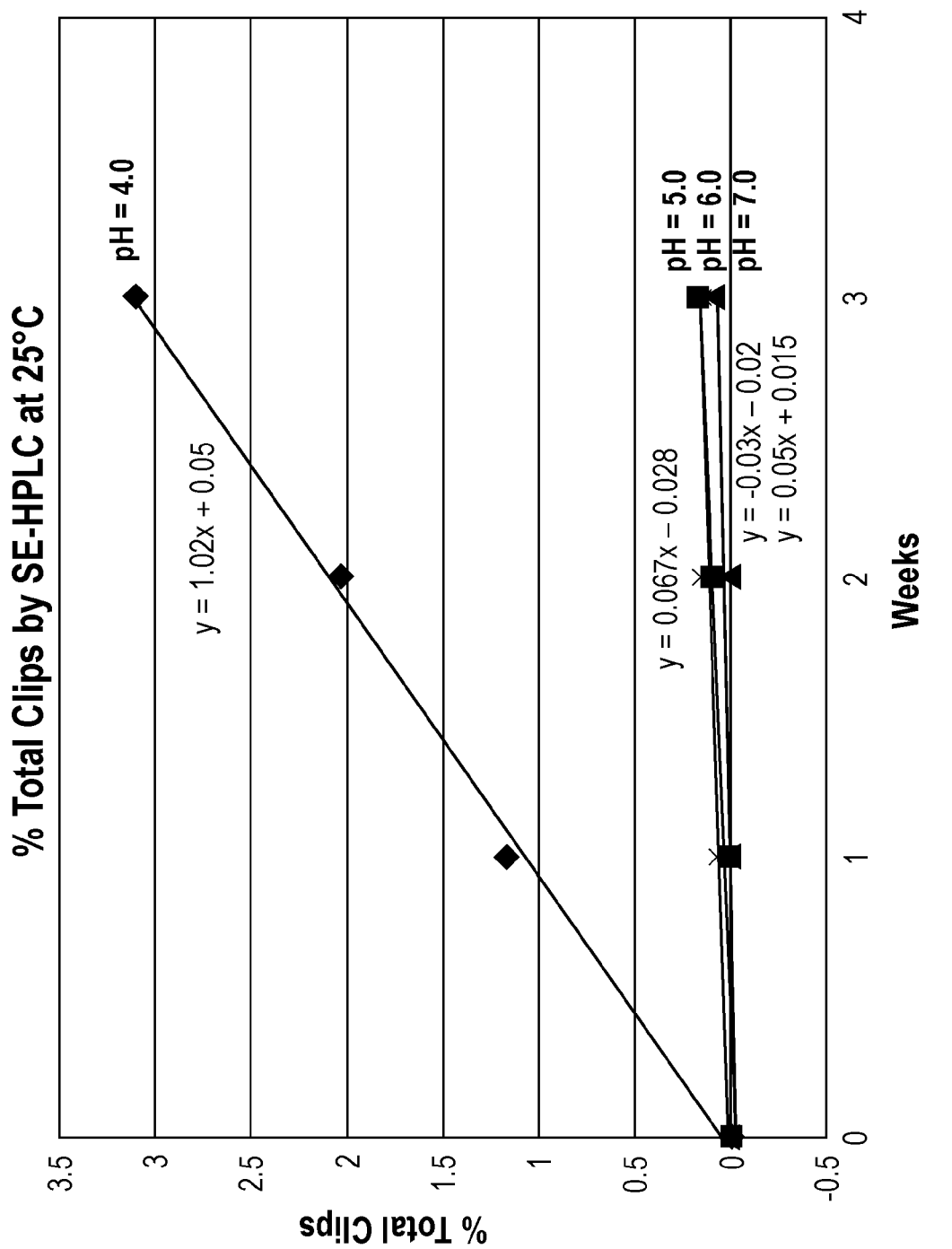
FIG. 4. SE-HPLC data showing the effect of pH on protein fragmentation over time for pegylated V/I(DK+) (SEQ ID NO: 22). The pegylated protein was stored at 25° C. for 3 weeks in a formulation containing 50 mM NaCl, with 20 mM sodium acetate (for pH 4 and 5) or 20 mM sodium phosphate (for pH 6 and 7).
Figure 5:
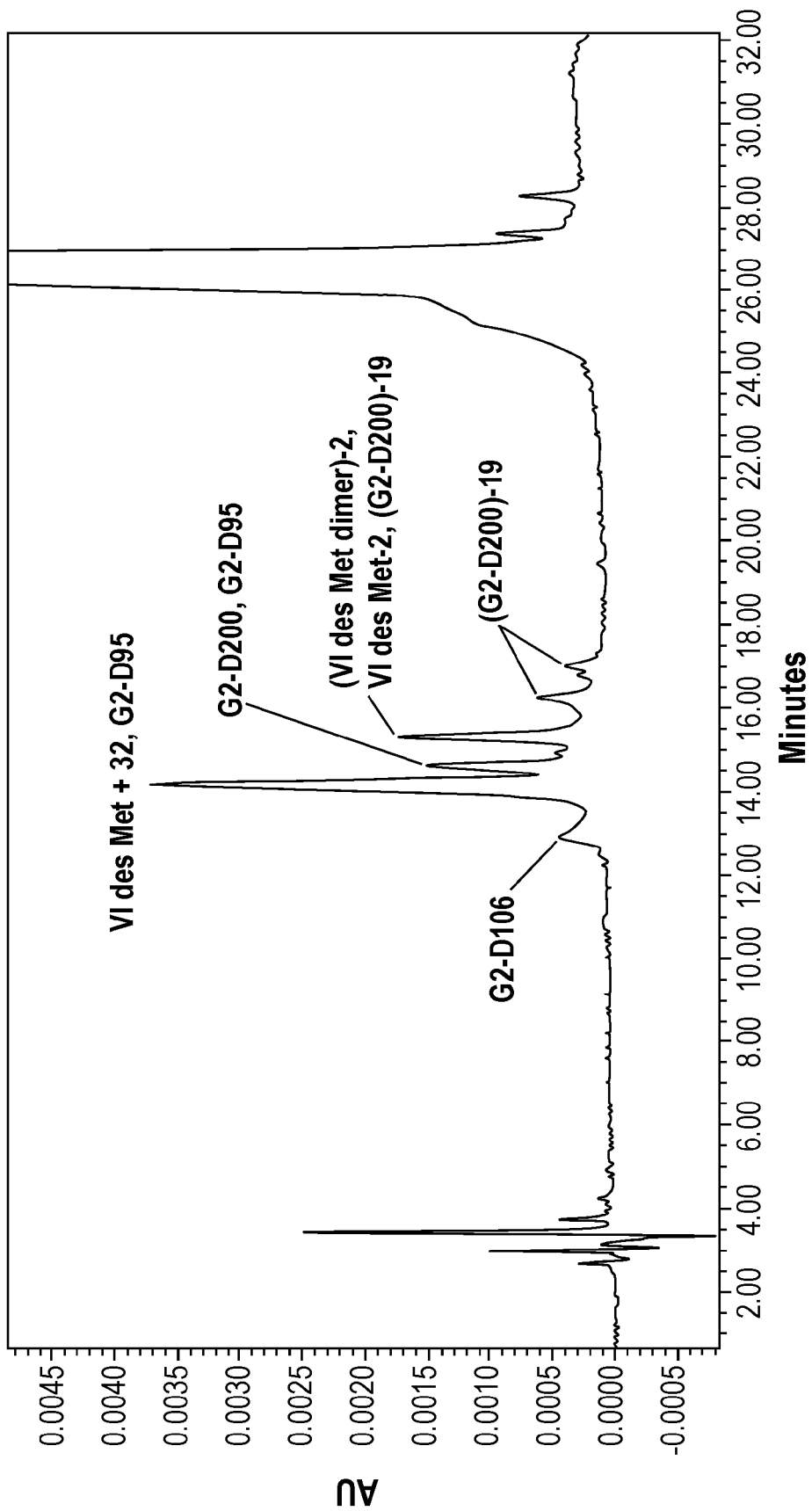
FIG. 5. Reverse phase-high pressure liquid chromatography (RP-HPLC) profile showing the sites of cleavage of pegylated V/I(DK+) molecule (SEQ ID NO: 22) after storage at 25° C. for 4 weeks in 10 mM acetate, 150 mM NaCl at pH 5.5. As indicated in the figure, protein cleavage occurs directly following positions D95, D106, D180 and D200, with cleavage predominantly occurring directly following sites D95 and D200. The pegylated protein was stored for 4 week at 25° C. in 10 mM sodium acetate, 150 mM sodium chloride, pH 5.5 at 5 mg/mL protein concentration.
Figure 6:
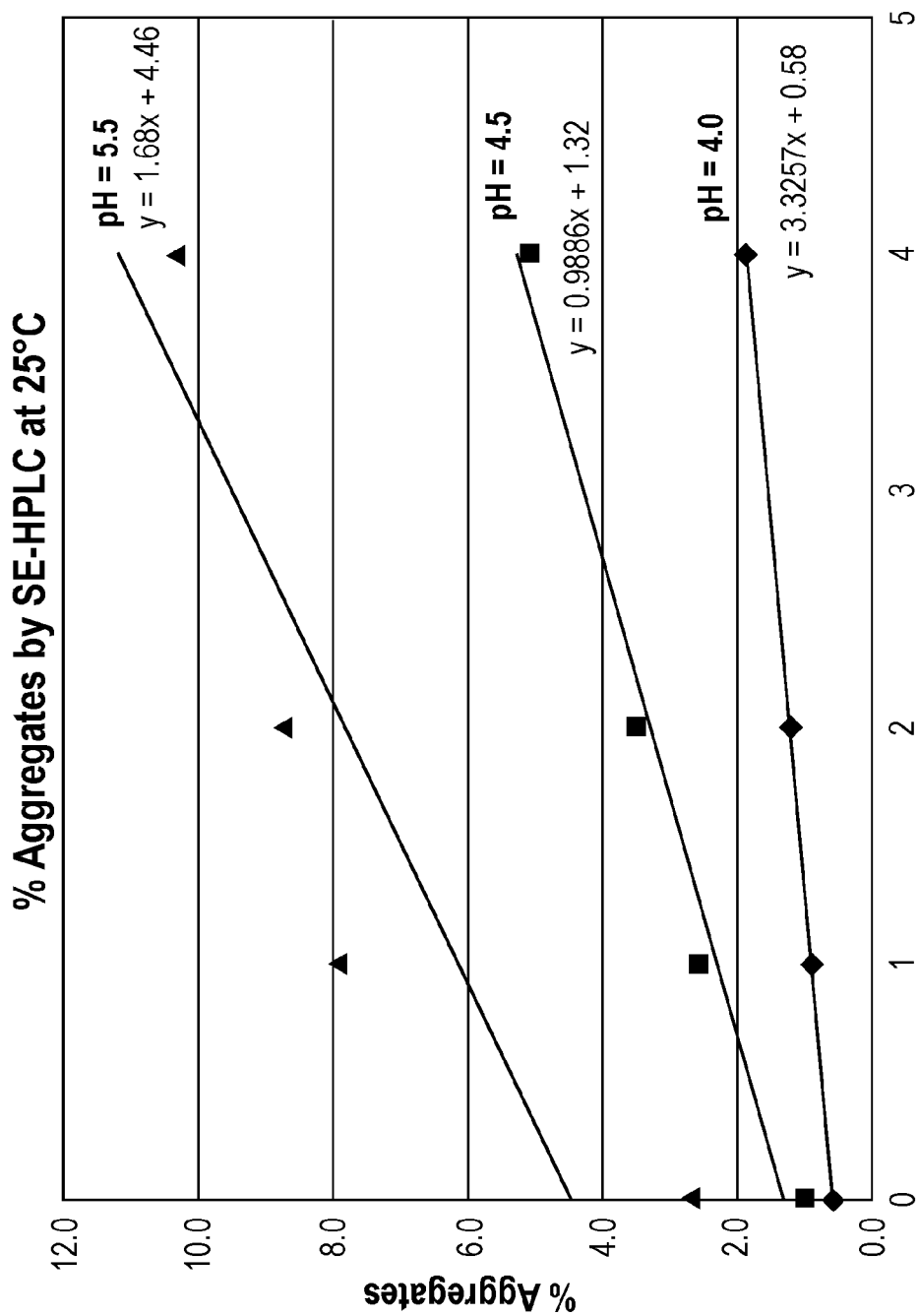
FIG. 6. SE-HPLC data showing the effect of pH on protein aggregation over time for the pegylated E/I(DK+) (SEQ ID NO: 23). The pegylated protein was stored for 4 week at 25° C. in 10 mM succinic acid, 5% sorbitol, pH 4.0, 4.5 and 5.5.

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y (where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs: inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The half-life of an amino acid sequence or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to the primate a suitable dose of the amino acid sequence or compound to be treated; collecting blood samples or other samples from said primate at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is for example made to the standard handbooks, such as Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd Rev. edition (1982).

Half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. An "increase in half-life" in particular refers to an increase in the t½-beta, either with or without an increase in the t½-alpha and/or the AUC or both.

Overview

The present application describes improved fibronectin based scaffold proteins that are associated with increased stability. The fibronectin based scaffold proteins described herein comprise one or more human tenth fibronectin type III domains that have been modified so as to bind to one or more desired targets. The present application also describes improved VEGFR2/IGF-IR bispecific fibronectin based scaffold protein dimers that are associated with increased stability, comprising two human tenth fibronectin type III domains, one that has been modified so as to bind specifically to VEGFR2 and one that has been modified so as to bind specifically to IGF-IR. PCT application WO 2009/142773 describes fibronectin scaffold multimers that may be linked covalently or non-covalently and that bind both VEGFR2 and IGF-IR. The present application relates, in part, to the surprising discovery that bispecific fibronectin based scaffold proteins that bind to VEGFR2 and IGF-IR experience a high frequency of fragmentation at certain aspartate residues. In particular, it has been discovered that aspartate residues directly followed by a lysine residue are more sensitive to cleavage in fibronectin based scaffold proteins as compared to aspartate residues followed by other amino acids. The application also relates to the surprising discovery that the degree of fragmentation of VEGFR2/IGF-IR binding fibronectin based scaffold proteins is considerably higher than the degree of fragmentation associated with a related fibronectin based scaffold protein, i.e., a bispecific EGFR/IGF-IR binding fibronectin based scaffold protein dimer, despite identical storage conditions and a high percentage of shared sequence identity between these similar proteins. The application also demonstrates that fragmentation of a model fibronectin based scaffold protein can be markedly reduced if the DK sites are removed or modified to substitute the aspartate residue for a different amino acid, e.g. glutamic acid. Also provided herein are improved compositions of fibronectin based scaffold proteins that have increased stability during storage.

Fibronectin Based Scaffolds

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand. A; a loop, AB; a beta or beta-like strand, B; a loop, BC; a beta or beta-like strand, C; a loop, CD; a beta or beta-like strand, L); a loop, DE; a beta or beta-like strand, E; a loop, EF; a beta or beta-like strand, F; a loop, FG; and a beta or beta-like strand, G. The seven antiparallel. β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the modules is low, they all share a high similarity in tertiary structure.

Adnectins™ (Adnexus, a Bristol-Myers Squibb Company) are ligand binding scaffold proteins based on the tenth fibronectin type III domain, i.e., the tenth module of Fn3, ($^{10}$Fn3). The amino acid sequence of the naturally occurring human $^{10}$Fn3 is set forth in SEQ ID NO: 37:

(SEQ ID NO: 37)
VSDVPRDLEVVAAT<u>PTSLLI</u>SWDAPAVTVRYYRITYGE<u>TGGNSPVQEFTV</u>

<u>PGSKSTATI</u>SGLKPGVDYTITVYAVTGRGDSPASSKPISINYRT (the AB, CD and EF loops are underlined, and the BC, FG, and DE loops are emphasized in bold).

In SEQ ID NO: 37, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. See e.g., Xu et al., Chemistry & Biology 2002 9:933-942. The BC, DE and FG loops align along one face of the molecule and the AB, CD and EF loops align along the opposite face of the molecule. In SEQ ID NO: 37, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the order: strand A, loop AB, strand B, etc. The first 8 amino acids of SEQ NO: 37 (italicized above) may be deleted while still retaining binding activity of the molecule. Residues involved in forming the hydrophobic core (the "core amino acid residues") in SEQ ID NO: 37 include the amino acids corresponding to the following amino acids of SEQ ID NO: 37: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 37. See e.g., Dickinson et al., J. Mol. Biol. 236: 1079-1092 (1994).

$^{10}$Fn3 domains are structurally and functionally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermostability properties as compared to antibodies, and they lack disulphide bonds, which are known to impede or prevent proper folding under certain conditions.

The BC, DE, and FG loops of $^{10}$Fn3 domains are analogous to the complementary determining regions (CDRs) from immunoglobulins. Alteration of the amino acid sequence in these loop regions changes the binding specificity of $^{10}$Fn3. $^{10}$Fn3 domains with modifications in the AB, CD and EF loops may also be made in order to produce a molecule that binds to a desired target. The protein sequences outside of the loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding. Methods for generating $^{10}$Fn3 ligand specific binders have been described in PCT Publication Nos. WO 00/034787, WO 01/64942, and WO 02/032925, disclosing high affinity TNFα binders, PCT Publication No. WO 2008/097497, disclosing high affinity VEGFR2 binders, PCT Publication No. WO 2008/066752, disclosing high affinity IGF-IR binders, and WO 2009/142773, disclosing high affinity multivalent VEGFR2/IGF-IR binders. Additional references discussing $^{10}$Fn3 binders and methods of selecting binders include PCT Publication Nos. WO 98/056915, WO 02/081497, and WO 2008/031098 and U.S. Publication No. 2003/0186385.

As described above, amino acid residues corresponding to residues 21-30, 51-56, and 76-87 of SEQ ID NO: 37 define the BC, DE and FG loops, respectively. However, it should be understood that not every residue within the loop region needs to be modified in order to achieve a $^{10}$Fn3 binding domain having strong affinity for a desired target, such as VEGFR2 or IGF-IR. For example, in some embodiments, only residues corresponding to amino acids 23-29 of the BC loop, 52-55 of the DE loop, and 77-86 of the FG loop were modified to produce high affinity $^{10}$Fn3 binders (see e.g., the VEGFR2 binding core having SEQ ID NO: 3). Accordingly, in certain embodiments, the BC loop may be defined by amino acids corresponding to residues 23-29 of SEQ ID NO: 37, the DE loop may be defined by amino acids corresponding to residues 52-55 of SEQ ID NO: 37, and the FG loop may be defined by amino acids corresponding to residues 77-86 of SEQ ID NO: 37.

Additionally, insertions and deletions in the loop regions may also be made while still producing high affinity $^{10}$Fn3 binding domains. For example, the FG loop of the VEGFR2 binder having SEQ ID NO: 3 has the same length FG loop as the wild-type $^{10}$Fn3 domain, i.e., the 10 residues 77-86 of SEQ ID NO: 37 were replaced with the ten residues 69-78 of SEQ ID NO: 3. In contrast, the FG loop of the IGF-IR binder having SEQ ID NO: 2 is shorter in length than the corresponding FG loop of the wild-type $^{10}$Fn3 domain, i.e., the 10 residues 77-86 of SEQ ID NO: 37 were replaced with the six residues 69-74 of SEQ ID NO: 2. Finally, the FG loop of the EGFR binder having SEQ ID NO: 39 is longer in length than the corresponding FG loop of the wild-type $^{10}$Fn3 domain, i.e., the 10 residues 77-86 of SEQ ID NO: 37 were replaced with the fifteen residues 69-83 of SEQ ID NO: 39.

Accordingly, in some embodiments, one or more loops selected from BC, DE, and FG may be extended or shortened in length relative to the corresponding loop in wild-type human $^{10}$Fn3. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding. In some embodiments, one or more residues of the integrin-binding motif "arginine-glycine-aspartic acid" (RGD) (amino acids 78-80 of SEQ ID NO: 37) may be substituted so as to disrupt integrin binding. In one embodiment, the RGD sequence is replaced by a polar amino acid-neutral amino acid-acidic amino acid sequence (in the N-terminal to C-terminal direction). In another embodiment, the RGD sequence is replaced with SGE.

The non-ligand binding sequences of $^{10}$Fn3, i.e., the "$^{10}$Fn3 scaffold", may be altered provided that the $^{10}$Fn3 domain retains ligand binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., Protein Eng. 2002 15(12):1015-20; Koide et al., Biochemistry 2001 40(34):10326-33.

The $^{10}$Fn3 scaffold may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. In certain embodiments, the scaffold may comprise anywhere from 0-1.5, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In exemplary embodiments, the scaffold modification preferably reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-35:2 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In one aspect, the application provides fibronectin based scaffold proteins, e.g., polypeptides comprising at least one $^{10}$Fn3 domain and having a C-terminal tail that lacks a DK sequence. In exemplary embodiments, the fibronectin based scaffold proteins comprise a $^{10}$Fn3 domain having a C-terminal tail comprising the amino acid sequence of SEQ ID NO: 4. Such fibronectin based scaffold proteins have improved stability relative to fibronectin based scaffolds containing one or more DK sequences.

In some embodiments, a fibronectin based scaffold protein comprises a $^{10}$Fn3 domain having at least 40%, 50%, 55%, 60%, 65%, 70%, 75%, 80%, 85%, or 90% identity to the human $^{10}$Fn3 domain having the amino acid sequence of SEQ ID NO: 1. Much of the variability will generally occur in one or more of the loops. Each of the beta or beta-like strands of a $^{10}$Fn3 domain in a fibronectin based scaffold protein may comprise, consist essentially of, or consist of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions. In exemplary embodiments, the $^{10}$Fn3 domain binds to a desired target with a $K_D$ of less than 500 nM, 100 nM, 1 nM, 500 pM, 100 pM or less. In exemplary embodiments, the fibronectin based scaffold protein binds specifically to a target that is not bound by a wild-type $^{10}$Fn3 domain, particularly the wild-type human $^{10}$Fn3 domain.

In some embodiments, the disclosure provides polypeptides comprising a $^{10}$Fn3 domain, wherein the $^{10}$Fn3 domain comprises a loop, AB: a loop, BC; a loop, CD; a loop, DE; a loop, EF; and a loop, FG; and has at least one loop selected from loop BC, DE, and FG with an altered amino acid sequence relative to the sequence of the corresponding loop of the human $^{10}$Fn3 domain. In some embodiments, the BC and FG loops are altered. In some embodiments, the BC, DE, and FG loops are altered, i.e., the $^{10}$Fn3 domain comprises non-naturally occurring loops. By "altered" is meant one or more amino acid sequence alterations relative to a template sequence (i.e., the corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of a $^{10}$Fn3 domain may be altered in length as well as in sequence to cover the CDR3 range of 4-28 residues to obtain the greatest possible flexibility and affinity in antigen binding.

In some embodiments, the fibronectin based scaffold protein comprises a $^{10}$Fn3 domain having an amino acid sequence at least 80, 85, 90, 95, 98, or 100% identical to the non-loop regions of SEQ ID NO: 1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions, or a combination thereof. In some embodiments, the FG loop has up to 12 amino acid substitutions, up to 11 amino acid deletions, up to 25 amino acid insertions, or a combination thereof.

In certain embodiments, the fibronectin based scaffold protein comprises a $^{10}$Fn3 domain that is defined generally by following the sequence:

(SEQ ID NO: 38)
EVVAATPTSLLISW(X)$_x$RYYRITYGETGGNSPVQEFTVP(X)$_y$TATISG
LKPGVDYTITVYAVT(X)$_z$PISINYRTEIEK

In SEQ ID NO: 38, the BC loop is represented by X$_x$, the DE loop is represented by X$_y$, and the FG loop is represented by X$_z$. X represents any amino acid and the subscript following the X represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 7 amino acids, y is 4 amino acids, and z is 6, 10 or 15 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 38. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 38. In certain embodiments, the core amino acid residues are fixed and any substitutions, conservative substitutions, deletions or additions occur at residues other than the core amino acid residues. The EIEK tail (SEQ ID NO: 4) shown in bold is fixed. In certain embodiments, the amino acids immediately flanking the loop regions (e.g., the non-underlined residues) may each independently be substituted or deleted. When substituting the residues immediately flanking the loops, each residues may be substituted with a sequence having the same number of amino acids or with a larger amino acid sequence (e.g., insertions of 0-10, 0-8, 0-5, 0-3, or 0-2 amino acid residues). The non-underlined residues are part of the loop region and therefore are amenable to substitution without significantly affecting the structure of the $^{10}$Fn3 domain.

The $^{10}$Fn3 domains generally begin with amino acid number 1 of SEQ ID NO: 37. However, domains with amino acid deletions are also encompassed by the invention. In some embodiments, the first eight amino acids of SEQ ID NO: 37 are deleted. Additional sequences may also be added to the N- or C-terminus of a $^{10}$Fn3 domain having amino acids corresponding to 1-94 of SEQ ID NO: 37 or amino acids 9-94 of SEQ ID NO: 37. For example, an additional MG sequence may be placed at the N-terminus of a $^{10}$Fn3 domain. The M will usually be cleaved off, leaving a G at the N-terminus. In some embodiments, the N-terminal extension consists of an amino acid sequence selected from the group consisting of: M, MG, G, and any of SEQ ID NOs: 19-21.

The $^{10}$Fn3 domain may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 19), VSDVPRDL (SEQ ID NO: 20), and GVSDVPRDL (SEQ ID NO: 21), or N-terminal truncations of any one of SEQ ID NOs: 19, 20 or 21. Other suitable N-terminal extensions include, for example, $X_n$SDVPRDL (SEQ ID NO: 26), $X_n$DVPRDL (SEQ ID NO: 27), $X_n$VPRDL (SEQ ID NO: 28), $X_n$PRDL (SEQ ID NO: 29), $X_n$RDL (SEQ ID NO: 30), $X_n$DL (SEQ ID NO: 31), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus.

The fibronectin based scaffold proteins provided herein comprise a $^{10}$Fn3 domain having a C-terminal tail sequence comprising the amino acid sequence of SEQ ID NO: 4. Exemplary C-terminal tails include polypeptides that are from 1-20, 1-15, 1-10, 1-8, 1-5, or 1-4 amino acids in length. Specific examples of tail sequences include, for example, polypeptides comprising, consisting essentially of, or consisting of, EIEK (SEQ ID NO: 4), EGSGC (SEQ ID NO: 5), EIEKPCQ (SEQ ID NO: 6), EIEKPSQ (SEQ ID NO: 32), EIEKP (SEQ ID NO: 33), EIEKPS (SEQ ID NO: 34), or EIEKPC (SEQ ID NO: 35). Such C-terminal sequences are referred to herein as tails or extensions and are further described herein. In exemplary embodiments, the C-terminal tail comprises, consists essentially of, or consists of the amino acid sequence of SEQ ID NO: 6. In preferred embodiments, the C-terminal sequences lack DK sequences. In exemplary embodiments, the C-terminal tail comprises a residue that facilitates modification by PEG, i.e., a lysine or cysteine residue. In preferred embodiments, the C-terminal tail lacks a DK sequence and comprises a cysteine residue.

In certain embodiments, the fibronectin based scaffold proteins comprise a $^{10}$Fn3 domain having both an N-terminal extension and a C-terminal tail. In some embodiments, a His6-tag may be placed at the N-terminus or the C-terminus.

In an exemplary embodiment, the fibronectin based scaffold protein comprises a $^{10}$Fn3 domain that binds to VEGFR2. In certain embodiments, the fibronectin based scaffold protein binds to VEGFR2 with a $K_D$ of less than 500 nM and the BC loop comprises the amino acid sequence of SEQ ID NO: 43, the DE comprises the amino acid sequence of SEQ ID NO: 44, the FG loop comprises the amino acid sequence of SEQ ID NO: 45, and the protein comprises a C-terminal tail that lacks a DK sequence. In exemplary embodiments, the C-terminal tail comprises EIEK (SEQ ID NO: 4), EGSGC (SEQ ID NO: 5), EIEKPCQ (SEQ ID NO: 6), EIEKPSQ (SEQ ID NO: 32), EIEKP (SEQ ID NO: 33), EIEKPS (SEQ ID NO: 34), or EIEKPC (SEQ ID NO: 35). In preferred embodiments, the C-terminal tail comprises EIEK (SEQ ID NO: 4) or EIEKPCQ (SEQ ID NO: 6).

In certain embodiments, the fibronectin based scaffold protein is a multivalent protein that comprises two or more $^{10}$Fn3 domains. For example, a multivalent fibronectin based scaffold protein may comprise 2, 3 or more $^{10}$Fn3 domains that are covalently associated. In exemplary embodiments, the fibronectin based scaffold protein is a bispecific or dimeric protein comprising two $^{10}$Fn3 domains. In certain embodiments, a multivalent fibronectin based protein scaffold comprises a first $^{10}$Fn3 domain that binds to a first target molecule and a second $^{10}$Fn3 domain that binds to a second target molecule. The first and second target molecules may be the same or different target molecules. When the first and second target molecules are the same, the $^{10}$Fn3 domains, i.e., the binding loops, may be the same or different. Therefore, the first and second $^{10}$Fn3 domains may bind to the same target but at different epitopes.

In exemplary embodiments, each $^{10}$Fn3 domain of a multivalent fibronectin based protein scaffold binds to a desired target with a $K_D$ of less than 500 nM, 100 nM, 1 nM, 500 pM, 100 pM or less. In exemplary embodiments, each $^{10}$Fn3 domain of a multivalent fibronectin based protein scaffold binds specifically to a target that is not bound by a wild-type $^{10}$Fn3 domain, particularly the wild-type human $^{10}$Fn3 domain.

The $^{10}$Fn3 domains in a multivalent fibronectin based scaffold protein may be connected by a polypeptide linker. Exemplary polypeptide linkers include polypeptides having from 1-20, 1-15, 1-10, 1-8, 1-5, 1-4, 1-3, or 1-2 amino acids. Specific examples of suitable polypeptide linkers are described further herein. In certain embodiments, the linker may be a C-terminal tail polypeptide as described herein, an N-terminal extension polypeptide as described herein, a linker polypeptide as described below, or any combination thereof.

In the case of multivalent fibronectin based scaffold proteins, preferably none of the $^{10}$Fn3 domains comprise a C-terminal tail containing a DK sequence. In exemplary embodiments, a multivalent fibronectin based scaffold protein comprises two or more $^{10}$Fn3 domains, wherein each domain comprises a C-terminal tail that does not contain a DK sequence. In certain embodiments, a multivalent fibronectin based scaffold protein comprises two or more $^{10}$Fn3 domains, wherein each domain comprises a C-terminal tail that does not contain a DK sequence and does contain a residue suitable for addition of a PEG moiety, such as a lysine or cysteine residue. In certain embodiments, a multivalent fibronectin based scaffold protein comprises two or more $^{10}$Fn3 domains, wherein each domain comprises a C-terminal tail comprising the amino acid sequence of SEQ ID NO: 4. In certain embodiments, a multivalent fibronectin based scaffold protein comprises two or more $^{10}$Fn3 domains, wherein the N-terminal $^{10}$Fn3 domain comprises a C-terminal tail comprising the amino acid sequence of SEQ ID NO: 4 and the C-terminal $^{10}$Fn3 domain comprises a C-terminal tail comprising the amino acid sequence of EIEK (SEQ ID NO: 4), EGSGC (SEQ ID NO: 5), EIEKPCQ (SEQ ID NO: 6), EIEKPSQ (SEQ ID NO: 32). EIEKP (SEQ ID NO: 33), EIEKPS (SEQ ID NO: 34), or EIEKPC (SEQ ID NO: 35).

By varying the loop sequences of the 10Fn3 domain, it is possible to generate a fibronectin based scaffold protein that binds to any desired target. In exemplary embodiments, the fibronectin based scaffold proteins provided herein having increased stability may bind to a therapeutically desirable target, such as, for example, TNFα, VEGFR2, IGF-IR, or EGFR. In certain embodiments, a fibronectin based scaffold protein does not bind to one or more of the following targets: EGFR, IGF-IR, HSA and PCSK9, or a fragment of any of the foregoing. In certain embodiments, a fibronectin based scaffold protein comprising a single $^{10}$Fn3 domain does not bind to one or more of the following targets: EGFR, IGF-IR, HSA and PCSK9, or a fragment of any of the foregoing. In certain embodiments, a fibronectin based scaffold protein comprising a single $^{10}$Fn3 domain does not bind to any of the following targets: EGFR, IGF-IR, HSA and PCSK9, or a fragment of any of the foregoing. In certain embodiments, a fibronectin based scaffold protein comprising two $^{10}$Fn3 domains does not bind one or more of the following targets: EGFR, IGF-IR, HSA and PCSK9, or a fragment of any of the foregoing. In certain embodiments, a fibronectin based scaffold protein comprising two $^{10}$Fn3 domains does not bind one or more of the following combinations of target molecules: i) EGFR and IGF-IR; ii) EGFR and any other target protein; or iii) human serum albumin and any other target protein. In certain embodiments, a fibronectin based scaffold protein comprising two $^{10}$Fn3 domains does not bind any of the following combinations of target molecules: i) EGFR and IGF-IR; ii) EGFR and any other target protein; or iii) human serum albumin and any other target protein.

Fibronectin Based Scaffold Protein Dimers

In certain embodiments, the fibronectin based scaffold proteins described herein are dimers comprising two $^{10}$Fn3 domains. In one embodiment, the application provides V/I fibronectin based scaffold protein dimers comprising a first and second $^{10}$Fn3 domain selected from the group consisting of: (i) a $^{10}$Fn3 domain comprising a BC loop having the amino acid sequence of SEQ ID NO: 40, a DE loop having the amino acid sequence of SEQ ID NO: 41, an FG loop having the amino acid sequence of SEQ ID NO: 42, and a C-terminal tail comprising the amino acid sequence of any one of SEQ ID NOs: 4-6, wherein the $^{10}$Fn3 domain binds IGF-IR; and (ii) a $^{10}$Fn3 domain comprising a BC loop having the amino acid sequence of SEQ ID NO: 43, a DE loop having the amino acid sequence of SEQ ID NO: 44, an FG loop having the amino acid sequence of SEQ ID NO: 45, and a C-terminal tail comprising the amino acid sequence of any one of SEQ ID NOs: 4-6, wherein the Fn3 domain binds VEGFR2. In exemplary embodiments, each of the VEGFR2 and IGF-IR binding $^{10}$Fn3 domains binds to its target with a $K_D$ of less than 500 nM, 100 nM, 1 nM, 500 pM, 100 pM or less.

In certain embodiments, the V/I fibronectin based scaffold protein dimer comprises in order from N-terminus to C-terminus an IGF-IR binding domain and a VEGFR2 binding domain. In exemplary embodiments, the fibronectin based scaffold protein dimer comprises: (i) a first $^{10}$Fn3 domain comprising a BC loop having the amino acid sequence of SEQ ID NO: 40, a DE loop having the amino acid sequence of SEQ ID NO: 41, an FG loop having the amino acid sequence of SEQ ID NO: 42, and a C-terminal tail comprising the amino acid sequence of SEQ ID NO: 4, wherein the $^{10}$Fn3 domain binds IGF-IR; and (ii) a second $^{10}$Fn3 domain comprising a BC loop having the amino acid sequence of SEQ ID NO: 43, a DE loop having the amino acid sequence of SEQ ID NO: 44, an FG loop having the amino acid sequence of SEQ ID NO: 45, and a C-terminal tail comprising the amino acid sequence of SEQ ID NO: 6, wherein the $^{10}$Fn3 domain binds VEGFR2. In exemplary embodiments, each of the VEGFR2 and IGF-IR binding $^{10}$Fn3 domains binds to its target with a $K_D$ of less than 500 nM, 100 nM, 1 nM, 500 pM, 100 pM or less.

In certain embodiments, the V/I fibronectin based scaffold protein dimer comprises in order from N-terminus to C-terminus a VEGFR2 binding domain and an IGF-IR binding domain. In exemplary embodiments, the fibronectin based scaffold protein dimer comprises: (i) a first $^{10}$Fn3 domain comprising a BC loop having the amino acid sequence of SEQ ID NO: 43, a DE loop having the amino acid sequence of SEQ ID NO: 44, an FG loop having the amino acid sequence of SEQ ID NO: 45, and a C-terminal tail comprising the amino acid sequence of SEQ ID NO: 4, wherein the $^{10}$Fn3 domain binds VEGFR2; and (ii) a second $^{10}$Fn3 domain comprising a BC loop having the amino acid sequence of SEQ ID NO: 40, a DE loop having the amino acid sequence of SEQ ID NO: 41, an FG loop having the amino acid sequence of SEQ ID NO: 42, and a C-terminal tail comprising the amino acid sequence of SEQ ID NO: 6, wherein the $^{10}$Fn3 domain binds IGF-IR; and In exemplary embodiments, each of the VEGFR2 and IGF-IR binding $^{10}$Fn3 domains binds to its target with a $K_D$ of less than 500 nM, 100 nM, 1 nM, 500 pM, 100 pM or less.

In certain embodiments, the V/I fibronectin based scaffold protein dimer comprises a first and second $^{10}$Fn3 domain selected from the group consisting of: (i) a $^{10}$Fn3 domain comprising, consisting essentially of, or consisting of an amino acid sequence having at least 90%, 95%, 97%, 98%, 99% or 100% identity with SEQ ID NO: 2, wherein the $^{10}$Fn3 domain comprises, consists essentially of, or consists of a C-terminal tail having the amino acid sequence of any one of SEQ ID NOs: 4-6, and wherein the $^{10}$Fn3 domain binds IGF-IR; and (ii) a $^{10}$Fn3 domain comprising, consisting essentially of, or consisting of an amino acid sequence having at least 90%, 95%, 97%, 98%, 99% or 100% identity with SEQ ID NO: 3, wherein the $^{10}$Fn3 domain comprises, consists essentially of, or consists of a C-terminal tail having the amino acid sequence of any one of SEQ ID NOs: 4-6, and wherein the $^{10}$Fn3 domain binds VEGFR2. In exemplary embodiments, each of the VEGFR2 and IGF-IR binding $^{10}$Fn3 domains binds to its target with a $K_D$ of less than 500 nM, 100 nM, 1 nM, 500 pM, 100 pM or less. In exemplary embodiments the first and second $^{10}$Fn3 domains are connected via a polypeptide linker. In certain embodiments, the V/I fibronectin based scaffold protein dimer comprises an N-terminal VEGFR2 binding $^{10}$Fn3 domain and a C-terminal IGF-IR binding $^{10}$Fn3 domain. In certain embodiments, the V/I fibronectin based scaffold protein dimer comprises an N-terminal IGF-IR binding $^{10}$Fn3 domain and a C-terminal VEGFR2 binding $^{10}$Fn3 domain. In certain embodiments, the N-terminal $^{10}$Fn3 domain comprises a C-terminal tail having the amino acid sequence of SEQ ID NO: 4 and the C-terminal $^{10}$Fn3 domain comprises a C-terminal tail having the amino acid sequence of SEQ ID NO: 6.

In certain embodiments, a V/I fibronectin based scaffold protein dimer comprises the amino acid sequence of any one of SEQ ID NOs: 48-55. In other embodiments, a V/I fibronectin based scaffold protein dimer comprises the amino acid sequence of SEQ ID NO: 48. In some embodiments, a V/I fibronectin based scaffold protein dimer comprises an amino acid sequence having at least 70, 75, 80, 85, 90, 95, 97, 98, 99 or 100% identity with the amino acid sequence of any one of SEQ ID NOs: 48-55.

In certain embodiments, a V/I fibronectin based scaffold protein dimer comprises a polypeptide having the structure N1-D1-C1-L-N2-D2-C2, wherein N1 and N2 are optional N-terminal extensions independently comprising from 0-10 amino acids, wherein D1 and D2 are independently selected from the group consisting of: (i) a tenth fibronectin type III domain ($^{10}$Fn3) domain having at least 90%, 95%, 97%, 98%, 99% or 100% identity with the amino acid sequence set forth in SEQ ID NO: 2, wherein said $^{10}$Fn3 domain binds to IGF-IR with a K) of less than 500 nM, 100 nM, 1 nM, 500 pM, 100 pM or less, and (ii) a $^{10}$Fn3 domain having at least 90%, 95%, 97%, 98%, 99% or 100% identity with the amino acid sequence set forth in SEQ ID NO: 3, wherein said $^{10}$Fn3 domain binds to VEGFR2 with a $K_D$ of less than 500 nM, 100 nM, 1 nM, 500 pM, 100 pM; wherein L is a polypeptide linker comprising from 0-30 amino acid residues; wherein C1 comprises, consists essentially of, or consists of the amino acid sequence of SEQ ID NO: 4; and wherein C2 comprises, consists essentially of, or consists of any one of the amino acid sequences of SEQ ID NOs: 4, 5 or 6. In certain embodiments, D1 binds to VEGFR2 and D2 binds to IGF-IR. In other embodiments, D binds to IGF-IR and D2 binds to VEGFR2.

In certain embodiments, the D1 or D2 region is a $^{10}$Fn3 domain that binds to VEGFR2 comprising a BC loop having the amino acid sequence of SEQ ID NO: 43, a DE loop having the amino acid sequence of SEQ ID NO: 44, and an FG loop having the amino acid sequence of SEQ ID NO: 45, wherein the $^{10}$Fn3 domain binds to VEGFR2 with a $K_D$ of less than 100 nM.

In certain embodiments, the D1 or D2 region is a VEGFR2 binder represented by the following amino acid sequence:

(SEQ ID NO: 3)
EVVAATPTSLLISWRHPHFPTRYYRITYGETGGNSPVQEFTVPLQPPTAT
ISGLKPGVDYTITVYAVTDGRNGRLLSIPISINYRT.

In SEQ ID NO: 3, the sequence of the BC, DE and FG loops have a fixed sequence as shown in bold (e.g., a BC loop having the amino acid sequence of SEQ ID NO: 43, a DE loop having the amino acid sequence of SEQ ID NO: 44, and an FG loop having the amino acid sequence of SEQ ID NO: 45) and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 3. In certain embodiments, the core amino acid residues are fixed and any substitutions, conservative substitutions, deletions or additions occur at residues other than the core amino acid residues.

The $^{10}$Fn3 domain that binds to VEGFR2 may optionally be linked to an N-terminal extension (N1 or N2) of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 19), VSDVPRDL (SEQ ID NO: 20), and GVSDVPRDL (SEQ ID NO: 21), or N-terminal truncations of any one of SEQ ID NOs: 19, 20 or 21. Other suitable N-terminal extensions include, for example, $X_n$SDVPRDL (SEQ ID NO: 26), $X_n$DVPRDL (SEQ ID NO: 27), $X_n$VPRDL (SEQ ID NO: 28), $X_n$PRDL (SEQ ID NO: 29), $X_n$RDL (SEQ ID NO: 30), $X_n$DL (SEQ ID NO: 31), or $X_n$L, wherein n=0, 1 or 2 amino acids, wherein when n=1, X is Met or Gly, and when n=2, X is Met-Gly. In preferred embodiments, N1 comprises, consists essentially of, or consists of the amino acid sequence of SEQ ID NO: 19. In preferred embodiments, N2 comprises, consists essentially of, or consists of the amino acid sequence of SEQ ID NO: 20.

The $^{10}$Fn3 domain that binds to VEGFR2 may optionally comprise a C-terminal tail (C1 or C2). The C-terminal tails of the fibronectin based scaffold protein dimers of the claimed invention do not contain a DK sequence. Exemplary C-terminal tails include polypeptides that are from 1-20, 1-15, 1-10, 1-8, 1-5, 1-4, 1-3, 1-2, or 1 amino acids in length. Specific examples of C-terminal tails include EIEKPSQ (SEQ ID NO: 32), EIEKPCQ (SEQ ID NO: 6), and EIEK (SEQ ID NO: 4). In other embodiments, suitable C-terminal tails may be a C-terminally truncated fragment of SEQ ID NOs: 4, 6 or 32, including, for example, one of the following amino acid sequences (represented by the single letter amino acid code): EIE, EIEKP (SEQ ID NO: 33), EIEKPS (SEQ ID NO: 34), or EIEKPC (SEQ ID NO: 35). Other suitable C-terminal tails include, for example, ES, EC, EGS, EGC, EGSGS (SEQ ID NO: 36), or EGSGC (SEQ ID NO: 5). In certain embodiments, C1 comprises, consists essentially of, or consists of the amino acid sequence of SEQ ID NO: 4. In certain embodiments, C2 comprises, consists essentially of, or consists of the amino acid sequence of SEQ ID NO: 4, 5 or 6. In preferred embodiments, C1 comprises, consists essentially of, or consists of the amino acid sequence of SEQ ID NO: 4 and C2 comprises, consists essentially of, or consists of the amino acid sequence of SEQ ID NO: 6.

In certain embodiments, the $^{10}$Fn3 domain that binds to VEGFR2 comprises both an N-terminal extension and a C-terminal tail. In exemplary embodiments, N1 begins with Gly or Met-Gly, C1 does not contain a cysteine residue, N2 does not start with a Met, and C2 comprises a cysteine residue. Specific examples of $^{10}$Fn3 domains that bind to VEGFR2 are polypeptides comprising: (i) the amino acid sequence set forth in SEQ ID NO: 3, or (ii) an amino acid sequence having at least 85%, 90%, 95%, 97%, 98%, or 99% identity with the amino acid sequence set forth in SEQ ID NO: 3.

In certain embodiments, the D1 or D2 region is a $^{10}$Fn3 domain that binds to IGF-IR comprising a BC loop having the amino acid sequence of SEQ ID NO: 40, a DE loop having the amino acid sequence of SEQ ID NO: 41, and an FG loop having the amino acid sequence of SEQ ID NO: 42, wherein the $^{10}$Fn3 domain binds to IGF-IR with a $K_D$ of less than 100 nM.

In certain embodiments, the D1 or D2 region is an IGF-IR binder represented by the following amino acid sequence:

(SEQ ID NO: 2)
EVVAATPTSLIASWSARLKVARYYRITYGETGGNSPVQEFTVPKNVYTAT
ISGLKPGVDYTITVYAVTRFRDYQPISINYRT.

In SEQ ID NO: 2, the sequence of the BC, DE and FG loops have a fixed sequence as shown in bold (e.g., a BC loop having the amino acid sequence of SEQ ID NO: 40, a DE loop having the amino acid sequence of SEQ ID NO: 41, and an FG loop having the amino acid sequence of SEQ ID NO: 42) and the remaining sequence which is underlined (e.g., the sequence of the 7 beta strands and the AB, CD and EF loops) has anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the corresponding amino acids shown in SEQ ID NO: 2. In certain embodiments, the core amino acid residues are fixed and any substitutions, conservative substitutions, deletions or additions occur at residues other than the core amino acid residues.

The $^{10}$Fn3 domain that binds to IGF-IR may optionally be linked to an N-terminal extension (N1 or N2) of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 19), VSDVPRDL (SEQ ID NO: 20), and GVSDVPRDL (SEQ ID NO: 21), or N-terminal truncations of any one of SEQ ID NOs: 19, 20 or 21. Other suitable N-terminal extensions include, for example, $X_n$SDVPRDL (SEQ ID NO: 26), $X_n$DVPRDL (SEQ ID NO: 27), $X_n$VPRDL (SEQ ID NO: 28), $X_n$PRDL (SEQ ID NO: 29), $X_n$RDL (SEQ ID NO: 30), $X_n$DL (SEQ ID NO: 31), or $X_n$L, wherein n=0, 1 or 2 amino acids, wherein when n=1, X is Met or Gly, and when n=2, X is Met-Gly. In preferred embodiments, N1 comprises, consists essentially of, or consists of the amino acid sequence of SEQ ID NO: 19. In preferred embodiments, N2 comprises, consists essentially of, or consists of the amino acid sequence of SEQ ID NO: 20.

The $^{10}$Fn3 domain that binds to IGF-IR may optionally comprise a C-terminal tail (C1 or C2). The C-terminal tails of the fibronectin based scaffold protein dimers of the claimed invention do not contain a DK sequence. Exemplary C-terminal tails include polypeptides that are from 1-20, 1-15, 1-10, 1-8, 1-5, 1-4, 1-3, 1-2, or 1 amino acids in length. Specific examples of C-terminal tails include EIEKPSQ (SEQ ID NO: 32), EIEKPCQ (SEQ ID NO: 6), and EIEK (SEQ ID NO: 4). In other embodiments, suitable C-terminal tails may be a C-terminally truncated fragment of SEQ ID NOs: 4, 6 or 32, including, for example, one of the following amino acid sequences (represented by the single letter amino acid code): EIE, EIEKP (SEQ ID NO: 33), EIEKPS (SEQ ID NO: 34), or EIEKPC (SEQ ID NO: 35). Other suitable C-terminal tails include, for example, ES, EC, EGS, EGC, EGSGS (SEQ ID NO: 36), or EGSGC (SEQ ID NO: 5). In certain embodiments, C1 comprises, consists essentially of, or consists of the amino acid sequence of SEQ ID NO: 4. In certain embodiments, C2 comprises, consists essentially of, or consists of the amino acid sequence of SEQ ID NO: 4, 5 or 6. In preferred embodiments, C1 comprises, consists essentially of, or consists of the amino acid sequence of SEQ ID NO: 4 and C2 comprises, consists essentially of, or consists of the amino acid sequence of SEQ ID NO: 6.

In certain embodiments, the $^{10}$Fn3 domain that binds to IGF-IR comprises both an N-terminal extension and a C-terminal tail. In exemplary embodiments, N1 begins with Gly or Met-Gly, C1 does not contain a cysteine residue, N2 does not start with a Met, and C2 comprises a cysteine residue. Specific examples of $^{10}$Fn3 domains that bind to IGF-IR are polypeptides comprising: (i) the amino acid sequence set forth in SEQ ID NO: 2, or (ii) an amino acid sequence having at least 85%, 90%, 95%, 97%, 98%, or 99% identity with the amino acid sequence set forth in SEQ ID NO: 2.

The L region is a polypeptide linker. Exemplary polypeptide linkers include polypeptides having from 1-20, 1-15, 1-10, 1-8, 1-5, 1-4, 1-3, or 1-2 amino acids. Specific examples of suitable polypeptide linkers are described further herein. In certain embodiments, the linker may be a C-terminal tail polypeptide as described herein, an N-terminal extension polypeptide as described herein, or a combination thereof.

In certain embodiments, one or more of N1, N2, L, C1 or C2 may comprise an amino acid residue suitable for pegylation, such as a cysteine or lysine residue. In exemplary embodiments, C2 comprises at least one amino acid suitable for pegylation, such as a cysteine or lysine residue. Specific examples of suitable polypeptide linkers are described further below. Specific examples of fibronectin based scaffold protein dimers having the structure N1-D1-C1-L-N2-D2-C2 are polypeptides comprising: (i) the amino acid sequence set forth in any one of SEQ ID NOs: 48-55, or (ii) an amino acid sequence having at least 85%, 90%, 95%, 97%, 98%, or 99% identity with any one of SEQ ID NOs: 48-55.

In certain embodiments, fibronectin based scaffold protein dimers will have the structure N1-D1-L-N2-D2, wherein D1 and D2 each comprise an amino acid sequence having the following sequence:

(SEQ ID NO: 38)
EVVAATPTSLLISW(X)$_x$RYYRITYGETGGNSPVQEFTVP(X)$_y$TATISGL
KPGVDYTITVYAVT(X)$_z$PISINYRTEIEK

In SEQ ID NO: 38, the BC loop is represented by $X_x$, the DE loop is represented by $X_y$, and the FG loop is represented by $X_z$. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 38. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 38. In certain embodiments, the core amino acid residues are fixed and any substitutions, conservative substitutions, deletions or additions occur at residues other than the core amino acid residues. The EIEK tail (SEQ ID NO: 4) shown in bold is fixed. In certain embodiments, the amino acids immediately flanking the loop regions (e.g., the non-underlined residues) may each independently be substituted or deleted. When substituting the residues immediately flanking the loops, each residues may be substituted with a sequence having the same number of amino acids or with a larger amino acid sequence (e.g., insertions of 0-10, 0-8, 0-5, 0-3, or 0-2 amino acid residues). The non-underlined residues are part of the loop region and therefore are amenable to substitution without significantly affecting the structure of the $^{10}$Fn3 domain.

In certain embodiments, a fibronectin based scaffold protein dimer has the structure N1-D1-L-N2-D2, wherein D1 and D2 are selected from the group consisting of: (i) a $^{10}$Fn3 domain comprising SEQ ID NO: 38, wherein $X_x$ comprises, consists essentially of, or consists of the amino acid sequence of SEQ ID NO: 40, $X_y$ comprises, consists essentially of, or consists of the amino acid sequence of SEQ ID NO: 41, and $X_z$ comprises, consists essentially of, or consists of the amino acid sequence of SEQ ID NO: 42; and (ii) a $^{10}$Fn3 domain comprising SEQ ID NO: 38, wherein $X_x$ comprises, consists essentially of, or consists of the amino acid sequence of SEQ ID NO: 43, $X_y$ comprises, consists essentially of, or consists of the amino acid sequence of SEQ ID NO: 44, and $X_z$ comprises, consists essentially of, or consists of the amino acid sequence of SEQ ID NO: 45.

In an exemplary embodiment, a fibronectin based scaffold protein dimer has the structure N1-D1-L-N2-D2, wherein D1 comprises the amino acid sequence of SEQ ID NO: 38, wherein $X_x$ comprises, consists essentially of, or consists of the amino acid sequence of SEQ ID NO: 40, $X_y$ comprises, consists essentially of, or consists of the amino acid sequence of SEQ ID NO: 41, and $X_z$ comprises, consists essentially of, or consists of the amino acid sequence of SEQ ID NO: 42, and wherein D2 comprises the amino acid sequence of SEQ ID NO: 38, wherein $X_x$ comprises, consists essentially of, or consists of the amino acid sequence of SEQ ID NO: 43, $X_y$ comprises, consists essentially of, or consists of the amino acid sequence of SEQ ID NO: 44, and $X_z$ comprises, consists essentially of, or consists of the amino acid sequence of SEQ ID NO: 45.

In another exemplary embodiment, a fibronectin based scaffold protein dimer has the structure N1-D1-L-N2-D2, wherein D1 comprises the amino acid sequence of SEQ ID NO: 38, wherein $X_x$ comprises, consists essentially of, or consists of the amino acid sequence of SEQ ID NO: 43, $X_y$ comprises, consists essentially of, or consists of the amino acid sequence of SEQ ID NO: 44, and $X_z$ comprises, consists essentially of, or consists of the amino acid sequence of SEQ ID NO: 45; and wherein D2 comprises the amino acid sequence of SEQ ID NO: 38, wherein $X_x$ comprises, consists essentially of, or consists of the amino acid sequence of SEQ ID NO: 40, $X_y$ comprises, consists essentially of, or consists of the amino acid sequence of SEQ ID NO: 41, and $X_z$ comprises, consists essentially of, or consists of the amino acid sequence of SEQ ID NO: 42.

In certain embodiments, a fibronectin based scaffold protein dimer having the structure N1-D1-L-N2-D2 further comprises a C-terminal tail. In exemplary embodiments, the C-terminal tail comprises a residue suitable for addition of a PEG moiety, e.g., a lysine or cysteine residue. In a preferred embodiment, the C-terminal tail comprises the sequence PCQ.

In various embodiments, the L domain of a fibronectin based scaffold protein dimer having the structure N1-D1-L-N2-D2 is a polypeptide linker. Exemplary polypeptide linkers include polypeptides having from 1-20, 1-15, 1-10, 1-8, 1-5, 1-4, 1-3, or 1-2 amino acids. Specific examples of suitable polypeptide linkers are described further herein. In addition, N1 and N2 are N-terminal extensions as described herein above.

In preferred embodiments, the fibronectin based scaffold protein dimers described herein have increased stability either in vitro, in vivo or both. In certain embodiments, the fibronectin based scaffold protein dimers described herein have reduced fragmentation and/or decreased aggregation during storage in solution. In certain embodiments, the fibronectin based scaffold protein dimers described herein have increased serum half-life.

In exemplary embodiments, the fibronectin based scaffold protein dimers described herein have reduced fragmentation relative to a fibronectin based scaffold protein dimer comprising a DK sequence. In particular, the fibronectin based scaffold protein dimers described herein have increased stability relative to a fibronectin based scaffold protein dimer having one or more DK sequences in any one of: a C-terminal tail, an N-terminal extension or a linker between two $^{10}$Fn3 domains. For example, the fibronectin based scaffold protein dimers are generally more stable than fibronectin based scaffold protein dimers having a DK sequence in one or both C-terminal tail regions, e.g., comprising a tail having SEQ ID NO: 46 after the first and/or second $^{10}$Fn3 subunit. In exemplary embodiments, the fibronectin based scaffold protein dimers described herein have reduced fragmentation relative to a fibronectin based scaffold protein dimer having the formula N1-D1-C1-L-N2-D2-C2, wherein C1 and/or C2 comprise SEQ ID NO: 46. Fragmentation may be assessed, for example, using RP-HPLC analysis, as described in Example 3.

In exemplary embodiments, the fibronectin based scaffold protein dimers described herein exhibit less than 7%, 6%, 5%, 4%, 3.5%, 3%, 2% or less fragmentation upon storage in solution for four weeks at pH 4.0. In certain embodiments, the fibronectin based scaffold protein dimers described herein exhibit a level of fragmentation that is reduced by at least 25%, 30%, 40%, 50%, 60%, 70%, 75%, 80% or more relative to an equivalent version of the fibronectin based scaffold protein dimer that contains one or more DK sequences.

In exemplary embodiments, the fibronectin based scaffold protein dimers described herein exhibit a serum half-life that is increased by at least 10%, 20%, 25%, 30%, 40%, 50%, 60%, 70%, 80% or more relative to the serum half-life of a an equivalent version of the fibronectin based scaffold protein dimer that contains one or more DK sequences. In other embodiments, the fibronectin based scaffold protein dimers described herein exhibit a serum half-life that is increased by at least 2-fold, 3-fold, 5-fold, 10-fold, or more relative to the serum half-life of a an equivalent version of the fibronectin based scaffold protein dimer that contains one or more DK sequences.

In certain embodiments, the application provides an E/I fibronectin based scaffold protein dimer, comprising one $^{10}$Fn3 domain that binds to EGFR and one $^{10}$Fn3 domain that binds to IGF-IR. In certain embodiments, an E/I fibronectin based scaffold protein dimer comprises the amino acid sequence of any one of SEQ ID NOs: 22-25. In other embodiments, an E/I fibronectin based scaffold protein dimer comprises the amino acid sequence of SEQ ID NO: 25. In some embodiments, an E/I fibronectin based scaffold protein dimer comprises an amino acid sequence having at least 70, 75, 80, 85, 90, 95, 97, 98, 99 or 100% identity with the amino acid sequence of any one of SEQ ID NOs: 22-25.

Polypeptide Linkers

The application provides multivalent fibronectin based scaffold proteins comprising at least two $^{10}$Fn3 domains linked via a polypeptide linker. In one embodiment, the application provides fibronectin based scaffold dimers comprising two $^{10}$Fn3 domains linked via a polypeptide linker (L). The polypeptides comprise an N-terminal domain comprising a first $^{10}$Fn3 domain and a C-terminal domain comprising a second $^{10}$Fn3 domain. The first and second <sup>10</sup>Fn3 domains may be directly or indirectly linked via a polypeptide linker (I.). Additional linkers or spacers, e.g., SEQ ID NOS: 4, 6 or 32, may be introduced at the C-terminus of the first <sup>10</sup>Fn3 domain between the <sup>10</sup>Fn3 domain and the polypeptide linker. Additional linkers or spacers may be introduced at the N-terminus of the second <sup>10</sup>Fn3 domain between the <sup>10</sup>Fn3 domain and the polypeptide linker.

Suitable linkers for joining the <sup>10</sup>Fn3 domains are those which allow the separate domains to fold independently of each other forming a three dimensional structure that permits high affinity binding to a target molecule. The application provides that suitable linkers that meet these requirements comprise glycine-serine based linkers, glycine-proline based linkers, proline-alanine based linkers as well as the linker SEQ ID NO: 7. The Examples described in WO 2009/142773 demonstrate that Fn3 domains joined via these linkers retain their target binding function. In some embodiments, the linker is a glycine-serine based linker. These linkers comprise glycine and serine residues and may be between 8 and 50, 10 and 30, and 10 and 20 amino acids in length. Examples of such linkers include SEQ ID NOs: 8-12. In some embodiments the polypeptide linker is selected from SEQ ID NOs: 8 and 9. In some embodiments, the linker is a glycine-proline based linker. These linkers comprise glycine and proline residues and may be between 3 and 30, 10 and 30, and 3 and 20 amino acids in length. Examples of such linkers include SEQ ID NOs: 13, 14 and 15. In some embodiments, the linker is a proline-alanine based linker. These linkers comprise proline and alanine residues and may be between 3 and 30, 10 and 30, 3 and 20 and 6 and 18 amino acids in length. Examples of such linkers include SEQ ID NOs: 16, 17 and 18. It is contemplated, that the optimal linker length and amino acid composition may be determined by routine experimentation by methods well known in the art. In some embodiments, the polypeptide linker is SEQ ID NO: 7. In exemplary embodiments, the linker does not contain any DK sequences.

Pharmacokinetic Moieties

In one aspect, the application provides for fibronectin based scaffold proteins further comprising a pharmacokinetic (PK) moiety. Pharmokinetics encompasses properties of a compound including, by way of example, absorption, distribution, metabolism, and elimination by a subject. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The fibronectin based scaffold proteins may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety. A PK moiety refers to any protein, peptide, or moiety that affects the pharmacokinetic properties of a biologically active molecule when fused to the biologically active molecule.

PK moieties that tend to slow clearance of a protein from the blood include polyoxyalkylene moieties, e.g., polyethylene glycol, sugars (e.g., sialic acid), and well-tolerated protein moieties (e.g., Fc, Fc fragments, transferrin, or serum albumin). The fibronectin based scaffold proteins may be fused to albumin or a fragment (portion) or variant of albumin as described in U.S. Publication No. 20070048282. In some embodiments, the PK moiety is a serum albumin binding protein such as those described in U.S. Publication Nos. 2007/0178082 and 2007/0269422. In some embodiments, the PK moiety is a serum immunoglobulin binding protein such as those described in U.S. Publication No. 2007/0178082.

In some embodiments, the fibronectin based scaffold proteins may be attached to a PK moiety comprising a nonproteinaceous polymer. In some embodiments, the polymer is polyethylene glycol ("PEG"), polypropylene glycol, or polyoxyalkylenes, as described in U.S. Pat. No. 4,640, 835; 4,496,689; 4,301,144; 4,670,417; 4,791,192 or 4,179, 337. In exemplary embodiments, the polymer is a PEG moiety.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, J. Biol. Chem., 252, 3571 (1977) and J. Biol. Chem., 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a fibronectin based scaffold protein containing a PEG molecule is also known as a conjugated protein, whereas the protein lacking an attached PEG molecule can be referred to as unconjugated.

The size of PEG utilized will depend on several factors including the intended use of the fibronectin based scaffold protein. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging applications, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to fibronectin based scaffold proteins. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to the fibronectin based scaffold protein. In some embodiments, the PEG moiety is about 20, 30, 40, 50, 60, 70, 80, or 90 KDa. In some embodiments, the PEG moiety is about 40 KDa.

In some embodiments, PEGylated fibronectin based scaffold proteins contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in a pegylated fibronectin based scaffold protein is from about 3,000 Da to 60,000 Da, or from about 10,000 Da to 36,000 Da. In a one embodiment, the PEG in a pegylated fibronectin based scaffold protein is a substantially linear, straight-chain PEG.

One skilled in the art can select a suitable molecular mass for PEG, e.g., based on how the pegylated fibronectin based scaffold protein will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In some embodiments, a fibronectin based scaffold protein is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a fibronectin based scaffold protein's c-amino group of a lysine is the available (free) amino group.

In one specific embodiment, carbonate esters of PEG are used to form the PEG-fibronectin based scaffold protein conjugates. N,N'-disuccinimidylcarbonate (DSC) may be used in the reaction with PEG to form active mixed PEG-succinimidyl carbonate that may be subsequently reacted with a nucleophilic group of a linker or an amino group of a fibronectin based scaffold protein (see U.S. Pat. No. 5,281,698 and U.S. Pat. No. 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of a fibronectin based scaffold protein can be performed according to the methods of the state of the art, for example by reaction of the fibronectin based scaffold protein with electrophilically active PEGs (supplier: Shearwater Corp., USA, world wide web at shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylate at an ε-amino group of a lysine of a fibronectin based scaffold protein or at the N-terminal amino group of the fibronectin based scaffold protein.

In another embodiment, PEG molecules may be coupled to sulfhydryl groups on a fibronectin based scaffold protein (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments, the pegylated fibronectin based scaffold protein is produced by site-directed pegylation, particularly by conjugation of PEG to a cysteine moiety. In certain embodiments, the Cys residue may be positioned at the N-terminus, between the N-terminus and the most N-terminal beta or beta-like strand, at the C-terminus, or between the C-terminus and the most C-terminal beta or beta-like strand of the fibronectin based scaffold protein. In certain embodiments, the fibronectin based scaffold protein is a dimer and the Cys residue may be positioned at the N-terminus, between the N-terminus and the most N-terminal beta or beta-like strand, at the C-terminus, or between the C-terminus and the most C-terminal beta or beta-like strand of either binding domain of the fibronectin based scaffold protein dimer. In certain embodiments, the Cys residue may be positioned at the N-terminus of the fibronectin based scaffold protein dimer, between the N-terminus and the most N-terminal beta or beta-like strand of the fibronectin based scaffold protein dimer (i.e., of the N-terminal binding domain of the fibronectin based scaffold protein dimer), or at the C-terminus of the fibronectin based scaffold protein dimer, or between the C-terminus and the most C-terminal beta or beta-like strand of the fibronectin based scaffold protein dimer (i.e., of the C-terminal binding domain of the fibronectin based scaffold protein dimer). A Cys residue may be situated at other positions as well, particularly any of the loops that do not participate in target binding or between two binding domains of a multivalent fibronectin based scaffold protein. A PEG moiety may also be attached by other chemistry, including by conjugation to amines.

In some embodiments where PEG molecules are conjugated to cysteine residues on a fibronectin based scaffold protein, the cysteine residues are native to the fibronectin based scaffold protein, whereas in other embodiments, one or more cysteine residues are engineered into the fibronectin based scaffold protein. Mutations may be introduced into a fibronectin based scaffold protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of fibronectin based scaffold proteins, given that the crystal structure of the tenth fn3 domain framework based on which fibronectin based scaffold proteins are designed has been solved (see Dickinson, et al., J. Mol. Biol. 236(4): 1079-92 (1994)) and thus the surface-exposed residues identified. In one embodiment, cysteine residues are introduced into fibronectin based scaffold protein at or near the N- and/or C-terminus, or within loop regions. Pegylation of cysteine residues may be carried out using, for example, PEG-maleimide, PEG-vinylsulfone, PEG-iodoacetamide, or PEG-orthopyridyl disulfide.

In some embodiments, the pegylated fibronectin based scaffold protein comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated fibronectin based scaffold proteins comprise one or more PEG molecules covalently attached to a linker, which in turn is attached to the alpha amino group of the amino acid residue at the N-terminus of the fibronectin based scaffold protein. Such an approach is disclosed in U.S. Publication No. 2002/0044921 and PCT Publication No. WO94/01451.

In one embodiment, a fibronectin based scaffold protein is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

In exemplary embodiments, a fibronectin based scaffold protein is pegylated in a C-terminal tail region as described further herein. Exemplary C-terminal tails include, for example, a polypeptide having any one of SEQ ID NOs: 5, 6 or 35.

Conventional separation and purification techniques known in the art can be used to purify PEGylated fibronectin based scaffold proteins, such as size exclusion (e.g., gel filtration) and ion exchange chromatography. Products may also be separated using SDS-PAGE. Products that may be separated include mono-, di-, tri-poly- and un-pegylated fibronectin based scaffold proteins, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment of the invention, the PEG in a pegylated fibronectin based scaffold protein is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-fibronectin based scaffold protein, more preferably at least 90%, and most preferably at least 95%.

In another embodiment, the pegylated fibronectin based scaffold proteins will preferably retain at least about 25%, 50%, 60%, 70%, 80%, 85%, 90%, 95% or 100% of the biological activity associated with the unmodified protein. In one embodiment, biological activity refers to its ability to bind to one or more target molecules, as assessed by $K_D$, $k_{on}$ or $k_{off}$. In one specific embodiment, the pegylated fibronectin based scaffold protein shows an increase in binding to one or more target molecules relative to unpegylated fibronectin based scaffold protein.

The serum clearance rate of PEG-modified fibronectin based scaffold proteins may be decreased by about 10%, 20%, 30%, 40%, 50%, 60%, 70%, 80%, or even 90%, relative to the clearance rate of the unmodified fibronectin based scaffold protein. The PEG-modified fibronectin based scaffold protein may have a half-life ($t_{1/2}$) which is enhanced relative to the half-life of the unmodified fibronectin based scaffold protein. The half-life of PEG-modified fibronectin based scaffold protein may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified fibronectin based scaffold protein. In some embodiments, the protein half-life is determined in vitro, such as in a buffered saline solution or in serum. In other embodiments, the protein half-life is an in vivo half life, such as the half-life of the fibronectin based scaffold protein in the serum or other bodily fluid of an animal.

Nucleic Acid-Protein Fusion Technology

In one aspect, the application provides fibronectin based scaffold proteins comprising a fibronectin type III domain that bind a human target, such as, for example, TNF-alpha, EGFR, VEGFR2, IGF-IR, or other proteins. One way to rapidly make and test Fn3 domains with specific binding properties is the nucleic acid-protein fusion technology of Adnexus, a Bristol-Myers Squibb Company. Such in vitro expression and tagging technology, termed PROfusion™, that exploits nucleic acid-protein fusions (RNA- and DNA-protein fusions) may be used to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO00/34784; WO01/64942; WO02/032925; and Roberts and Szostak, Proc Natl. Acad. Sci. 94:12297-12302, 1997, herein incorporated by reference.

Vectors & Polynucleotides

Nucleic acids encoding any of the various fibronectin based scaffold proteins disclosed herein may be synthesized chemically, enzymatically or recombinantly. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The fibronectin based scaffold proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces alpha-factor leaders), or acid phosphatase leader, the C. albicans glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the nucleic acid encoding the fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the fibronectin based scaffold protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

Transcription of a DNA encoding fibronectin based scaffold proteins by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. One useful transcription termination component is the bovine growth hormone polyadenylation region. See WO94/11026 and the expression vector disclosed therein.

The recombinant DNA can also include any type of protein tag sequence that may be useful for purifying the fibronectin based scaffold protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified fibronectin based scaffold proteins are prepared by culturing suitable host/vector systems to express the recombinant proteins. For many applications, the small size of the fibronectin based scaffold proteins would make expression in *E. coli* the preferred method for expression. The fibronectin based scaffold protein is then purified from culture media or cell extracts.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the fibronectin based scaffold proteins may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Fibronectin based scaffold proteins disclosed herein can also be produced using cell-free translation systems. For such purposes the nucleic acids encoding the fibronectin based scaffold protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Fibronectin based scaffold proteins can also be produced by chemical synthesis (e.g., by the methods described in Solid Phase Peptide Synthesis, 2nd ed., 1984, The Pierce Chemical Co., Rockford, Ill.). Modifications to the fibronectin based scaffold protein can also be produced by chemical synthesis.

The fibronectin based scaffold proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, fibronectin based scaffold proteins may be exchanged into different buffers and/or concentrated by any of a variety of methods known to the art, including, but not limited to, filtration and dialysis.

The purified fibronectin based scaffold protein is preferably at least 85% pure, more preferably at least 95% pure, and most preferably at least 98% pure. Regardless of the exact numerical value of the purity, the fibronectin based scaffold protein is sufficiently pure for use as a pharmaceutical product.

Exemplary Uses

In one aspect, the application provides fibronectin based scaffold proteins labeled with a detectable moiety. The fibronectin based scaffold proteins may be used for a variety of diagnostic applications. The detectable moiety can be any one which is capable of producing, either directly or indirectly, a detectable signal. For example, the detectable moiety may be a radioisotope, such as H3, C14, C13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a detectable moiety to a fibronectin based scaffold protein, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

Fibronectin based scaffold proteins linked with a detectable moiety also are useful for in vivo imaging. The polypeptide may be linked to a radio-opaque agent or radioisotope, administered to a subject, preferably into the bloodstream, and the presence and location of the labeled protein in the subject is assayed. This imaging technique is useful, for example, in the staging and treatment of malignancies when the fibronectin based scaffold protein binds to a target associated with cancer. The fibronectin based scaffold protein may be labeled with any moiety that is detectable in a subject, whether by nuclear magnetic resonance, radiology, or other detection means known in the art.

Fibronectin based scaffold proteins also are useful as affinity purification agents. In this process, the fibronectin based scaffold proteins are immobilized on a suitable support, such a Sephadex resin or filter paper, using methods well known in the art.

Fibronectin based scaffold proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting a target molecule in a sample, such as VEGFR2, IGF-IR or EGFR. A method may comprise contacting the sample with a fibronectin based scaffold protein described herein, wherein said contacting is carried out under conditions that allow fibronectin based scaffold protein-target complex formation; and detecting said complex, thereby detecting said target in said sample. Detection may be carried out using any technique known in the art, such as, for example, radiography, immunological assay, fluorescence detection, mass spectroscopy, or surface plasmon resonance. The sample will often be a biological sample, such as a biopsy, and particularly a biopsy of a tumor, a suspected tumor. The sample may be from a human or other mammal. The fibronectin based scaffold protein may be labeled with a labeling moiety, such as a radioactive moiety, a fluorescent moiety, a chromogenic moiety, a chemiluminescent moiety, or a hapten moiety. The fibronectin based scaffold protein may be immobilized on a solid support.

In one aspect, the application provides fibronectin based scaffold proteins useful in the treatment of disorders. The diseases or disorders that may be treated will be dictated by the binding specificity of the fibronectin based scaffold protein. The application also provides methods for administering fibronectin based scaffold proteins to a subject. In some embodiments, the subject is a human. In some embodiments, the fibronectin based scaffold proteins are pharmaceutically acceptable to a mammal, in particular a human. A "pharmaceutically acceptable" polypeptide refers to a polypeptide that is administered to an animal without significant adverse medical consequences. Examples of pharmaceutically acceptable fibronectin based scaffold proteins include $^{10}$Fn3 domains that lack the integrin-binding domain (RGD) and $^{10}$Fn3 domains that are essentially endotoxin or pyrogen free or have very low endotoxin or pyrogen levels.

In certain embodiments, fibronectin based scaffold proteins, in particular fibronectin based scaffold proteins that bind to IGF-IR, VEGFR2 and/or EGFR, are useful in treating disorders such as cancer. In certain embodiments, the fibronectin based scaffold proteins are useful in treating cancers associated with IGF-IR, VEGFR2 and/or EGFR mutations or expression levels. In some embodiments, administration of a fibronectin based scaffold protein treats an antiproliferative disorder in a subject. In some embodiments, administration of a fibronectin based scaffold protein inhibits tumor cell growth in vivo. The tumor cell may be derived from any cell type including, without limitation, epidermal, epithelial, endothelial, leukemia, sarcoma, multiple myeloma, or mesodermal cells. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/IGF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SY5Y cells, Sk-Mel-2 cells, NCI-H929, RPM 18226, and A431 cells. In some embodiments, the fibronectin based scaffold protein inhibits tumor cell growth relative to the growth of the tumor in an untreated animal. In some embodiments, the fibronectin based scaffold protein inhibits tumor cell growth by 50, 60, 70, 80% or more relative to the growth of the tumor in an untreated animal. In some embodiments, the inhibition of tumor cell growth is measured at least 7 days or at least 14 days after the animals have started treatment with the fibronectin based scaffold protein. In some embodiments, another antineoplastic agent is administered to the animal with the fibronectin based scaffold protein.

In certain aspects, the disclosure provides methods for administering fibronectin based scaffold protein for the treatment and/or prophylaxis of tumors and/or tumor metastases, where the tumor is selected from the group consisting of brain tumor, tumor of the urogenital tract, tumor of the lymphatic system, stomach tumor, laryngeal tumor, monocytic leukemia, lung adenocarcinoma, small-cell lung carcinoma, pancreatic cancer, glioblastoma and breast carcinoma, without being restricted thereto.

In certain aspects, the disclosure provides methods for administering fibronectin based scaffold proteins for the treatment of cancerous diseases selected from the group consisting of squamous cell carcinoma, bladder cancer, stomach cancer, liver cancer, kidney cancer, colorectal cancer, breast cancer, head cancer, neck cancer, oesophageal cancer, gynecological cancer, thyroid cancer, lymphoma, chronic leukemia and acute leukemia.

In other embodiments, a fibronectin based scaffold protein binds to a target involved in inflammatory response and/or autoimmune disorders, such as, for example, tumor necrosis factor (TNF) alpha. Such fibronectin based scaffold proteins may be useful for treating autoimmune disorders such as rheumatoid arthritis, ankylosing spondylitis, Crohn's disease, psoriasis and refractory asthma.

Formulation and Administration

The application further provides pharmaceutically acceptable compositions comprising the fibronectin based scaffold proteins described herein, wherein the composition is essentially endotoxin or pyrogen free.

Therapeutic formulations comprising fibronectin based scaffold proteins are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The fibronectin based scaffold proteins may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In certain embodiments, the application provides stable compositions of fibronectin based scaffold proteins having a pH of 4.0-6.5. In other embodiments, the application provides stable compositions of fibronectin based scaffold proteins having a pH of 4.0-5.5. In other embodiments, the application provides stable compositions of fibronectin based scaffold proteins having a pH of 5.5. In other embodiments, the application provides stable compositions of fibronectin based scaffold proteins having a pH of 4.0. In particular, the application provides stable compositions of fibronectin based scaffold proteins that have reduced fragmentation and/or low levels of aggregation during storage in solution. As demonstrated in the exemplification section, the fibronectin based scaffold proteins described herein having increased stability at pH 4.0 while at the same time exhibition decreased levels of aggregation at pH 4.0 as compared to a pH of 5.5. Such stable, soluble formulations having a pH of 4.0 are particularly suitable for intravenous administration. In some embodiments, the protein concentration in such stable formulations is at least 3 mg/mL. In exemplary embodiments, the protein concentration in such stable formulations is at least 5 mg/mL. In certain embodiments, the protein concentration in such stable formulations ranges from 3-10 mg/mL, 3-8 mg/mL, 3-6 mg/mL, 3-5 mg/mL, 4-10 mg/mL, 4-8 mg/mL, 4-6 mg/mL, 5-10 mg/mL, 5-8 mg/mL, or 5-6 mg/mL. In exemplary embodiments, the stable formulations of fibronectin based scaffold proteins have reduced aggregation relative to an equivalent formulation of a fibronectin based scaffold protein at a higher pH. For example, the stable formulations may exhibit at least 10%, 20%, 30%, 40%, 50%, 60%, 70%, 75%, 80%, or less aggregation during storage in solution for 4 weeks at pH 4.0 relative to the level of aggregation seen during storage of the fibronectin based scaffold protein during storage for 4 weeks at pH 5.5 or higher. In certain embodiments, the stable formulations of fibronectin based scaffold proteins have less than 10%, 8%, 7%, 6%, 5%, 4%, 3%, 2%, 1%, or less aggregates after storage at 25° C. for at least 4 weeks. In certain embodiments, the stable formulations of fibronectin based scaffold proteins have less than 7%, 6%, 5%, 4%, 3.5%, 3%, 2% or less fragmentation upon storage in solution for four weeks at pH 4.0 and 25° C. In certain embodiments, the stable formulations of fibronectin based scaffold proteins have less than 5% fragmentation and less than 5% aggregation during storage in solution at 25° C. for at least 4 weeks. In exemplary embodiments, the stable formulations of fibronectin based scaffold proteins have less than 4% fragmentation and less than 4% aggregation during storage in solution at 25° C. for at least 4 weeks.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the fibronectin based scaffold proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each fibronectin based scaffold protein will be dependent on the identity of the protein, the preferred dosages can range from about 10 mg/square meter to about 2000 mg/square meter, more preferably from about 50 mg/square meter to about 1000 mg/square meter.

For therapeutic applications, the fibronectin based scaffold proteins are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of fibronectin based scaffold proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the fibronectin based scaffold protein typically will be formulated at a concentration of about 0.1 mg/ml to 100 mg/ml, although wide variation outside of these ranges is permitted. For the treatment of disease, the appropriate dosage of fibronectin based scaffold proteins will depend on the type of disease to be treated, as defined above, the severity and course of the disease, whether the fibronectin based scaffold proteins are administered for preventive or therapeutic purposes, the course of previous therapy, the patient's clinical history and response to the fibronectin based scaffold protein, and the discretion of the attending physician. The fibronectin based scaffold protein is suitably administered to the patient at one time or over a series of treatments.

```
SEQUENCE LISTING

WT Core Sequence
EVVAATPTSLLISWDAPAVTVRYYRITYGETGGNSPVQEFTVPGSKSTAT
ISGLKPGVDYTITVYAVTGRGDSPASSKPISINYRT
(SEQ ID NO: 1)

I core (SEQ ID NO: 2)
EVVAATPTSLLISWSARLKVARYYRITYGETGGNSPVQEFTVPKNVYTAT
ISGLKPGVDYTITVYAVTRFRDYQPISINYRT V core (SEQ ID NO: 3)
EVVAATPTSILLISWRHPHFPTRYYRITYGETGGNSPVQEFTVPLQPPTA
TISGLKPGVDYTITVYAVTDGRNGRLLSIPISINYRT Short Tail (SEQ ID NO: 1)
EIEK Modified Cys Tail (SEQ ID NO: 51)
EGSGC Cys Tail (SEQ ID NO: 6)
EIEKPCQ Fn based linker (SEQ ID NO: 7)
PSTSTST GS5 linker (SEQ ID NO: 8)
GSGSGSGSGS GS10 linker (SEQ ID NO: 9)
GSGSGSGSGSGSGSGSGSGS (GGGGS)3 (SEQ ID NO: 10)
GGGGS GGGGS GGGGS (GGGGS)5 (SEQ ID NO: 11)
GGGGS GGGGS GGGGS GGGGS GGGGS

G4SG4SG3SG (SEQ ID NO: 12)
GGGGSGGGGSGGGSG

GPG (SEQ ID NO: 13)

GPGPGPG (SEQ ID NO: 14)

GPGPGPGPGPG (SEQ ID NO: 15)

PA3 linker (SEQ ID NO: 16)
PAPAPA

PA6 linker (SEQ ID NO: 17)
PAPAPAPAPAPA

PA9 linker (SEQ ID NO: 18)
PAPAPAPAPAPAPAPAPA

MGVSDVPRDL (SEQ ID NO: 19)

VSDVPRDL (SEQ ID NO: 20)

GVSDVPRDL (SEQ ID NO: 21)

DK+ VEGER2/IGE-IR Binder (SEQ ID NO: 22)
MGVSDVPRDLEVVAATPTSLLISWSARLKVARYYRITYGETGGNSPVQEF
TVPKNVYTATISGLKPGVDYTITVYAVTRFRDYQPISINYRTEIDKPSTS
TSTVSDVPRDLEVVAATPT SLLISWRHPHFPTRYYRITYGETGGNSPVQ
EFTVPLQPPTATISGLKPGVDYTITVYAVTDGRNGRLLSIPISINYRT
EIDKPCQ DK+ EGFR/IGF-4R Binder (SEQ ID NO: 23)
MGVSDVPRDLEVVAATPTSLLISWSARLKVARYYRITYGETGGNSPVQEF
TVPKNVYTATISGLKPGVDYYTITVYAVTRFRDYQPISINYRTEIDKGSG
SGSGSGSGSGSGSGSGSVSDVPRDLEVVAATPTSLLISWWAPVDRYQYYR
ITYGETGGNSPVQEFTVPRDVYTATISGLKPGVDYTITVYAVTDYKPHAD
GPHTYHESPISINVRTEIDKPCQ DK- EGFR/IGF-IR Binder with GSgC Tail
(SEQ ID NO: 24)
MGVSDVPRDLEVVAATPTSLLISWSARLKVARYYRITYGETGGNSPVQEF
TVPKNVYTATISGLKPGVDYTITVYAVTRFRDYQPISINYRTEIEKGSGS
```

SEQUENCE LISTING

```
GSGSGSGSGSGSGSGSVS DVPRDLEVVAATPTSLLISWWAPVDRYQYYR
ITYGETGGNSPVQEFTVPRDVYTATISG LKPGVDYTITVYAVTDYKPHA
DGPHTYHESPISINYRTEGSGC

DK- EGFR/IGF-IR Binder with EIEKPCQ Tail
(SEQ ID NO: 25)
MGVSDVPRDLEVVAATPTSLLISWSARLKVARYYFITYGETGGNSPVQEF
TVPKNVYTATISGKKPGVDYTITVYAVTRFRDYQPISINYRTEIEKGSGS
GSGSGSGSGSCSGSGSVSDVPRDLEVVAATPTSLLISWWAPVDRYQYYRI
TYGETGGNSPVQEFTVPRDVYTATISG LKPGVDYTITVYAVTDYKPHAD
GPHTYHESPISINYRTEIEKPCQ X_nSDVPRDL, wherein n = 0, 1 or 2 amino acids,
wherein when n = 1, X is Met or Gly, and when
n = 2, X is Met-Gly (SEQ ID NO: 26)

X_nDVPRDL wherein n = 0, 1 or 2 amino acids,
wherein when n = 1, X is Met or Gly, and when
n = 2, X is Met-Gly (SEQ ID NO: 27)

X_nVPRDL, wherein n = 0, 1 or 2 amino acids,
wherein when n = 1, X is Met or Gly, and when
n = 2, X is Met-Gly (SEQ ID NO: 28)

X_nPRDL, wherein n = 0, 1 or 2 amino acids,
wherein when n = 1, X is Met or Gly, and when
n = 2, X is Met-Gly (SEQ ID NO: 29)

X_nRDL, wherein n = 0, 1 or 2 amino acids, wherein
when n = 1, X is Met or Gly, and when n = 2,
X is Met-Gly (SEQ ID NO: 30)

X_nDL, wherein n = 0, 1 or 2 amino acids, wherein
when n = 1, X is Met or Gly, and when n = 2,
X is Met-Gly (SEQ ID NO: 31)

EIEKPSQ (SEQ ID NO: 32)

EIEKP (SEQ ID NO: 33)

EIEKPS (SEQ ID NO: 34)

EEEEEEEE (SEQ ID NO: 35)

EGSGS (SEQ ID NO: 36)

WT Fibronectin Sequence
VSDVPRDLEVVAATPTSLLISWDAPAVTVRYYRITYGETGGNSPVQEFTV
PGSKSTATISGLKPGVDYTTIVYAVTGRGDSPASSKPISINYRT
(SEQ ID NO: 37)

10Fn Core with EIEK Tail
EVVAATPTSLLISAW(X)_xRYYRITYGETGGNSPVQEFTVP(X)_yTATISG
LKPGVDYTITVYAVT(X)_zPISINYRTEIEK (SEQ ID NO: 38)

E Core (SEQ ID NO: 39)
EVVAATPTSLLISWWAPVDRYQYYRITYGETGGNSPVQEFTVPRDVYTAT
ISGLKPGVDYTITVYAVTDYKPHADGPHTYHESPISINYRT IGF-IR BC Loop (SEQ ID NO: 40)
SARLKVA IGF-IR DE Loop (SEQ ID NO: 41)
KNVY IGF-IR FG Loop (SEQ ID NO: 42)
RFRDYQ VEGFR2 BC Loop (SEQ ID NO: 43)
RHPHFPT VEGFR2 DE Loop (SEQ ID NO: 44)
LQPP VEGFR2 FG Loop (SEQ ID NO: 45)
DGRNGRLLSI
```

```
EIDK (SEQ ID NO: 46)

EIDKPCQ (SEQ ID NO: 47)

I-Fn-V(2DK-) with Cys tail (SEQ ID NO: 48)
MGVSDVPRDLEVVAATPTSLLISWSARLKVARYYRITYGETGGNSPVQEF
TVPKNVYTATISGLKPGVDYTITVYAVTRFRDYQPISINYRTEIEKPSTS
TSTVSDVPRDLEVVAATPTSLLISWRHPHFPTRYYRITYGETGGNSPVQE
FTVPLQPPTATISGLKPGVDYTITVYAVTDGRNGRLLSIPISINYRT
EIEKPCQ I-Fn-V(2DK-) with ser tail (SEQ ID NO: 49)
MGVSDVPRDLEVVAATPTSLLISWSARLKVARYYRITYGETGGNSPVQEF
TVPKNVYTATISGLKPGVDYTITVYAVTRFRDYQPISINYRTEIEKPSTS
TSTVSDVPRDLEVVAATPT SLLISWRHPHFPTRYYRITYGETGGNSPV
QEFTVPLQPPTATISGLKPGVDYTITVYAVTDGRNGRLLSIPISINYRT
EIEKPCQ I-GS5-V(2DK-) with ser or cys tail (SEQ ID NO: 50)
MGVSDVPRDLEVVAATPTSLLISWSARLKVARYYRITYGETGGNSPVQEF
TVPKNVYTATISGLKPGVDYTITVYAVTRFRDYQPISINYRTEIEKGSGS
GSGSGSVSDVPRDLEVVAATPTSLLISWRHPHFPTRYYRITYGETGGNSP
VQEFTVPLQPPTATISGLKPGVDYTITVYAVTDGRNGRLLSIPISINYRT
EIEKPXQ, wherein X = serine or cysteine I-GS10-V(2DK-) with ser or cys tail
(SEQ ID NO: 51)
MGVSDVPRDLEVVAATPTSLLISWSARLKVARYYRITYGETGGNSPVQEF
TVPKNVYTATISGLKPGVDYTITVYAVTRFRDYQPISINYRTEIEKGSGS
GSGSGSGSGSGSGSCSVSDVPRDLEVVAATPTSLLISWRHPHFPTRYYRI
TYGETGGNSPVQEFTVPLQPPTATISGLKPGVDYTITVYAVTDGRNGRLL
SIPISINYRTEIEKPXQ, wherein X = serine or cysteine V-Fn-I(2DK-) with ser tail (SEQ ID NO: 52)
MGVSDVPRDLEVVAATPTSLLISWRHPHFPTRYYRITYGETGGNSPVQEF
TVPLQPPTATISGLKPGVDYTITVYAVTDGRNGRLLSIPISINYRTEIEK
PSTSTSTVSDVPRDLEVVAATP TSLLISWSARLKVARYYRITYGETGGN
SPVQEFTVPKNVYTATISGLKPGVDYTITVYAVTRFRDYQPISINYRT
EIEKPSQ V-Fn-1(2DK-) with cys tail (SEQ ID NO: 53)
MGVSDVPRDLEVVAATPTSLLISWRHPHFPTRYYRITYGETGGNSPVQEF
TVPLQPPTATISGLKPGVDYTITVYAVTDGRNGRLLSIPISINYRTEIEK
PSTSTSTVSDVPRDLEVVAATPTSLLISWSARLKVARYYRITYGETGGNS
PVQEFTVPKNVYTATISGLKPGVDYTITVYAV TRFRDYQPISINYRT
EIEKPCQ V-GS5-I(2DK-) with ser or cys tail (SEQ ID NO: 54)
MGVSDVPRDLEVVAATPTSLLISWRHPHFPTRYYRITYGETGGNSPVQEF
TVPLQPPTATISGLKPGVDYTITVYAVTDGRNGRLLSIPISINYRTEIEK
GSGSGSGSGSVSDVPRDLEVV AATPTSLLISWSARLKVARYYRITYGET
GGNSPVQEFTVPKNVYTATISGLKPGVDYTIT VYAVTRFRDYQPISINY
RTEIEKPXQ, wherein X = serine or cysteine V-GS10-I(2DK-) with ser or cys tail
(SEQ ID NO: 55)
MGVSDVPRDLEVVAATPTSLLISWRHPHFPTRYYRITYGETGGNSPVQE
FTVPLQPPTATISGLKPGVDYTITVYAVTDGRNGRLLISIPISINYRT
EIEKGSGSGSGSGSGSGSGSGSGSVSDVPRDLEVVAATPTSLLISWSAR
LKVARYYRITYGETGGNSPVQEFTVPKNVYTATISGLKPGVDYTITVYA
VTRFRDYQPISINYRTEIEKPXQ, wherein X = serine or
cysteine VI(DK+) (SEQ ID NO: 56)
GVSDVPRDLEVVAATPTSLLISWSARLKVARYYRITYGETGGNSPVQEFT
VPKNVYTAT ISGLKPGVDYTITVYAVTRFRDYQPISINYRTEIDKPSTS
TSTVSDVPRDLEVVAATPTSLLISWRHPHFPTRYYRITYGETGGNSPVQE
FTVPLQPPTATISGLKPGVDYTITVYAVTDG RNGRLLSIPISINYRT
EIDKPCQ VI(DK) (SEQ ID NO: 57)
GVSDVPRDLEVVAATPTSLLISWSARLKVARYYRITYGETGGNSPVQEFT
VPKNVYTATISGLKPGVDYTITVYAVTRFRDYQPISINYRTEIEKPSTST
STVSLDVPRDLEVVAATPTSL LISWRHPHFPTRYYRITYGETGGNSPVQ
```

-continued

SEQUENCE LISTING

EFTVPLQPPTATISGLKPGVDYTITVYAVTDGRNGRLLSIPISINYR
<u>TEIEKPCQ</u>

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1. Fibronectin Based Scaffold Proteins

Various fibronectin based scaffold proteins were generated, including VEGFR2/IGF-IR binders ("V/I binders") and EGFR/IGF-IR binders ("E/I binders"). The following table depicts constructs described herein and their corresponding SEQ ID NOs

TABLE 1

Overview of various V/I and E/I binders.

| Construct | Description | SEQ ID NO: | Abbreviation |
|---|---|---|---|
| DK+ IGF-IR/ VEGFR2 Binder with EIDKPCQ Tail | A bivalent V/I construct with a C1 tail consisting of SEQ ID NO: 46 and a C2 tail consisting of SEQ ID NO: 47 | 22 | V/I(DK+) |
| DK+ EGFR/ IGF-IR Binder with EIDKPCQ Tail | A bivalent E/I construct with a C1 tail consisting of SEQ ID NO: 46 and a C2 tail consisting of SEQ ID NO: 47 | 23 | E/I(DK+) |
| DK− EGFR/ IGF-IR Binder with EGSGC Tail | A bivalent E/I construct with a C1 tail consisting of SEQ ID NO: 4 and a C2 tail consisting of SEQ ID NO: 5 | 24 | E/I(DK−, no C-term) |
| DK− EGFR/ IGF-IR Binder with EIEKPCQ Tail | A bivalent E/I construct with a C1 tail consisting of SEQ ID NO: 4 and a C2 tail consisting of SEQ ID NO: 6 | 25 | E/I(2DK−) |

SEQ ID NO: 22 is the amino acid sequence of the V/I(DK+) bivalent construct that was first described in WO 2009/142773. V/I(DK+) comprises fibronectin domains that bind to IGF-IR and VEGFR2. The IGF-IR binding fibronectin core has the sequence set forth in SEQ ID NO: 2 and the VEGFR2 binding fibronectin core has the sequence set forth in SEQ ID NO: 3. The two domains are connected by a polypeptide linker derived from the amino acid sequence that connects the first and second Fn3 domains in human fibronectin (SEQ ID NO: 7). The I binding subunit of V/I(DK+) contains a C-terminal extension (C1) having the amino acid sequence SEQ ID NO: 46, i.e., containing a DK site. The V binding subunit of V/I(DK+) contains a C-terminal extension (C2) having the amino acid sequence of SEQ ID NO: 47, i.e., containing a DK site.

SEQ ID NO: 23 is the amino acid sequence of the E/I(DK+) bivalent construct. E/I(DK+) comprises fibronectin domains that bind to IGF-IR and EGFR. The IGF-IR binding fibronectin core has the sequence set forth in SEQ ID NO: 2 and the EGFR2 binding fibronectin core has the sequence set forth in SEQ ID NO: 39. The two domains are linked by a glycine-serine polypeptide linker having SEQ ID NO: 9. The I binding subunit of E/I(DK+) contains a C-terminal extension (C1) having the amino acid sequence SEQ ID NO: 46, i.e., containing a DK site. The E binding subunit of E/I(DK+) contains a C-terminal extension (C2) having the amino acid sequence of SEQ ID NO: 47, i.e., containing a DK site.

SEQ ID NO: 24 is the amino acid sequence of the E/I(DK−, no C-term) bivalent construct. The E/I(DK−, no C-term) comprises the IGF-IR core (SEQ ID NO: 2) and EGFR core (SEQ ID NO: 39) linked by a glycine-serine linker (SEQ ID NO: 9). The IGF-IR binding subunit contains a C-terminal extension (C1) having the amino acid sequence SEQ ID NO: 4, i.e., containing an EK site rather than a DK site. The EGFR binding subunit contains a C-terminal extension (C2) having the amino acid sequence of SEQ ID NO: 5, i.e., lacking a DK site.

SEQ ID NO: 25 is the amino acid sequence of the E/I(2DK−) bivalent construct. The E/I(2DK−) comprises the IGF-IR core (SEQ ID NO: 2) and EGFR core (SEQ ID NO: 39) linked by a glycine-serine linker (SEQ ID NO: 9). The IGF-IR binding subunit contains a C-terminal extension (C1) having the amino acid sequence SEQ ID NO: 4, i.e., containing an EK site rather than a DK site. The EGFR binding subunit contains a C-terminal extension (C2) having the amino acid sequence of SEQ ID NO: 6, i.e., containing an EK site rather than a DK site.

Example 2: Expression and Purification of Fibronectin Based Scaffold Proteins

Expression of E/I Molecules

E/I bivalent constructs are expressed in *E. coli* cells in soluble form. The inclusion bodies are recovered by cell disruption and centrifugation. The E/I proteins are filtered and captured using column chromatography. The purified protein is then covalently linked to a PEG via maleimide chemistry at a single cysteine residue. The PEGylated product is then polished using column chromatography and formulated using tangential flow filtration.

Expression of V/I Molecules

For expression of V/I bivalent constructs, a nucleotide sequence encoding the construct is cloned into an inducible expression vector and is expressed into intracellular inclusion bodies in *E. coli* cells. Cell bank vials generated from a culture of a single plated colony are used to inoculate a shake flask culture as an inoculum for a large-scale fermentor. Alternatively, a seed fermentor is used for an inoculum culture, depending on the final fermentation volume. The large-scale fermentation contains a growth phase to accumulate biomass and a production phase to generate the fibronectin based scaffold proteins. For primary recovery, intracellular inclusion bodies are released from harvested cells using a microfluidizer and recovered by centrifugation, followed by washes with buffer and water.

The purification process for the bivalent constructs uses a Guanidine-HCl based resolubolization of inclusion bodies, followed by refolding the protein. The refolded protein is filtered and loaded onto a cation exchange chromatography column. The product is then purified using a hydrophobic interaction column and the resulting elution pool is PEGylated by the addition of the PEG reagent to produce PEGylated protein.

The PEGylated protein is then purified over a second cation exchange chromatography column. The elution is concentrated to a target protein concentration and then exchanged into the formulation buffer using ultrafiltration/diafiltration (UF/DF). The UF/DF product is filtered using a final 0.22 μm filter. The filtered product is then filled into vials to produce the final drug product.

Example 3: Effects of Protein Concentration on V/I Protein Stability

The effects of protein concentration on physical (aggregation) and chemical (fragmentation) stability of purified V/I(DK+) (SEQ ID NO: 22) were examined. V/I(DK+) protein was formulated in 10 mM succinic acid, 5% sorbitol at pH 5.5. V/I protein concentration was either at 3 mg/mL or at 5 mg/ml. Samples were stored at 4° C. for a period of 12 months, with samples being collected and analyzed at 1 month, 6 weeks, 2 months, 3 months, 6 months, 9 months and 12 months.

The amount of aggregation is measured by assessing the percentage of total protein that has formed aggregates (measured as High Molecular Weight ("HMW") species) over time. Aggregation was determined using Size Exclusion-High Performance Liquid Chromatography (SE-HPLC) analysis to assess the levels of HMW over time. SE-HPLC analysis was conducted using a Superdex 200 10/300 GL column, with a mobile phase of 0.2M potassium phosphate, 0.15 M sodium chloride, 0.02% sodium azide, pH 6.8. Flow rate was 0.5 mL/min with detection at 280 nm. The effects of protein concentration on aggregation of V/I protein over time (0-12 months) is depicted in FIG. 1. V/I(DK+) aggregates at a rate of 0.3%/month at a concentration of 3 mg/mL. Higher protein concentration (5 mg/ml) leads to a faster aggregation rate.

Fragmentation is measured by assessing percentage of total protein that has been fragmented, or "clipped", over time. Levels of clipped protein were determined by utilizing Reversed Phase-High Performance Liquid Chromatography (RP-HPLC). RP-HPLC was performed using a Varian PLRP-S column (4.6*250 mm, 300 Å pore size, 5 μm particle size). Separation of the various species is achieved via a gradient comprised of water/acetonitrile/trifluoroacetic acid. Flow rate was 1.0 mL/min. Dual detection was conducted at 280 nm (for protein-related species) and with evaporative light scattering (ELS, for PEG-related species). FIG. 2 demonstrates that fragmentation of V/I(DK+) was found to be less dependent on protein concentration than was aggregation. The fragmentation rate for V/I(DK+) was ~0.1%/month at 4° C.

Based on these aggregation and fragmentation data, a formulation of V/I(DK+) having a protein concentration of 3 mg/mL would be preferred over a concentration of 5 mg/mL in order to minimize aggregation and to ensure sufficient stability for one year.

Example 4: Effects of pH on V/I Protein Stability

The effects of pH on physical and chemical stability of purified V/I(DK+) (SEQ ID NO: 22) were examined. V/I (DK+) protein was formulated in 50 mM sodium chloride, with the buffer component being 20 mM sodium acetate (for pH 4 and 5) or 20 mM sodium phosphate (for pH 6 and 7), and was stored at 25° C.

Samples were collected once per week for a period of four weeks and evaluation of aggregation was carried out using SE-HPLC analysis as described in Example 3. The effects of pH on aggregation of V/I(DK+) protein over time (0-4 wks) are depicted in FIG. 3. The lowest aggregation rate was observed in the samples having the lowest pH tested (pH 4.0). The highest aggregation rate was observed in the samples having the highest pH tested (pH 7.0).

Samples were collected once per week for a period of four weeks and evaluation of fragmentation was carried out using SE-HPLC analysis as described in Example 3. The effects of pH on fragmentation of V/I(DK+) protein is depicted in FIG. 4. While a low pH (pH 4.0) was found to prevent aggregation over time of the V/I(DK+) protein (FIG. 3), low pH was found to lead to an increase in protein fragmentation of the V/I(DK+) protein (FIG. 4).

To identify clip sites in the fragmented V/I(DK+) protein, liquid chromatography-Mass Spectrometry (LC-MS) was performed. V/I(DK+) protein was formulated in 10 mM sodium acetate, 150 mM sodium chloride, pH 5.5, at 5 mg/mL protein concentration. LC-MS was performed according to the RP-HPLC method described in Example 3 followed by coupling to a Thermo LTQ ion trap mass spectrometer (MS). The HPLC eluent was split 1:5 with 0.2 mL/min flow diverted into the MS. On-line detection at 280 nm was maintained. FIG. 5 depicts the LC-MS data from this experiment and demonstrates that several aspartate (D) residues are involved in fragmentation, with D95 and D200 being the predominant sites at which fragmentation occurs. It should be noted that while there are several D residues throughout the V/I(DK+) protein (e.g. D5, D9, D110), only the D95 and D200 residues are immediately followed by a lysine residue. "VI des Met" indicates a cleavage event occurring at the maleimide bond of the PEG conjugation as a result of heat stress.

Based on these experiments, aggregation and fragmentation are best balanced by fixing the formulation pH at 5.5, however, neither degradation pathway (aggregation and fragmentation) could be eliminated by relying on this pH level alone.

Example 5: Evaluation of Aggregation and Fragmentation on E/I Proteins

To confirm that the aggregation and fragmentation instability issues observed in V/I(DK+) (SEQ ID NO: 22) were issues common to other structurally related bivalent constructs, the aggregation and fragmentation properties of E/I(DK+) (SEQ ID NO: 23) were also assessed at several pH levels.

E/I(DK+) was formulated in 10 mM succinic acid, 5% sorbitol and at pH 4.0, 4.5 or 5.5. E/I(DK+) was formulated into the desired formulation via tangential flow filtration (TFF) using a 30 kD MWCO membrane. At least six dia-volumes of buffer were exchanged to achieve the final formulation. Concentration of the resulting protein was verified by A280 and adjusted to 5 mg/mL with additional formulation buffer. Formulated E/I(DK+) was sterile filtered in a laminar flow hood, and filled into sterilized glass vials for stability monitoring. The vials were capped and crimped, followed by placement into temperature-controlled incubators at 4, 25 and 37° C.

Aggregation rate of E/I(DK+) was assessed by performing SE-HPLC analysis. SE-HPLC was performed using a Shodex KW404-4F HPLC column (4.6*250 mm, 300 Å pore size, 5 μm particle size) and a mobile phase comprised of 10 mM succinic acid/3% sorbitol/0.4M arginine at pH 5.5. Flow rate was 0.35 mL/min and detection was conducted at 280 nm. FIG. 6 shows that, similar to V/I(DK+), the aggregation rate of E/I(DK+) was higher for samples stored at higher pH levels at 25° C. than for samples stored at lower pH levels at 25° C. The same data trends were also observed for samples stressed at 37° C.

The effect of protein concentration on aggregation rate of E/I(DK+) was also assessed. Similar to V/I(DK+), Table 2 illustrates that higher concentrations (7 mg/ml) of E/I(DK+) were associated with a higher percentage of aggregate formation (lower percentage of monomers) after 4 weeks. Table 2 also demonstrates that by reducing pH along with protein concentration, the percent of aggregation can be further decreased.

TABLE 2

| Protein Conc. | Formulation pH | % Monomer |
|---|---|---|
| 7.5 mg/mL | 5.5 | 94.30% |
| 5.0 mg/mL | 5.5 | 97.70% |
| 5.0 mg/mL | 4.0 | 99.20% |

Figure 7:
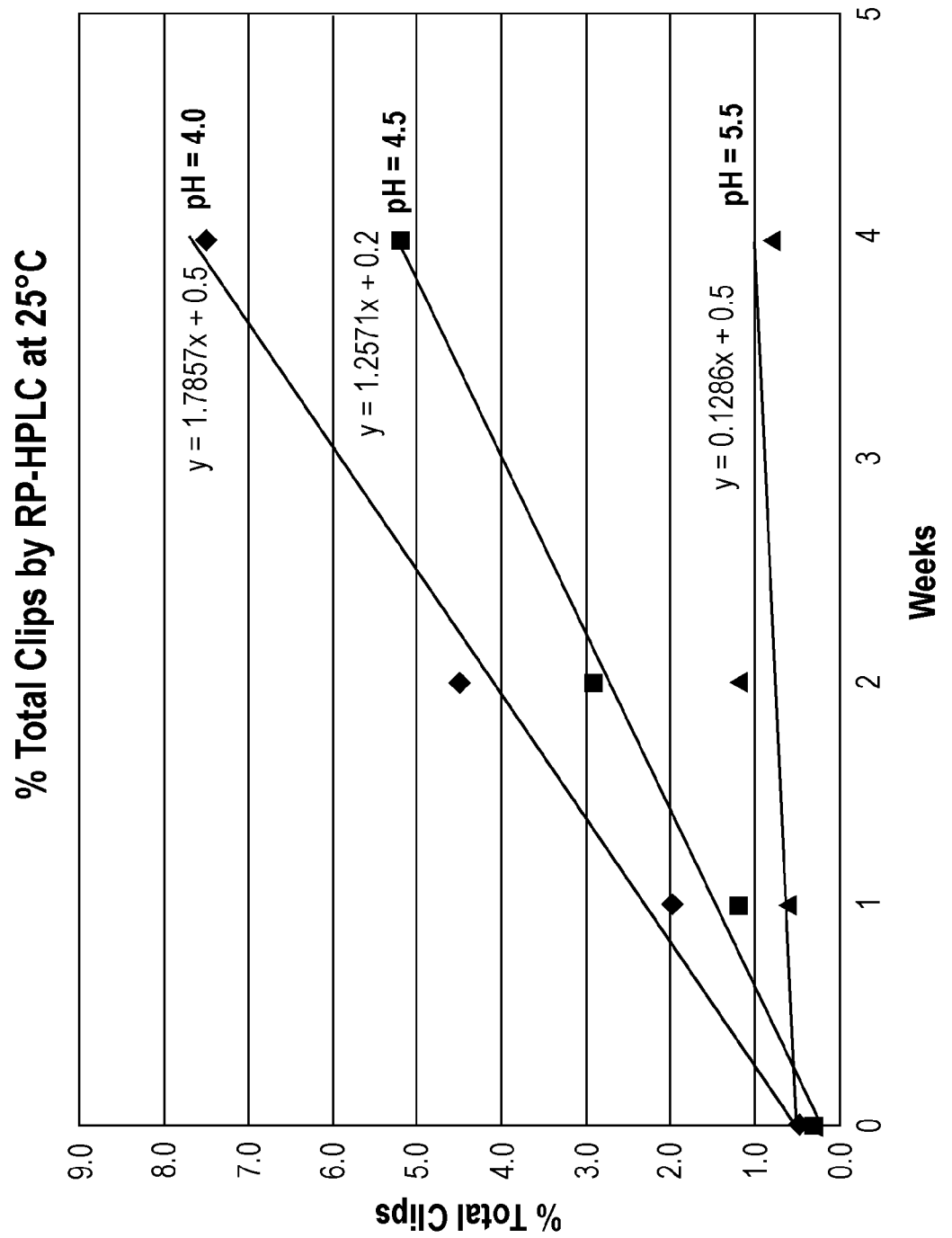
FIG. 7. SE-HPLC data showing the effect of pH on the amount of protein fragmentation over time for the pegylated E/I(DK+) (SEQ ID NO: 23). The pegylated protein was stored for 4 week at 25° C. in 10 mM succinic acid, 5% sorbitol, pH 4.0, 4.5 and 5.5.

Fragmentation of the E/I(DK+) was assessed by performing RP-HPLC analysis as described in Example 3. FIG. 7 shows that, similar to V/I(DK+), the fragmentation rate of E/I(DK+) was highest for samples stored at lower pH levels at 25° C. then for samples stored at higher pH levels at 25° C. The same data trends were also observed for samples stressed at 37° C.

Figure 8:
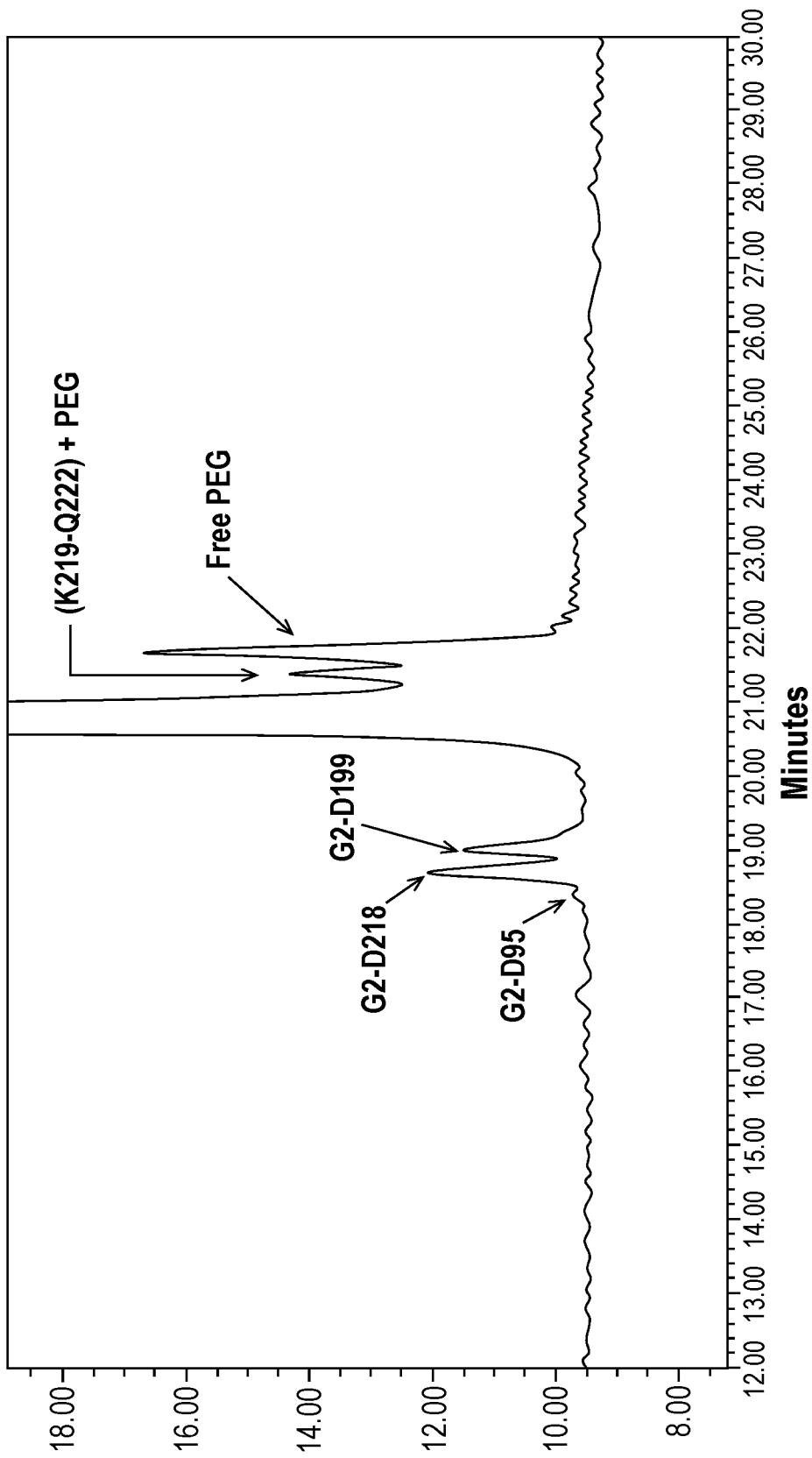
FIG. 8. RP-HPLC profile showing the sites of cleavage of the pegylated E/I(DK+) (SEQ ID NO: 23) after storage at 25° C. for 4 weeks in 10 mM succinic acid, 5% sorbitol, pH 4.0, 5 mg/mL protein concentration. As indicated in the figure, protein cleavage occurs directly following positions D95, D199 and D218.

To identify clip sites in the fragmented E/I(DK+) protein, LC-MS was performed as described in Example 4. E/I(DK+) was formulated in 10 mM succinic acid, 5% sorbitol, pH 4.0, at 5 mg/mL protein concentration and was maintained at 25° C. to induce protein stress. FIG. 8 depicts the LC-MS data from this experiment and demonstrates that several aspartate (D) residues are involved in fragmentation, including D95 and D218 (the homologous position to D200 in V/I(DK+)). Fragmentation was also observed at D199. The D199 site is specific to these E/I molecules and is not found in V/I molecules, as it is located within the FG binding loop of the EGFR-binding region.

Example 6: Evaluation of Aggregation and Fragmentation in DK Minus E/1 Variants

Various E/I binders (SEQ ID NOs: 23-25) were formulated and their physical (aggregation) and chemical (fragmentation) stability was compared to each other under identical conditions (see Table 1). Based upon the characterization of the D95 and D218 clipped sites observed in E/I(DK+) (Example 5), and based on the fact that these DK clip sites are located in the structurally nonessential C-terminal tails, two different E/I constructs were generated in which the C-terminal tail DK sites were removed or substituted.

The E/I(DK+) molecule (SEQ ID NO: 23) is the control E/I binder that contains a C-terminal tail comprising DK sites (D95 and D218) after each of the two binding domains. The physical and chemical stability of this molecule was characterized in Example 5. The E/I(DK−, no C-term) molecule (SEQ ID NO: 24) does not contain any DK sites. In this molecule, the aspartate at position 95 was mutated to a glutamic acid, and the EIDKPCQ tail (SEQ ID NO: 47) was replaced with an EGSGC tail (SEQ ID NO: 5). The E/I(2DK−) molecule (SEQ ID NO: 25) also does not contain any DK sites. In this molecule the aspartates at positions 95 and 218 have been replaced with glutamic acids. V/I(DK+) was included in this study as a control.

The E/I proteins (SEQ ID NOs: 23-25) were formulated in 10 mM succinic acid, 5% sorbitol at pH 4.0. In addition, E/I(DK+) (SEQ ID NO: 23) and V/I(DK+) (SEQ ID NO: 22) were formulated in 10 mM succinic acid, 5% sorbitol at pH 5.5. Surfactant was not found to be necessary based on a preliminary surfactant screen. E/I(DK+) was formulated into the desired formulation via tangential flow filtration (TFF) using a 30 kD MWCO membrane. At least six dia-volumes of buffer were exchanged to achieve the final formulation. Concentration of the resulting protein was verified by A280 and adjusted to 5 mg/mL with additional formulation buffer. Each formulated bivalent construct was sterile filtered in a laminar flow hood, and filled into sterilized glass vials for stability monitoring. The vials were capped and crimped, followed by placement into temperature-controlled incubators at 4, 25 and 37° C.

Figure 9:
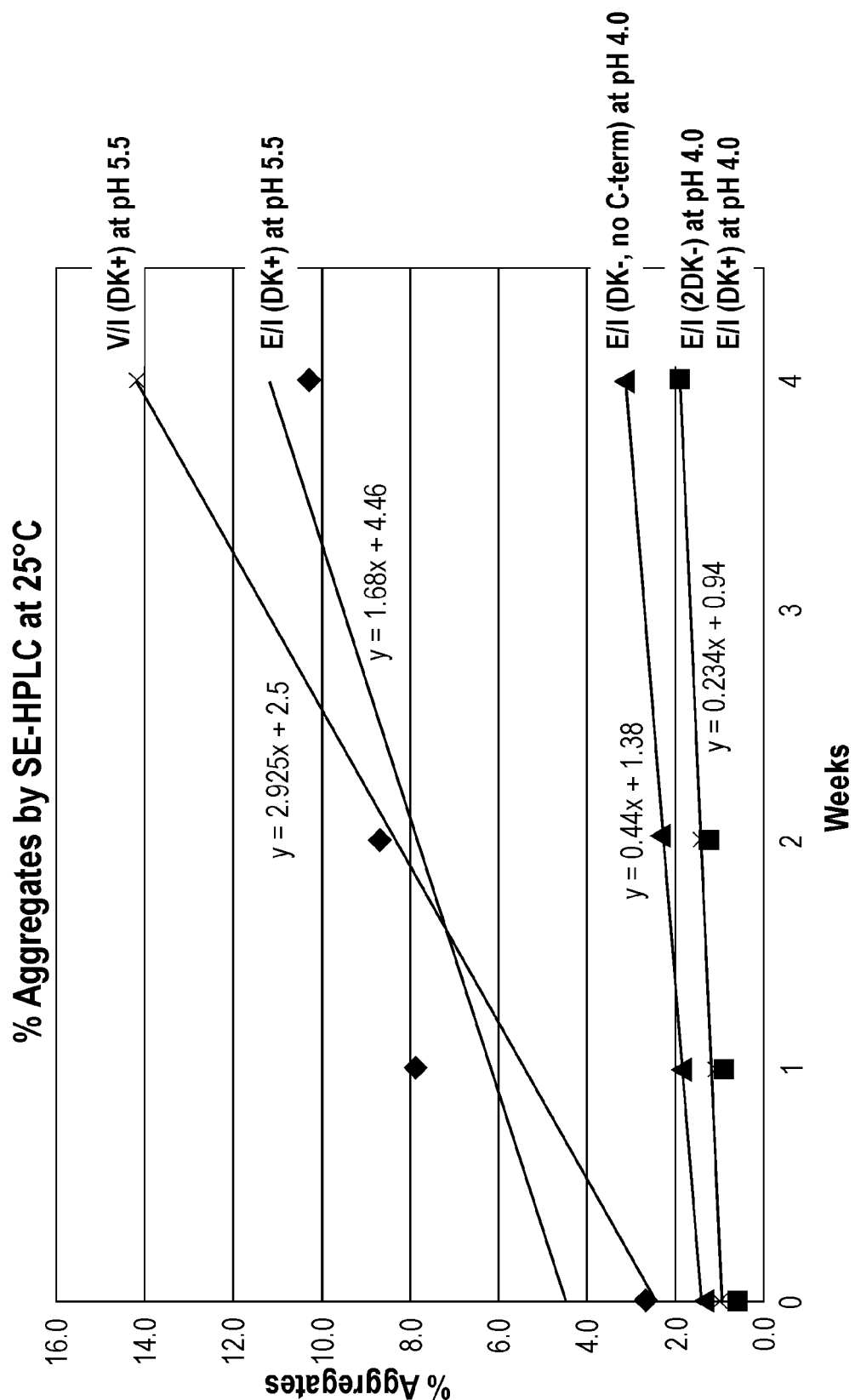
FIG. 9. SE-HPLC data demonstrating showing the effect of pH on protein aggregation over time for various fibronectin based scaffold protein constructs. The level of aggregation for various fibronectin based scaffold proteins was tested at either pH 5.5 or pH 4.0 during storage for 4 weeks at 25° C. E/I(DK+) is SEQ ID NO: 23; E/I(DK−, no C-term) is SEQ ID NO: 24; E/I(2DK−) is SEQ ID NO: 25; and V/I(DK+) is SEQ ID NO: 22.

Aggregation rate for the different E/I molecules was determined by performing SE-HPLC as described according to Example 5 and the results from this experiment are illustrated in FIG. 9. As expected, the rate of aggregation is significantly higher at pH 5.5 than at pH 4.0 for E/I(DK+) at 25° C. Based on the slopes seen in FIG. 9, the rate of aggregation for E/I(DK+) is approximately 7-fold higher at pH 5.5 than at pH 4.0 at 25° C. For the two E/I molecules lacking DK sites, the aggregation rate was unaffected at pH 4.0. E/I(DK+) and V/I(DK+) displayed similar aggregation rates at pH 5.5.

Figure 10:
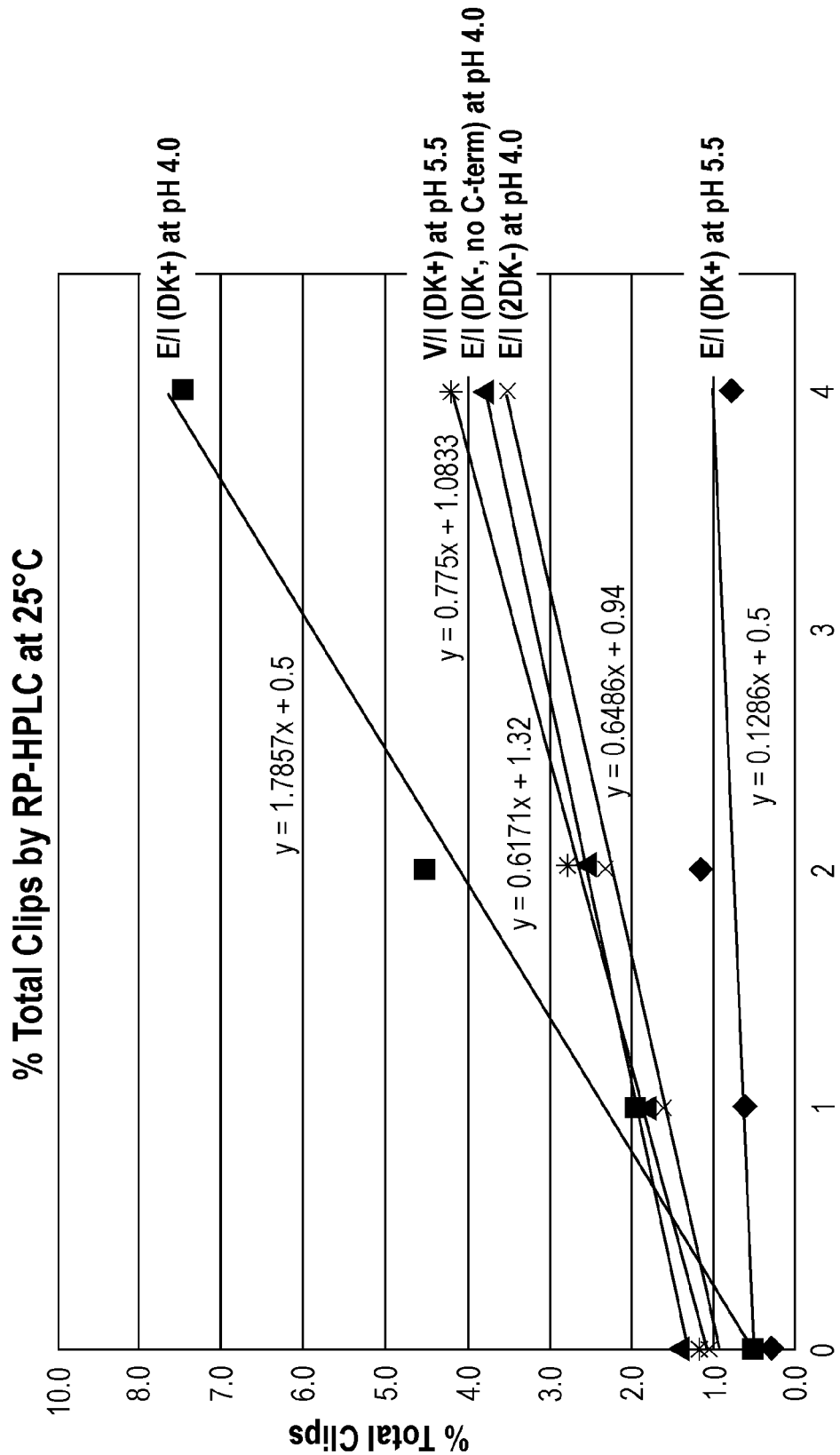
FIG. 10. RP-HPLC data showing the amount of fragmentation of various fibronectin based scaffold proteins at different pHs during storage for 4 weeks at 25° C. Fibronectin based scaffold proteins that contain DK sequences are more susceptible to fragmentation at pH 4.0 as compared to pH 5.5. Fibronectin based scaffold proteins that do not contain DK sequences are more resistant to fragmentation at pH 4.0 as compared to fibronectin based scaffold proteins that contain DK sequences, E/I(DK+) is SEQ ID NO: 23; E/I (DK−, no C-term) is SEQ ID NO: 24; E/I(2DK−) is SEQ ID NO: 25; and V/I(DK+) is SEQ ID NO: 22.

Fragmentation rate for the different E/I molecules was determined by performing RP-HPLC according to Example 3 and the results from this experiment are illustrated in FIG. 10. In terms of clipping, FIG. 10 shows lower clip rates at pH 5.5 than at pH 4.0 for E/I(DK+) at 25° C. Among the molecules represented in FIG. 10, the highest clip rate was seen in E/I(DK+) at pH 4.0, which was significantly minimized when the formulation pH was increased to pH 5.5. However, as described above, aggregation rate was highest at pH 5.5 for this molecule. For the other two E/I molecules lacking DK sites, the clip rates at pH 4.0 decreased by approximately 3-fold as compared to E/I(DK+) at the same pH1. V/I(DK+) displayed a higher degree of fragmentation as compared to E/I(DK+) at the same pH (pH 5.5) indicating that although the V/I(DK+) and E/I(DK+) molecules are similar, the V/I(DK+) molecule is more susceptible to fragmentation.

Figure 11:
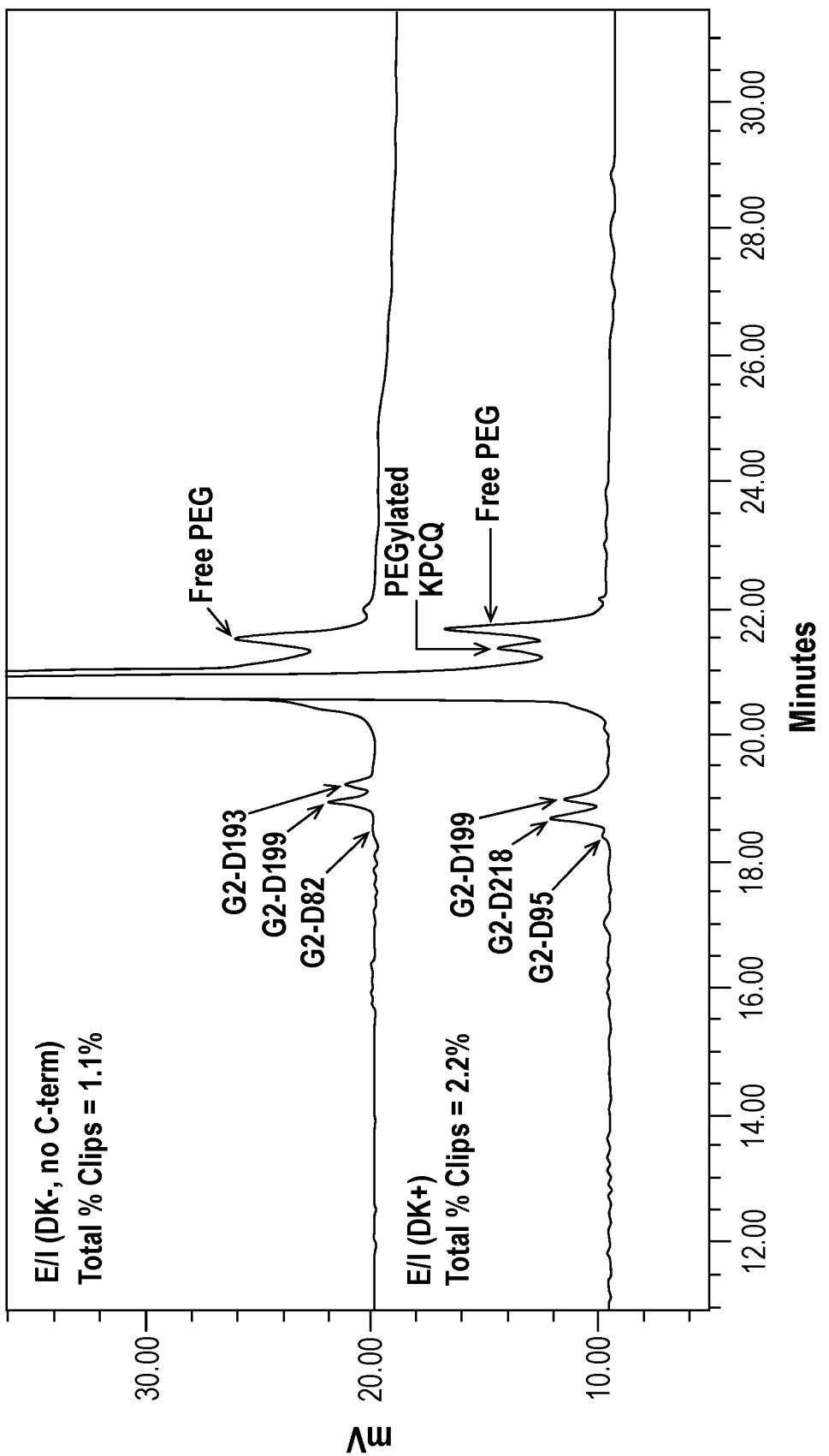
FIG. 11. LC-MS data demonstrating that the major cleavage site in the E/I(DK−, no C-term) molecule (SEQ ID NO: 24) is D199, while the major cleavage site in the E/I(DK+) molecule (SEQ ID NO: 23) is D218.

Characterization of clipped sites for E/I(DK−, no C-term), as compared to the clipped sites for E/I(DK+), was performed using LC-MS as described in Example 4. The two different E/I Binders were each formulated in 10 mM succinic acid, 5% sorbitol, pH 4.0, at 5 mg/mL protein concentration and were maintained at 25° C. to induce protein stress. FIG. 11 depicts the LC-MS data from this experiment and demonstrates that the fragmentation profiles differ between the two different E/I binders. The predominant aspartate (D) residues involved in fragmentation in E/I(DK+) were D95, D218 and D199. By contrast, the predominant aspartate residues involved in fragmentation in E/I(DK−, no C-term) were D199, D82 and D193. However, as illustrated in Table 3 below, the percentage of total clips was nearly halved in E/I(DK−, no C-term) after 4 weeks as compared to E/I(DK+) after this same period (3.8% compared to 7.5%). These results indicate that E/I(DK−, no C-term) is associated with reduced fragmentation as compared to E/I(DK+).

Figure 12:
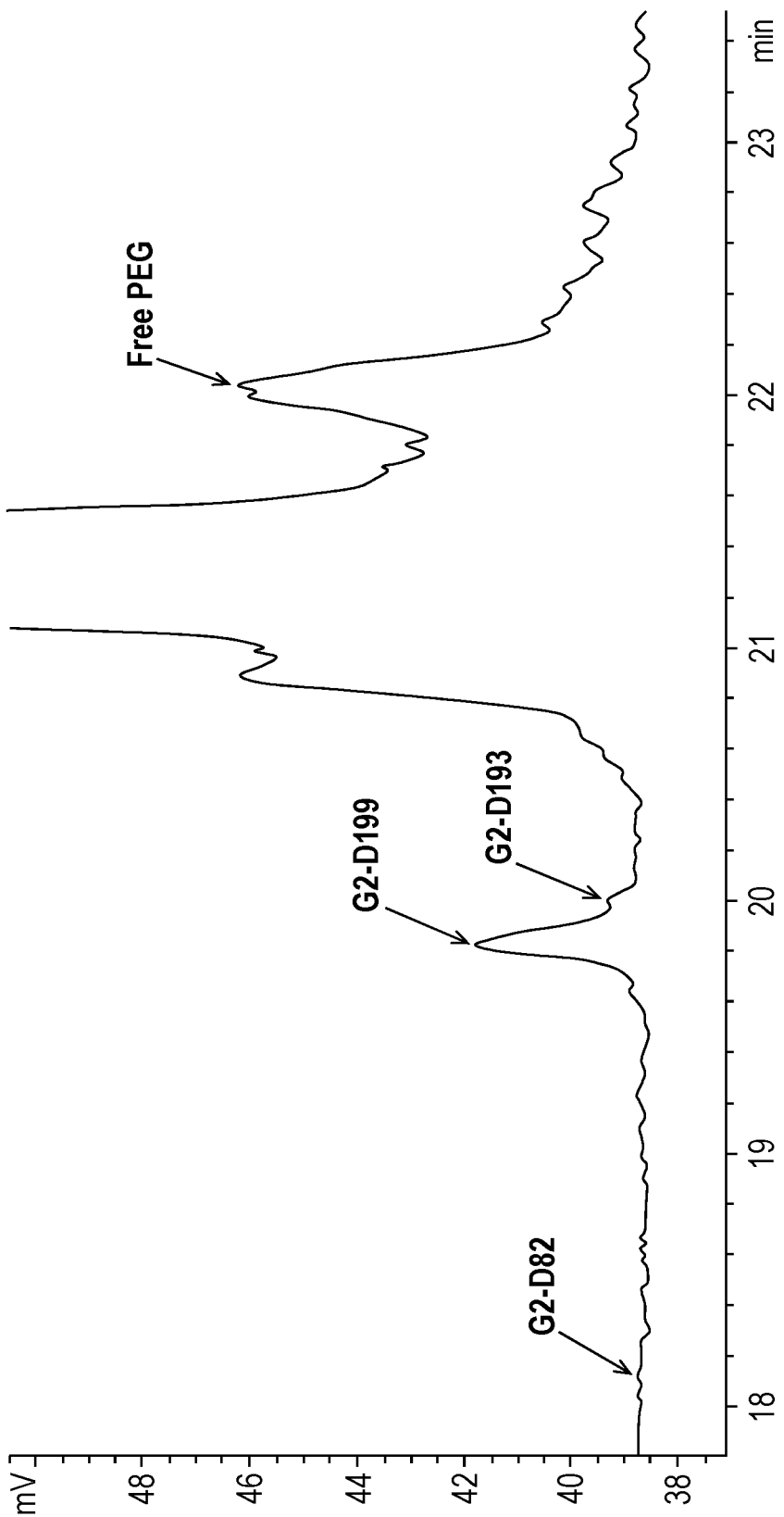
FIG. 12. LC-MS data demonstrating that the major cleavage site in the E/I(2DK−) molecule (SEQ ID NO: 25) is D199.

Characterization of clipped sites in E/I(2DK−) was performed using LC-MS as described in Example 4. E/I(2DK−) was formulated in 10 mM succinic acid, 5% sorbitol, pH 4.0, at 5 mg/mL protein concentration and was maintained at 25° C. to induce protein stress. FIG. 12 depicts the LC-MS data from this experiment and demonstrates that similar to E/I (DK−, no C-term), the predominant aspartate residues involved in fragmentation in E/I(2DK−) were D199, D82 and D193. Also, as illustrated in Table 3 below, the percentage of total clips was more than halved in E/I(2DK−) after 4 weeks, as compared to E/I (DK+) after this same period (3.5% compared to 7.5%). These results indicate that E/I (2DK−) is associated with reduced fragmentation as compared to E/I(DK+).

TABLE 3

Amount and location of fragmentation for various E/I binders after four weeks of storage at 25° C.

| Construct | SEQ ID NO | Clip Sites Identified (in order of intensity) | % Total Clips at 4 wks (value at T = 0) |
|---|---|---|---|
| E/I(DK+) | 23 | D218K<br>D199G<br>D95K | 7.5%<br>(0.5%) |
| E/I(DK−, no C-term) | 24 | D199G<br>D193Y<br>D82Y | 3.8%<br>(1.4%) |
| E/I(2DK−) | 25 | D199G<br>D193Y<br>D82Y | 3.5%<br>(0.9%) |

As discussed above, the D199 site is located within the FG binding loop of the EGFR-binding region. As such, D199 likely is necessary for binding function and will be difficult to remove from the E/I(2DK−) or E/I(DK−, no C-term) molecules.

The exact mechanism of clipping at the aspartic acid sites observed in V/I(DK+) and E/I(DK+) is not clear. Based on apparent pKa values of three aspartic acids in glucagon as measured by NMR methods, Joshi et al. (Journal of Pharmaceutical Sciences, 94 (9), 2005) proposed several mechanisms for the cleavage reaction at aspartic acid sites. Without wishing to be bound by theory, it is possible that some of the proposed mechanisms involve cyclization of the aspartic acid side chain to form a five-member ring, followed by nucleophilic attack on the peptide carbonyl which then leads to peptide bond cleavage. By substituting aspartic acid with glutamic acid, it is possible that the ring formation does not occur as readily due to steric hindrance, thus preventing peptide bond cleavage at that location.

Example 7: Evaluation of Aggregation and Fragmentation in DK Minus V/I Variants

The stability of two VEGFR-IGFR (VI) fibronectin based scaffold proteins has been compared. The first construct is VI(DK+) (SEQ ID NO: 56), and the second construct VI(DK−) (SEQ ID NO: 57) contains substitution of aspartic acid with glutamic acid at positions 94 and 199 of SEQ ID NO: 56.

Both molecules were formulated at 3 mg/mL protein concentration, in 10 mM succinic acid, 5% sorbitol, at pH 4.0, 4.5 and 5.5. Limited stability of these formulations was performed at 4 and 25° C. for up to two months, with periodic time points pulled for analysis by SE-HPLC and RP-HPLC. In addition, LC-MS characterization was performed on the 2-month 25° C. samples in order to determine the exact clipped sites in both proteins.

Effects of pH on Aggregation Rate in VI Fibronectin Based Scaffold Proteins

Figure 13:
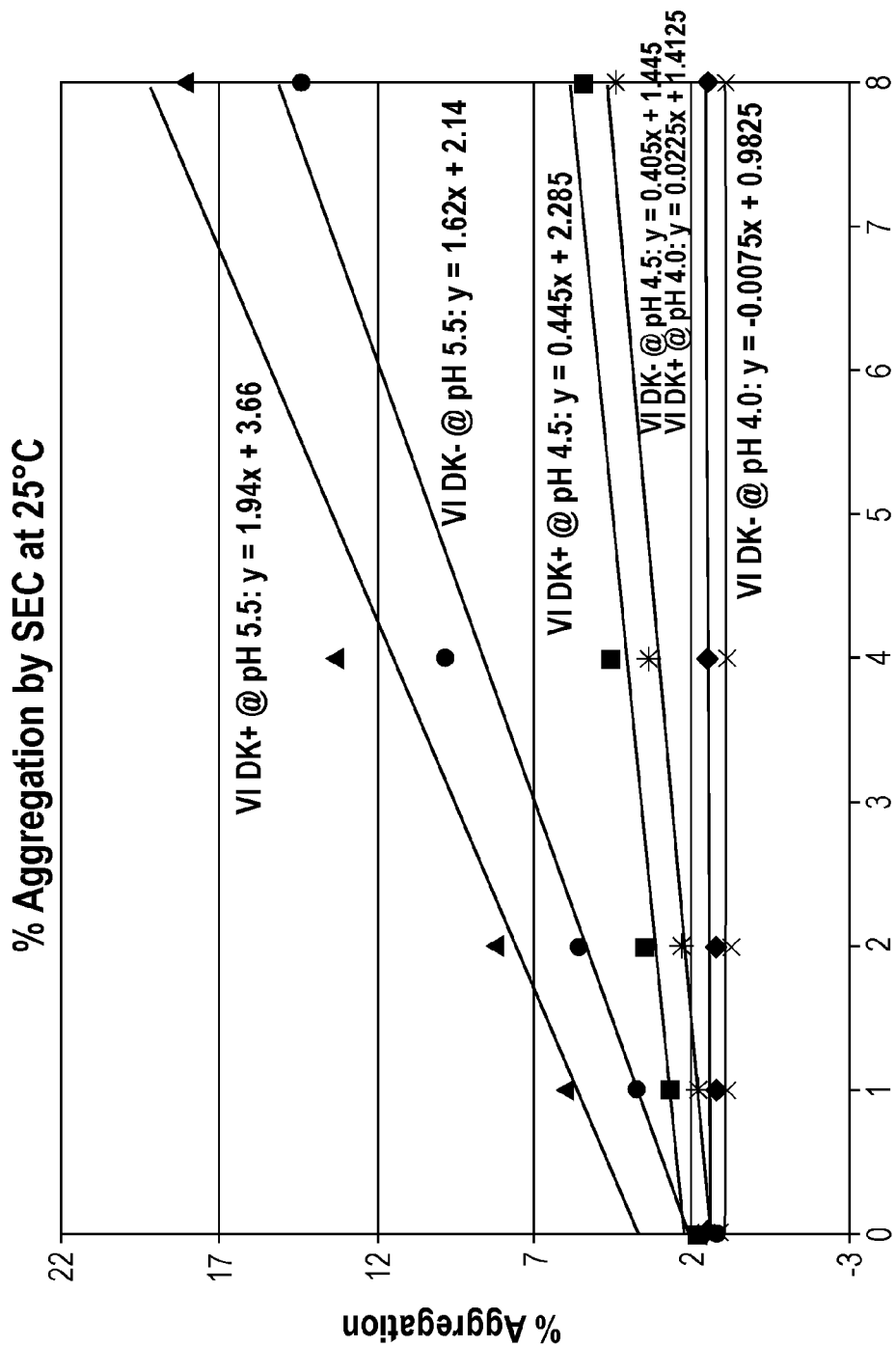
FIG. 13. The rates of aggregation observed in VI(DK+) (SEQ ID NO: 56) and VI(DK−) (SEQ ID NO: 57), under 25° C. storage for up to two months, as assessed by SE-HPLC analysis.

Based on experience with past fibronectin based scaffold proteins, low pH formulations have been recognized to provide the best biophysical stability for these molecules (i.e., lower aggregation). In the current study, the two VI constructs demonstrate the same trend as that seen before, as illustrated in FIG. 13. Although the starting levels of aggregates are slightly different between the two molecules, the rates observed over the stability period are very similar at each given pH, with the aggregation rates for both molecules showing the same order, pH 5.5>>pH 4.5>pH 4.0.

Effects of pH on Clip Rate in VI Fibronectin Based Scaffold Proteins

Figure 14:
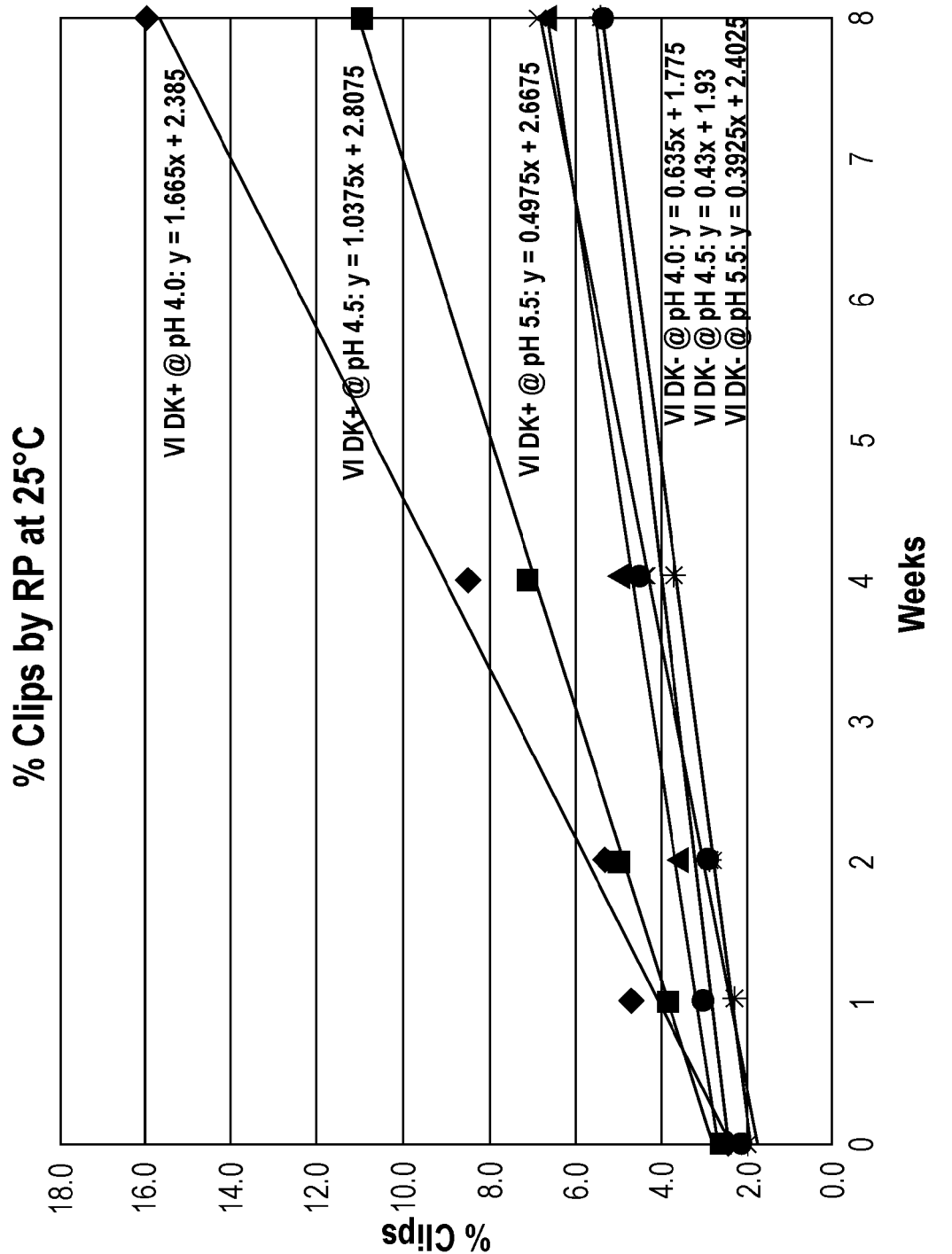
FIG. 14. Clip rates observed in VI(DK+) (SEQ ID NO: 56) and VI(DK−) (SEQ ID NO: 57), under 25° C. storage for up to two months, as assessed by RP-HPLC analysis.

Based on experience with past fibronectin based scaffold proteins, low pH formulations have been recognized to provide the least chemical stability for these proteins, if sites susceptible to clipping exist in the protein sequence. In past stability studies conducted for VI(DK+) (SEQ ID NO: 56), numerous clip sites have been identified, with clipping at D94 and D199 being the most severe. In the current study, the two VI constructs demonstrate the same trend as seen before, as illustrated in FIG. 14, with the pH effects on clip rate being worse for VI(DK+) than for VI(DK−). While the clip rate follows the general trend of pH 4.0>pH 4.5>pH 5.5 for both molecules, VI(DK−) exhibits much less difference in its clip rate across all three pH values.

From the stability data trends shown in FIGS. 13 and 14, the clip rate per week for VI(DK+) increases by 3.3-fold when the formulation pH is decreased from 5.5 to 4.0, whereas for the VI(DK−) molecule, this rate increases by 1.6-fold, due to the elimination of the major clip sites at two positions. Therefore, with these amino acid substitutions, the clip rate in the VI fibronectin based scaffold protein has decreased by about 50% over the same stability period when the pH 4 formulation is used. On the other hand, the aggregation rates per week for VI(DK+) and VI(DK−) decrease by 86- and 216-fold, respectively, when the formulation pH is decreased from 5.5 to 4.0. The pH effect on aggregation rate, therefore, is more drastic than on the clip rate in VI fibronectin based scaffold proteins.

Identification of Clipped Sites by LC-MS

Figure 15:
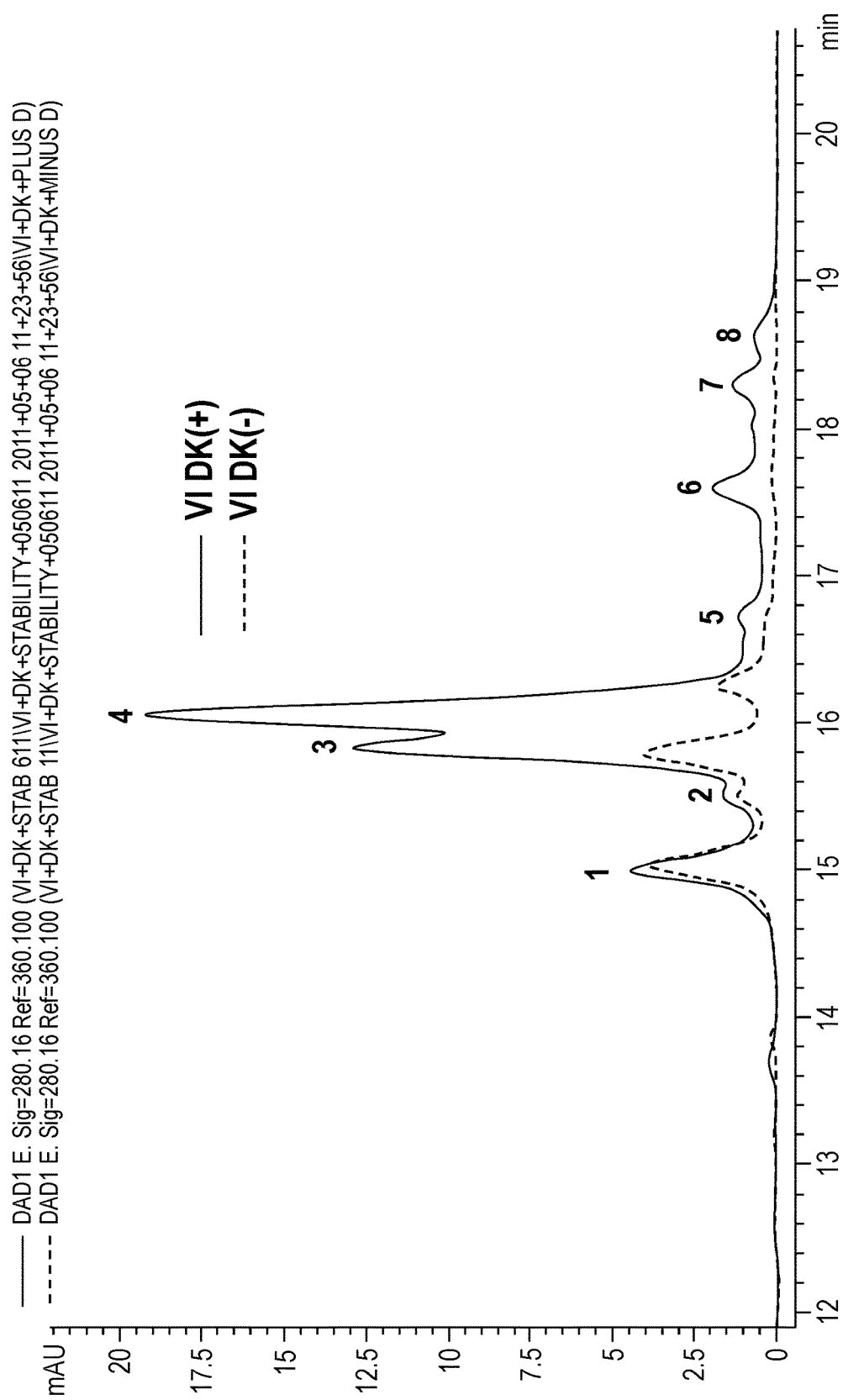
FIG. 15. Clip region of a RP-HPLC overlaid chromatogram of VI(DK+) (SEQ ID NO: 56) and VI(DK−) (SEQ ID NO: 57), after incubation for 2 months at 25° C. The total % clips for VI(DK+) is 16%, whereas for VI(DK−) it is 6.9%.

Structural characterization of the observed clipped sites in VI(DK+) and VI(DK−) has been performed by LC-MS. The overlaid RP-HPLC chromatogram of the clip region from the 25° C./2-month time point can be seen in FIG. 15 and peak identification is summarized in Table 4.

Table 4. Summary of peak identification by mass spectrometry.

TABLE 4

Summary of peak identification by mass spectrometry.

| Peak # | Structure of Clips in VI(DK+) | Peak Area % Among All Clips in VI(DK+) | Structure of Clips in VI(DK−) | Peak Area % Among All Clips in VI(DK−) |
|---|---|---|---|---|
| 1 | G1-D105 | 11.6 | G1-D105 | 37.8 |
| 2 | G1-D81 | 3.1 | G1-D81 | 7.9 |
| 3 | G1-D94 | 24.7 | G1-R80 | 36.3 |
| 4 | G1-D199 | 43.0 | G1-D179 | 14.1 |
| 5 | G1-K200 | 3.7 | T15-D81 | 3.9 |
| 6 | (G1-D199)-18 | 5.1 | n/a | n/a |
| 7 | (G1-D199)-35 | 3.2 | n/a | n/a |
| 8 | D109-Q203 | 1.9 | n/a | n/a |

While some clips remain identical between the two molecules, the major clip sites at D94 and D199 have been eliminated in VI(DK−), bringing the level of total clips to 6.9% after 2 months of stress at 25° C. On the other hand, the total clips in VI(DK+) remained high at 16.0% over the same stability period. Other clips at low level have also been identified in VI(DK−), which are not found in VI(DK+).

TABLE 5

Comparison of Clip Rates in VI(DK+) and VI(DK−).

| Formulation pH | Rate for VI(DK+) (% per week) | Rate for VI(DK−) (% per week) |
|---|---|---|
| 4.0 | 1.6650 | 0.6350 |
| 4.5 | 1.0375 | 0.4330 |
| 5.5 | 0.4975 | 0.3925 |

The clip rate of VI(DK+) at pH 4.0 was 1.6 fold and 3.3 fold faster than the clip rate of VI(DK+) at pH 4.5 and 5.5, respectively. The clip rate of VI(DK−) at pH 4.0 was 1.5 fold and 1.6 fold faster than the clip rate of VI(DK−) at pH 4.5 and 5.5, respectively.

TABLE 6

Comparison of Aggregation Rates in VI(DK+) and VI(DK−).

| Formulation pH | Rate for VI(DK+) (% per week) | Rate for VI(DK−) (% per week) |
|---|---|---|
| 4.0 | 0.0225 | −0.0075 |
| 4.5 | 0.4450 | 0.4050 |
| 1.9400 | 1.9400 | 1.6200 |

The agreggation rates of VI(DK+) at pH 4.5 and 5.0 were 4.4 fold and 86 fold faster, respectively, than the agreggation rate of VI(DK+) at pH 4.0. The agreggation rates of VI(DK−) at pH 4.5 and 5.0 were 4.0 fold and 216 fold faster, respectively, than the agreggation rate of VI(DK−) at pH 4.0.

The stability results obtained on two versions of the VI fibronectin based scaffold proteins demonstrate the effectiveness and benefits of selective substitutions of problematic aspartic acids to glutamic acids, for the purpose of eliminating specific chemical degradation in the fibronectin based scaffold protein. With the major chemical degradation eliminated through this approach, better biophysical stability in fibronectin based scaffold proteins may now be achieved through formulation at the lower pH. The results from the current study with VI, as well as those previously obtained from EI bi-functional fibronectin based scaffold proteins, demonstrate the necessity in eliminating certain aspartic acid residues known to be prone to clipping, which in turn allows for formulations at acidic pH to be used in order to maximize the biophysical stability in the fibronectin based scaffold proteins.

Materials and Methods

Formulation:

Each molecule was formulated into the desired formulations via tangential flow filtration (TFF) using a 30 kD MWCO membrane. At least six dia-volumes of buffer were exchanged to achieve the final formulation. Concentration of the resulting protein was verified by A280 and adjusted to 3 mg/mL with additional formulation buffer.

Vial Fill and Stability:

Each formulated protein was sterile filtered in a laminar flow hood, and filled into sterilized glass vials for stability monitoring. The vials were capped and crimped, followed by placement into temperature-controlled incubators at 4 and 25° C.

Analytical Methods:

Size Exclusion HPLC (SE-HPLC):

The analysis was conducted using a Shodex KW404-4F HPLC column (4.6*250 mm, 300 Å pore size, 5 µm particle size) and a mobile phase comprised of 10 mM succinic acid/3% sorbitol/0.4M arginine at pH 5.5. Flow rate was 0.35 mL/min and detection was conducted at 280 nm.

Reversed Phase HPLC (RP-HPLC):

The analysis was performed using a Varian PLRP-S column (4.6*250 mm, 300 Å pore size, 5 µm particle size). Separation of the various species is achieved via a gradient comprised of water/acetonitrile/trifluoroacetic acid. Flow rate was 1.0 mL/min. Dual detection was conducted at 280 nm (for protein-related species) and with evaporative light scattering (ELS, for PEG-related species).

LC-MS: Characterization of clipped sites was performed using a Jupiter C18 column (4.6*250 mm, 300 Å pore size, 5 µm particle size) coupled to a Thermo LTQ ion trap mass spectrometer (MS). The HPLC eluent was split 1:5 with 0.2 mL/min flow diverted into the MS. On-line detection at 280 nm was maintained.

INCORPORATION BY REFERENCE

All documents and references, including patent documents and websites, described herein are individually incorporated by reference to into this document to the same extent as if there were written in this document in full or in part.

The invention claimed is:

1. A fibronectin-based protein dimer comprising a first fibronectin type III tenth ($^{10}$Fn3) domain and a second $^{10}$Fn3 domain, wherein each of the first $^{10}$Fn3 domain and the second $^{10}$Fn3 domain:
   (i) comprises an AB loop, a BC loop, a CD loop, a DE loop, an EF loop, and a FG loop, wherein the first and second $^{10}$Fn3 domains have at least one loop selected from the BC, DE, and FG loops with an altered amino acid sequence relative to the sequence of the corresponding loop of the human $^{10}$Fn3 domain having the amino acid sequence of SEQ ID NO: 1;
   (ii) comprises an amino acid sequence having at least 60% identity to SEQ ID NO: 1 and binds to a target molecule; and
   (iii) comprises a C-terminal tail consisting of an amino acid sequence selected from the group consisting of SEQ ID NO: 33, SEQ ID NO: 34, and SEQ ID NO: 35.

2. The protein dimer of claim 1, wherein one or both of the first $^{10}$Fn3 domain and the second $^{10}$Fn3 domain further comprise(s) an N-terminal extension comprising a sequence selected from the group consisting of: M, MG, G, and any of SEQ ID NOs: 19-21 and 26-31.

3. The protein dimer of claim 1, wherein the first $^{10}$Fn3 domain and the second $^{10}$Fn3 domain bind to different targets.

4. The protein dimer of claim 3, wherein the first $^{10}$Fn3 domain and the second $^{10}$Fn3 domain are connected by a polypeptide linker comprising from 1-30 amino acids.

5. The protein dimer of claim 4, wherein the linker is selected from the group consisting of: a glycine-serine based linker, a glycine-proline based linker, a proline-alanine linker, and an Fn-based linker.

6. The protein dimer of claim 1, wherein the protein dimer has less than 4% fragmentation during storage in solution at pH 4.0 for at least 4 weeks.

7. The protein dimer of claim 1, further comprising one or more pharmacokinetic (PK) moieties selected from: a polyoxyalkylene moiety, a human serum albumin binding protein, sialic acid, human serum albumin, transferrin, and an Fc fragment.

8. A pharmaceutical composition comprising the protein dimer of claim 1.

* * * * *

SEQUENCE LISTING

<160> NUMBER OF SEQ ID NOS: 59

<210> SEQ ID NO 1
<211> LENGTH: 86
<212> TYPE: PRT
<213> ORGANISM: Homo sapiens

<400> SEQUENCE: 1

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
            20                  25                  30

Gly Asn Ser Pro Val Gln Glu Phe Thr Val Pro Gly Ser Lys Ser Thr
        35                  40                  45

Ala Thr Ile Ser Gly Leu Lys Pro Gly Val Asp Tyr Thr Ile Thr Val
    50                  55                  60

```
Tyr Ala Val Thr Gly Arg Gly Asp Ser Pro Ala Ser Ser Lys Pro Ile
 65                  70                  75                  80

Ser Ile Asn Tyr Arg Thr
                85

<210> SEQ ID NO 2
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Val Ala Ala Thr Pro Thr Ser Leu Leu Ile Ser Trp Ser Ala
 1               5                  10                  15

Arg Leu Lys Val Ala Arg Tyr Tyr Arg Ile Thr Tyr Gly Glu Thr Gly
                20                  25                  30

Gly Asn Ser Pro Val Gln Glu Phe Thr Val Pro Lys Asn Val Tyr Thr
            35                  40                  45

Ala Thr Ile Ser Gly Leu Lys Pro Gly Val Asp Tyr Thr Ile Thr Val
        50                  55                  60

Tyr Ala Val Thr Arg Phe Arg Asp Tyr Gln Pro Ile Ser Ile Asn Tyr
 65                  70                  75                  80

Arg Thr

<210> SEQ ID NO 3
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Val
        50                  55                  60

Tyr Ala Val Thr Asp Gly Arg Asn Gly Arg Leu Leu Ser Ile Pro Ile
 65                  70                  75                  80

Ser Ile Asn Tyr Arg Thr
                85

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Glu Lys
 1
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gly Ser Gly Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Glu Lys Pro Cys Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Ser Thr Ser Thr Ser Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Ser Gly Ser Gly Ser Gly Ser
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Gly Ser Gly Ser Gly Ser Gly Ser Gly Ser Gly Ser Gly Ser
1               5                   10                  15

Gly Ser Gly Ser
            20

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser Gly Gly Gly Ser Gly
1               5                   10                  15

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Gly
1

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Gly Pro Gly Pro Gly
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Pro Gly Pro Gly Pro Gly Pro Gly Pro Gly
1               5                   10

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ala Pro Ala Pro Ala
1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Ala Pro Ala Pro Ala Pro Ala Pro Ala Pro Ala
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Ala Pro Ala Pro Ala Pro Ala Pro Ala Pro Ala Pro Ala Pro Ala
1               5                   10                  15

Pro Ala

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Gly Val Ser Asp Val Pro Arg Asp Leu
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ser Asp Val Pro Arg Asp Leu
1               5

<210> SEQ ID NO 21
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 21

Gly Val Ser Asp Val Pro Arg Asp Leu
1               5

<210> SEQ ID NO 22
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Thr Ser Thr Ser Val Ser Asp Val Pro Arg Asp Leu Glu
            100                 105                 110

Val Val Ala Ala Thr Pro Thr Ser Leu Leu Ile Ser Trp Arg His Pro
            115                 120                 125

His Phe Pro Thr Arg Tyr Tyr Arg Ile Thr Tyr Gly Glu Thr Gly Gly
        130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr Glu Ile Asp Lys Pro Cys Gln
        195                 200

<210> SEQ ID NO 23
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asn Val Tyr Thr Ala Thr Ile Ser Gly Leu

```
            50                  55                  60
Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Asp Lys
                 85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
                115                 120                 125

Ala Thr Pro Thr Ser Leu Leu Ile Ser Trp Trp Ala Pro Val Asp Arg
                130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
                180                 185                 190

Asp Tyr Lys Pro His Ala Asp Gly Pro His Thr His Glu Ser Pro
                195                 200                 205

Ile Ser Ile Asn Tyr Arg Thr Glu Ile Asp Lys Pro Cys Gln
210                 215                 220
```

<210> SEQ ID NO 24
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Gly Val Ser Asp Val Pro Arg Asp Leu Glu Val Val Ala Ala Thr
 1               5                  10                  15

Pro Thr Ser Leu Leu Ile Ser Trp Ser Ala Arg Leu Lys Val Ala Arg
                 20                  25                  30

Tyr Tyr Arg Ile Thr Tyr Gly Glu Thr Gly Gly Asn Ser Pro Val Gln
                 35                  40                  45

Glu Phe Thr Val Pro Lys Asn Val Tyr Thr Ala Thr Ile Ser Gly Leu
 50                  55                  60

Lys Pro Gly Val Asp Tyr Thr Ile Thr Val Tyr Ala Val Thr Arg Phe
 65                  70                  75                  80

Arg Asp Tyr Gln Pro Ile Ser Ile Asn Tyr Arg Thr Glu Ile Glu Lys
                 85                  90                  95

Gly Ser Gly Ser Gly Ser Gly Ser Gly Ser Gly Ser Gly Ser Gly Ser
                100                 105                 110

Gly Ser Gly Ser Val Ser Asp Val Pro Arg Asp Leu Glu Val Val Ala
                115                 120                 125

Ala Thr Pro Thr Ser Leu Leu Ile Ser Trp Trp Ala Pro Val Asp Arg
                130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
                180                 185                 190
```

```
Asp Tyr Lys Pro His Ala Asp Gly Pro His Thr Tyr His Glu Ser Pro
        195                 200                 205

Ile Ser Ile Asn Tyr Arg Thr Glu Gly Ser Gly Cys
        210                 215                 220

<210> SEQ ID NO 25
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Trp Ala Pro Val Asp Arg
    130                 135                 140

Tyr Gln Tyr Tyr Arg Ile Thr Tyr Gly Glu Thr Gly Gly Asn Ser Pro
145                 150                 155                 160

Val Gln Glu Phe Thr Val Pro Arg Asp Val Tyr Thr Ala Thr Ile Ser
                165                 170                 175

Gly Leu Lys Pro Gly Val Asp Tyr Thr Ile Thr Val Tyr Ala Val Thr
            180                 185                 190

Asp Tyr Lys Pro His Ala Asp Gly Pro His Thr Tyr His Glu Ser Pro
        195                 200                 205

Ile Ser Ile Asn Tyr Arg Thr Glu Ile Glu Lys Pro Cys Gln
        210                 215                 220

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments

<400> SEQUENCE: 26

Met Gly Ser Asp Val Pro Arg Asp Leu
1               5
```

```
<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments

<400> SEQUENCE: 27

Met Gly Asp Val Pro Arg Asp Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments

<400> SEQUENCE: 28

Met Gly Val Pro Arg Asp Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments

<400> SEQUENCE: 29

Met Gly Pro Arg Asp Leu
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments
```

<400> SEQUENCE: 30

Met Gly Arg Asp Leu
1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: May or may not be present
<220> FEATURE:
<223> OTHER INFORMATION: See specification as filed for detailed
      description of substitutions and preferred embodiments

<400> SEQUENCE: 31

Met Gly Asp Leu
1

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Ile Glu Lys Pro Ser Gln
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Ile Glu Lys Pro
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ile Glu Lys Pro Ser
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Glu Ile Glu Lys Pro Cys
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Gly Ser Gly Ser
1               5

<210> SEQ ID NO 37
<211> LENGTH: 94
<212> TYPE: PRT
<213> ORGANISM: Homo sapiens

<400> SEQUENCE: 37

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 38
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(34)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (57)..(76)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (98)..(117)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<223> OTHER INFORMATION: See specification as filed for detailed
      description of substitutions and preferred embodiments

<400> SEQUENCE: 38

Glu Val Val Ala Ala Thr Pro Thr Ser Leu Leu Ile Ser Trp Xaa Xaa
1               5                   10                  15
```

```
Xaa Xaa Xaa Xaa Xaa Xaa Xaa Xaa Xaa Xaa Xaa Xaa Xaa
            20                  25                  30

Xaa Xaa Arg Tyr Tyr Arg Ile Thr Tyr Gly Glu Thr Gly Gly Asn Ser
        35                  40                  45

Pro Val Gln Glu Phe Thr Val Pro Xaa Xaa Xaa Xaa Xaa Xaa Xaa
 50                  55                  60

Xaa Xaa Xaa Xaa Xaa Xaa Xaa Xaa Xaa Xaa Thr Ala Thr Ile
 65                  70                  75                  80

Ser Gly Leu Lys Pro Gly Val Asp Tyr Thr Ile Thr Val Tyr Ala Val
                85                  90                  95

Thr Xaa Xaa Xaa Xaa Xaa Xaa Xaa Xaa Xaa Xaa Xaa Xaa Xaa
        100                 105                 110

Xaa Xaa Xaa Xaa Xaa Pro Ile Ser Ile Asn Tyr Arg Thr Glu Ile Glu
        115                 120                 125

Lys
```

<210> SEQ ID NO 39
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Val Val Ala Ala Thr Pro Thr Ser Leu Leu Ile Ser Trp Trp Ala
 1               5                  10                  15

Pro Val Asp Arg Tyr Gln Tyr Tyr Arg Ile Thr Tyr Gly Glu Thr Gly
                20                  25                  30

Gly Asn Ser Pro Val Gln Glu Phe Thr Val Pro Arg Asp Val Tyr Thr
            35                  40                  45

Ala Thr Ile Ser Gly Leu Lys Pro Gly Val Asp Tyr Thr Ile Thr Val
 50                  55                  60

Tyr Ala Val Thr Asp Tyr Lys Pro His Ala Asp Gly Pro His Thr Tyr
 65                  70                  75                  80

His Glu Ser Pro Ile Ser Ile Asn Tyr Arg Thr
                85                  90
```

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

```
Ser Ala Arg Leu Lys Val Ala
 1               5
```

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

```
Lys Asn Val Tyr
 1
```

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Phe Arg Asp Tyr Gln
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg His Pro His Phe Pro Thr
1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Gln Pro Pro
1

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Gly Arg Asn Gly Arg Leu Leu Ser Ile
1               5                   10

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Ile Asp Lys
1

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ile Asp Lys Pro Cys Gln
1               5

<210> SEQ ID NO 48
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Pro Ser Thr Ser Thr Ser Thr Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
    130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr Glu Ile Glu Lys Pro Cys Gln
        195                 200

<210> SEQ ID NO 49
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Pro Ser Thr Ser Thr Ser Thr Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
    130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
            180                 185                 190

Ile Asn Tyr Arg Thr Glu Ile Glu Lys Pro Ser Gln
        195                 200

<210> SEQ ID NO 50
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (206)..(206)
<223> OTHER INFORMATION: Ser or Cys

<400> SEQUENCE: 50

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Val Ser Asp Val Pro Arg
            100                 105                 110

Asp Leu Glu Val Val Ala Ala Thr Pro Thr Ser Leu Leu Ile Ser Trp
        115                 120                 125

Arg His Pro His Phe Pro Thr Arg Tyr Tyr Arg Ile Thr Tyr Gly Glu
    130                 135                 140

Thr Gly Gly Asn Ser Pro Val Gln Glu Phe Thr Val Pro Leu Gln Pro
145                 150                 155                 160

Pro Thr Ala Thr Ile Ser Gly Leu Lys Pro Gly Val Asp Tyr Thr Ile
            165                 170                 175

Thr Val Tyr Ala Val Thr Asp Gly Arg Asn Gly Arg Leu Leu Ser Ile
        180                 185                 190

Pro Ile Ser Ile Asn Tyr Arg Thr Glu Ile Glu Lys Pro Xaa Gln

-continued

```
<210> SEQ ID NO 51
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (216)..(216)
<223> OTHER INFORMATION: Ser or Cys

<400> SEQUENCE: 51

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Glu Lys
                85                  90                  95

Gly Ser Gly Ser Gly Ser Gly Ser Gly Ser Gly Ser Gly Ser Gly Ser
            100                 105                 110

Gly Ser Gly Ser Val Ser Asp Val Pro Arg Asp Leu Glu Val Val Ala
        115                 120                 125

Ala Thr Pro Thr Ser Leu Leu Ile Ser Trp Arg His Pro His Phe Pro
    130                 135                 140

Thr Arg Tyr Tyr Arg Ile Thr Tyr Gly Glu Thr Gly Gly Asn Ser Pro
145                 150                 155                 160

Val Gln Glu Phe Thr Val Pro Leu Gln Pro Pro Thr Ala Thr Ile Ser
                165                 170                 175

Gly Leu Lys Pro Gly Val Asp Tyr Thr Ile Thr Val Tyr Ala Val Thr
            180                 185                 190

Asp Gly Arg Asn Gly Arg Leu Leu Ser Ile Pro Ile Ser Ile Asn Tyr
        195                 200                 205

Arg Thr Glu Ile Glu Lys Pro Xaa Gln
    210                 215

<210> SEQ ID NO 52
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45
```

Glu Phe Thr Val Pro Leu Gln Pro Pro Thr Ala Thr Ile Ser Gly Leu
50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Glu Lys Pro Ser Thr Ser Thr Ser Thr Val Ser Asp Val Pro
            100                 105                 110

Arg Asp Leu Glu Val Val Ala Ala Thr Pro Thr Ser Leu Leu Ile Ser
            115                 120                 125

Trp Ser Ala Arg Leu Lys Val Ala Arg Tyr Tyr Arg Ile Thr Tyr Gly
130                 135                 140

Glu Thr Gly Gly Asn Ser Pro Val Gln Glu Phe Thr Val Pro Lys Asn
145                 150                 155                 160

Val Tyr Thr Ala Thr Ile Ser Gly Leu Lys Pro Gly Val Asp Tyr Thr
                165                 170                 175

Ile Thr Val Tyr Ala Val Thr Arg Phe Arg Asp Tyr Gln Pro Ile Ser
            180                 185                 190

Ile Asn Tyr Arg Thr Glu Ile Glu Lys Pro Ser Gln
            195                 200

<210> SEQ ID NO 53
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
                20                  25                  30

Tyr Tyr Arg Ile Thr Tyr Gly Glu Thr Gly Gly Asn Ser Pro Val Gln
                35                  40                  45

Glu Phe Thr Val Pro Leu Gln Pro Pro Thr Ala Thr Ile Ser Gly Leu
50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Glu Lys Pro Ser Thr Ser Thr Ser Thr Val Ser Asp Val Pro
            100                 105                 110

Arg Asp Leu Glu Val Val Ala Ala Thr Pro Thr Ser Leu Leu Ile Ser
            115                 120                 125

Trp Ser Ala Arg Leu Lys Val Ala Arg Tyr Tyr Arg Ile Thr Tyr Gly
130                 135                 140

Glu Thr Gly Gly Asn Ser Pro Val Gln Glu Phe Thr Val Pro Lys Asn
145                 150                 155                 160

Val Tyr Thr Ala Thr Ile Ser Gly Leu Lys Pro Gly Val Asp Tyr Thr
                165                 170                 175

Ile Thr Val Tyr Ala Val Thr Arg Phe Arg Asp Tyr Gln Pro Ile Ser
            180                 185                 190

Ile Asn Tyr Arg Thr Glu Ile Glu Lys Pro Cys Gln
            195                 200

<210> SEQ ID NO 54
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (206)..(206)
<223> OTHER INFORMATION: Ser or Cys

<400> SEQUENCE: 54

```
Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Glu Lys Gly Ser Gly Ser Gly Ser Gly Ser Gly Ser Val Ser
            100                 105                 110

Asp Val Pro Arg Asp Leu Glu Val Val Ala Ala Thr Pro Thr Ser Leu
        115                 120                 125

Leu Ile Ser Trp Ser Ala Arg Leu Lys Val Ala Arg Tyr Tyr Arg Ile
    130                 135                 140

Thr Tyr Gly Glu Thr Gly Gly Asn Ser Pro Val Gln Glu Phe Thr Val
145                 150                 155                 160

Pro Lys Asn Val Tyr Thr Ala Thr Ile Ser Gly Leu Lys Pro Gly Val
                165                 170                 175

Asp Tyr Thr Ile Thr Val Tyr Ala Val Thr Arg Phe Arg Asp Tyr Gln
            180                 185                 190

Pro Ile Ser Ile Asn Tyr Arg Thr Glu Ile Glu Lys Pro Xaa Gln
        195                 200                 205
```

<210> SEQ ID NO 55
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (216)..(216)
<223> OTHER INFORMATION: Ser or Cys

<400> SEQUENCE: 55

```
Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45
```

```
Glu Phe Thr Val Pro Leu Gln Pro Thr Ala Thr Ile Ser Gly Leu
 50                  55                  60

Lys Pro Gly Val Asp Tyr Thr Ile Thr Val Tyr Ala Val Thr Asp Gly
 65                  70                  75                  80

Arg Asn Gly Arg Leu Leu Ser Ile Pro Ile Ser Ile Asn Tyr Arg Thr
                 85                  90                  95

Glu Ile Glu Lys Gly Ser Gly Ser Gly Ser Gly Ser Gly Ser Gly Ser
                100                 105                 110

Gly Ser Gly Ser Gly Ser Gly Ser Val Ser Asp Val Pro Arg Asp Leu
                115                 120                 125

Glu Val Val Ala Ala Thr Pro Thr Ser Leu Leu Ile Ser Trp Ser Ala
130                 135                 140

Arg Leu Lys Val Ala Arg Tyr Tyr Arg Ile Thr Tyr Gly Glu Thr Gly
145                 150                 155                 160

Gly Asn Ser Pro Val Gln Glu Phe Thr Val Pro Lys Asn Val Tyr Thr
                165                 170                 175

Ala Thr Ile Ser Gly Leu Lys Pro Gly Val Asp Tyr Thr Ile Thr Val
                180                 185                 190

Tyr Ala Val Thr Arg Phe Arg Asp Tyr Gln Pro Ile Ser Ile Asn Tyr
                195                 200                 205

Arg Thr Glu Ile Glu Lys Pro Xaa Gln
                210                 215

<210> SEQ ID NO 56
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Val Ser Asp Val Pro Arg Asp Leu Glu Val Val Ala Ala Thr Pro
 1               5                  10                  15

Thr Ser Leu Leu Ile Ser Trp Ser Ala Arg Leu Lys Val Ala Arg Tyr
                20                  25                  30

Tyr Arg Ile Thr Tyr Gly Glu Thr Gly Gly Asn Ser Pro Val Gln Glu
             35                  40                  45

Phe Thr Val Pro Lys Asn Val Tyr Thr Ala Thr Ile Ser Gly Leu Lys
 50                  55                  60

Pro Gly Val Asp Tyr Thr Ile Thr Val Tyr Ala Val Thr Arg Phe Arg
 65                  70                  75                  80

Asp Tyr Gln Pro Ile Ser Ile Asn Tyr Arg Thr Glu Ile Asp Lys Pro
                 85                  90                  95

Ser Thr Ser Thr Ser Thr Val Ser Asp Val Pro Arg Asp Leu Glu Val
                100                 105                 110

Val Ala Ala Thr Pro Thr Ser Leu Leu Ile Ser Trp Arg His Pro His
                115                 120                 125

Phe Pro Thr Arg Tyr Tyr Arg Ile Thr Tyr Gly Glu Thr Gly Gly Asn
130                 135                 140

Ser Pro Val Gln Glu Phe Thr Val Pro Leu Gln Pro Thr Ala Thr Ile
145                 150                 155                 160

Ile Ser Gly Leu Lys Pro Gly Val Asp Tyr Thr Ile Thr Val Tyr Ala
                165                 170                 175

Val Thr Asp Gly Arg Asn Gly Arg Leu Leu Ser Ile Pro Ile Ser Ile
                180                 185                 190
```

Asn Tyr Arg Thr Glu Ile Asp Lys Pro Cys Gln
        195                 200

<210> SEQ ID NO 57
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Glu Lys Pro
                85                  90                  95

Ser Thr Ser Thr Ser Thr Val Ser Asp Val Pro Arg Asp Leu Glu Val
            100                 105                 110

Val Ala Ala Thr Pro Thr Ser Leu Leu Ile Ser Trp Arg His Pro His
        115                 120                 125

Phe Pro Thr Arg Tyr Tyr Arg Ile Thr Tyr Gly Glu Thr Gly Gly Asn
    130                 135                 140

Ser Pro Val Gln Glu Phe Thr Val Pro Leu Gln Pro Pro Thr Ala Thr
145                 150                 155                 160

Ile Ser Gly Leu Lys Pro Gly Val Asp Tyr Thr Ile Thr Val Tyr Ala
                165                 170                 175

Val Thr Asp Gly Arg Asn Gly Arg Leu Leu Ser Ile Pro Ile Ser Ile
            180                 185                 190

Asn Tyr Arg Thr Glu Ile Glu Lys Pro Cys Gln
        195                 200

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 58

His His His His His His
1               5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Ser Gly Cys
1